United States Patent

Morgans, Jr. et al.

[11] Patent Number: 5,538,969
[45] Date of Patent: * Jul. 23, 1996

[54] 4-AMINO DERIVATIVES OF 5-SUBSTITUTED MYCOPHENOLIC ACID

[75] Inventors: David Morgans, Jr., Sunnyvale; Eric B. Sjogren, Mountain View; David B. Smith, San Bruno, all of Calif.; Francisco X. Talamás, Cuernavaca, Mexico; Dean R. Artis, Menlo Park, Calif.; Alicia Cervantes, Mexico City, Mexico; Todd R. Elworthy, Palo Alto, Calif.; Mario Fernández, Cuernavaca; Fidencio Franco, Mexico City, both of Mexico; Ronald C. Hawley, Woodside, Calif.; Teresa Lara, Toluca, Mexico; David G. Loughhead, Belmont, Calif.; Peter H. Nelson, Los Altos, Calif.; John W. Patterson, Mountain View, Calif.; Alejandra Trejo, Cuernavaca, Mexico; Ann M. Waltos, San Ramon; Robert J. Weikert, Woodside, both of Calif.

[73] Assignee: Syntex (U.S.A.) Inc., Palo Alto, Calif.

[ * ] Notice: The term of this patent shall not extend beyond the expiration date of Pat. No. 5,441,953.

[21] Appl. No.: 452,245

[22] Filed: May 26, 1995

Related U.S. Application Data

[62] Division of Ser. No. 198,732, Feb. 18, 1994, Pat. No. 5,512,568.

[51] Int. Cl.$^6$ .................. A61K 31/365; A61K 31/535; C07D 307/88; C07D 413/12
[52] U.S. Cl. .................. 514/233.5; 514/422; 514/444; 514/450; 514/459; 514/470; 544/153; 548/230; 548/525; 549/60; 549/310
[58] Field of Search .................. 544/153; 549/310; 514/233.5

[56] References Cited

U.S. PATENT DOCUMENTS

| | | |
|---|---|---|
| 3,825,571 | 7/1974 | Mori et al. . |
| 3,853,919 | 12/1974 | Mori et al. . |
| 4,686,234 | 8/1987 | Nelson et al. . |
| 4,725,622 | 2/1988 | Nelson et al. . |
| 4,727,069 | 2/1988 | Nelson et al. . |
| 4,748,173 | 5/1988 | Nelson et al. . |
| 4,753,935 | 6/1988 | Nelson et al. . |
| 4,786,637 | 11/1988 | Allison et al. . |
| 4,808,592 | 2/1989 | Nelson et al. . |
| 4,861,776 | 8/1989 | Nelson et al. . |
| 4,868,153 | 9/1989 | Allison et al. . |
| 4,948,793 | 8/1990 | Allison et al. . |
| 4,952,579 | 8/1990 | Nelson et al. . |
| 4,959,387 | 9/1990 | Nelson et al. . |
| 4,992,467 | 2/1991 | Allison et al. . |
| 5,247,083 | 9/1993 | Knox et al. . |
| 5,441,953 | 8/1995 | Sjogren et al. .................. 514/233.5 |

FOREIGN PATENT DOCUMENTS

| | | |
|---|---|---|
| 48-086860 | 11/1973 | Japan . |
| 1-290667 | 11/1989 | Japan . |

OTHER PUBLICATIONS

Suzuki, et al., "Antitumor Activity of Derivatives of Mycophenolic Acid", *The Journal of Antibiotics*, Mar. 1976, vol. XXIX, No. 3, pp. 275–285.

Carman, et al., "Derivatives of Mycophenolic Acid", *Aust. J. Chem.*, 1978, 31, pp. 353–364.

Nelson, et al., "Synthesis and Immunosuppressive Activity of Some Side-Chain Variants of Mycophenolic Acid", *J. Med. Chem.*, 1990, 33, pp. 833–838.

Patterson, et al., "The Orthoester Claisen Rearrangement in the Synthesis of Mycophenolic Acid", *J. Chem. Soc., Chem. Commun.*, 1991, No. 21, pp. 1579–1580.

Primary Examiner—Robert W. Ramsuer
Attorney, Agent, or Firm—Heller Ehrman White & McAuliffe

[57] ABSTRACT

The disclosed derivatives of mycophenolic acid are therapeutic agents advantageous in the treatment of disease states indicated for mycophenolic acid and/or mycophenolate mofetil and other immunosuppressant agents.

17 Claims, No Drawings

4-AMINO DERIVATIVES OF 5-SUBSTITUTED MYCOPHENOLIC ACID

This is a division of application Ser. No. 08/198,732 filed Feb. 18, 1994, now U.S. Pat. No. 5,512,568.

CROSS-REFERENCE TO RELATED APPLICATIONS

This application is related to the following co-pending applications: Ser. Nos. 08/198,749, Attorney Docket No. 27960, entitled "5-Substituted Derivatives of Mycophenolic Acid"; 08/198,817, Attorney Docket No. 27970, entitled "4-Amino Derivatives of Mycophenolic Acid"; 08/198,725, Attorney Docket No. 27990, entitled "6-Substituted Mycophenolic Acid and Derivatives"; and 08/198,741, Attorney Docket No. 28000, entitled "4-Amino 6-Substituted Mycophenolic Acid and Derivatives"; filed contemporaneously herewith and incorporated herein by reference.

FIELD OF THE INVENTION

The present invention relates to mycophenolic acid derivatives in which the 4-hydroxy group has been replaced by amino substituents. The invention includes natural and derivative side chains at the 5-position. The invention is also directed to formulations and methods for treatment.

BACKGROUND INFORMATION AND RELATED DISCLOSURES

Mycophenolic acid ("MPA") is a weakly active antibiotic found in the fermentation broth of *Penicillium brevicompactum*, having the following structure:

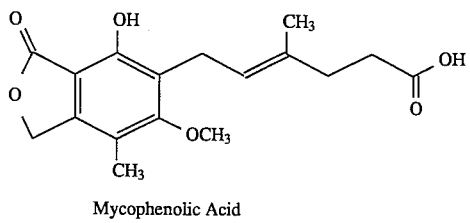

Mycophenolic Acid

MPA and certain related compounds, such as mycophenolate mofetil (the morpholinoethyl ester of MPA), having the following structure:

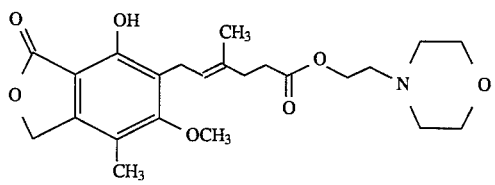

have more recently been described as having particularly advantageous properties as immunosuppressant drugs.

Various derivatives of mycophenolic acid, their synthesis and uses in the treatment of autoimmune disorders, psoriasis, inflammatory diseases, including, in particular, rheumatoid arthritis, tumors, viruses, and for treatment of allograft rejection, are described in U.S. Pat. Nos. 4,686,234; 4,725,622; 4,727,069; 4,748,173; 4,753,935; 4,786,637; 4,808,592; 4,861,776; 4,868,153; 4,948,793; 4,952,579; 4,959,387; 4,992,467; 5,247,083; and U.S. patent application Ser. No. 07/927,260, filed Aug. 7, 1992.

As immunosuppressive agents, the previously described esters and derivatives of mycophenolic acid are useful in treating auto-immune related disorders, glomerulonephritis and hepatitis, and in preventing allograft rejection. As anti-inflammatory agents, they are useful in treating rheumatoid arthritis. As anti-tumor agents, they are useful in treating solid tumors and malignancies of lymphoreticular origins.

See also U.S. Pat. Nos. 3,825,571 and 3,853,919; Japanese Pat. No. J 01290667; *J. Med. Chem.*, 33 (2), 833–8 (1990); *Austr. J. Chem.*, 31 (2), 353–64, (1978); and *J. Antibiot.*, 29(3), 275–85, 286–91 (1976). The disclosed compounds are described as having anti-tumor, immunosuppressive, anti-viral, anti-arthritic and/or anti-psoriatic activities. The article by J. W. Patterson and G. Huang, *Chemical Communications*, 1579 (1991) describes synthetic methodology of interest with respect to such compounds.

The above-cited patents, publications, and the references/publications referenced therein, are all incorporated herein by reference.

SUMMARY OF THE INVENTION

Derivatives of mycophenolic acid and their esters and the pharmaceutically acceptable salts thereof, i.e. the compounds of Formula I:

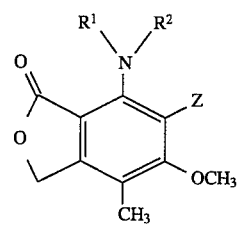

wherein:

$R^1$ is hydrogen or lower alkyl;

$R^2$ is hydrogen, lower alkyl, —C(O)$R^3$, —C(O)N$R^4R^5$, —CO$_2R^6$, or —SO$_2R^3$ where:

$R^3$ is hydrogen, lower alkyl, halo lower alkyl or optionally substituted phenyl;

$R^4$ is hydrogen, lower alkyl or optionally substituted phenyl;

$R^5$ is hydrogen, lower alkyl or optionally substituted phenyl;

$R^6$ is lower alkyl or optionally substituted phenyl; and

Z is a side chain selected from Formulae ZA, ZB, ZC, ZD, ZE, ZF, ZG, and ZH:

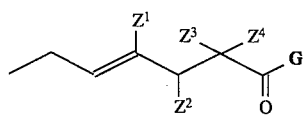

Formula ZA wherein:

$Z^1$ is H, lower alkyl, halo or CF$_3$;

$Z^2$ is H, lower alkyl, lower alkoxy, aryl, or —CH$_2Z^{13}$, where $Z^{13}$ is aryl or heteroaryl;

$Z^3$ is H, lower alkyl, lower alkenyl, lower alkoxy, phenyl, —P(O)(OCH$_3$)$_2$, —P(O)(OH)(OCH$_3$), or —S(O)$_mZ^{12}$, where
  $Z^{12}$ is lower alkyl, and
  m is 0, 1 or 2;

$Z^4$ is H, lower alkyl, or phenyl, or $Z^3$ and $Z^4$ taken together with the carbon to which they are attached form cycloalkyl of three to five carbon atoms; and G is OH, lower alkoxy, lower thioalkyl, —NG$^1$G$^2$, —O(CH$_2$)$_n$NG$^1$G$^2$, or —O(CH$_2$)$_n$N=G$^3$, where
  n is an integer from 1 to 6,
  G$^1$ is H or lower alkyl,
  G$^2$ is H or lower alkyl, and
  =G$^3$ is lower alkylene of four to six carbon atoms, or lower alkylene of three to five carbon atoms plus one member that is —O—, —S—, or —N(G$^4$)— where G$^4$ is H or lower alkyl;
provided that when Z$^1$ is methyl, Z$^2$, Z$^3$ and Z$^4$ are not all H; or

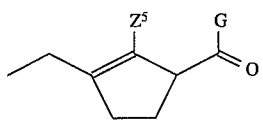

Formula ZB wherein:
Z$^5$ is H or lower alkyl;
Z$^8$ is H or lower alkyl;
D$^1$ and D$^2$ together with their adjacent carbon atoms form an optionally substituted, saturated or unsaturated carbocyclic or heterocyclic ring of 3 to 7 atoms; and
G is as defined above; or

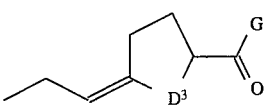

Formula ZC wherein:
Z$^5$, Z$^8$, and G are as defined above; or

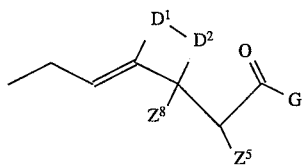

Formula ZD wherein:
D$^3$ is —CH$_2$— or —CH$_2$CH$_2$—; and
G is as defined above; or

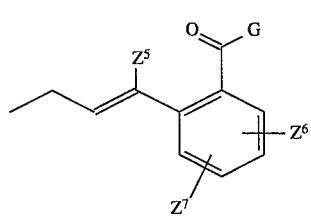

Formula ZE wherein:
Z$^6$ is H, lower alkyl, lower alkoxy, —COOH, —NH$_2$ or halo;
Z$^7$ is H, lower alkyl, lower alkoxy or halo; and
Z$^5$ and G are as defined above; or

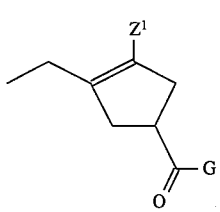

Formula ZF wherein:
Z$^1$ and G are as defined above; or

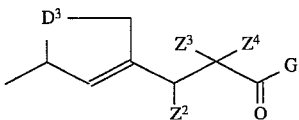

Formula ZG wherein:
D$^3$, Z$^2$, Z$^3$, Z$^4$ and G are as defined above; or

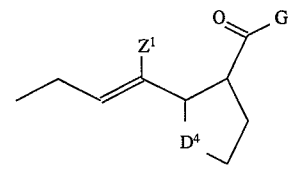

Formula ZH wherein:
D$^4$ is —CH$_2$—, —CH$_2$CH$_2$—, —CH$_2$CH$_2$CH$_2$—, —O—, or —OCH$_2$—; and
Z$^1$ and G are as defined above;
and the pharmaceutically acceptable salts thereof.

In still another aspect, the invention relates to a pharmaceutical composition containing a therapeutically effective amount of a compound of Formula I admixed with at least one pharmaceutically acceptable excipient.

In still another aspect, the invention relates to a method of treating immune, inflammatory, tumor, proliferative, viral and psoriatic disorders in a mammal by administering to a mammal in need of such treatment a therapeutically effective amount of a compound of Formula I or a pharmaceutically acceptable salt thereof.

DETAILED DESCRIPTION OF THE INVENTION

Definitions and General Parameters

The following definitions are set forth to illustrate and define the meaning and scope of the various terms used to describe the invention herein.

As used herein, the term "alkyl" refers to a fully saturated monovalent radical of one to twelve carbon atoms containing only carbon and hydrogen, and which may be a cyclic, branched or straight chain radical. This term is further exemplified by radicals such as methyl, ethyl, t-butyl, pentyl, cyclopentyl, cyclohexyl, heptyl, cycloheptyl and adamantyl.

The term "lower alkyl" refers to a monovalent alkyl radical of one to six carbon atoms. This term is further exemplified by such radicals as methyl, ethyl, n-propyl, isopropyl, cyclopropyl, n-butyl, t-butyl, i-butyl (or 2-methylpropyl), isoamyl, pentyl, cyclopentyl, i-pentyl, hexyl and cyclohexyl.

The term "lower alkenyl" refers to an unsaturated monovalent hydrocarbon radical of one to six carbon atoms. This term is further exemplified by such radicals as vinyl, prop-2-enyl, pent-3-enyl, and hex-5-enyl.

The term "halo" refers to fluoro and chloro, unless otherwise specified.

The term "halo lower alkyl" refers to a lower alkyl radical substituted with one or more chlorine or fluorine atoms. This term is further exemplified by such radicals as trichloromethyl, trifluoromethyl, dichloromethyl, fluoromethyl, difluoro-chloro-methyl, 3-chloropropyl and 4-trifluoro-2-chloro-butyl.

The term "halomethyl" refers to a methyl radical substituted with one or more chlorine and/or fluorine atoms. This term is further exemplified by such radicals as trichloromethyl, trifluoromethyl, dichloromethyl, fluoromethyl and difluoro- chloromethyl.

The term "lower alkylene" refers to a divalent alkyl radical of one to six carbon atoms. This term is further exemplified by such radicals as methylene, ethylene, n-propylene, i-propylene, n-butylene, t-butylene, i-butylene (or 2-methylpropylene), isoamylene, pentylene, and n-hexylene.

The term "alkoxy" means the group —OR wherein R is lower alkyl.

The term "lower alkanol" means an alcohol of the formula ROH where R is a lower alkyl. This term is further exemplified by such alcohols as methanol, ethanol, n-propanol, i-propanol, n-butanol, t-butanol, i-butanol (or 2-methylpropanol), pentanol, n-hexanol.

The moiety "—N=$G^3$" as defined represents a heterocycle radical such as pyrrolidino, piperidino, hexamethyleneimino, imidazolidino, thiazolidino, morpholino, thiomorpholino, piperazino, thiopentamethyleneimino, and the like.

The term "optionally substituted phenyl" refers to phenyl and mono-, di-, or tri-substituted phenyl, wherein the optional substituents are lower alkyl, lower alkoxy, hydroxy, trifluoromethyl, or halo. This term is further exemplified by such radicals as 2-chlorophenyl, 2-trifluoromethylphenyl, 4-methoxyphenyl, 4-chlorophenyl, 3,4-dimethoxyphenyl, 2-chloro-3,4-dimethoxyphenyl, 4-hydroxyphenyl, 4-methylphenyl, 3-t-butylphenyl, and 4-hexylphenyl.

The term "aryl" refers to a monovalent unsaturated aromatic carbocyclic radical having a single ring (e.g., phenyl) or two condensed rings (e.g., naphthyl), which can optionally be mono-, di- or tri-substituted, independently, with OH, COOH, lower alkyl, lower alkoxy, chloro, fluoro, trifluoromethyl and/or cyano.

The term "heteroaryl" refers to a monovalent aromatic carbocyclic radical having at least one heteroatom, such as N, O or S, within the ring, such as quinolyl, benzofuranyl, pyridyl, morpholinyl and indolyl, which can optionally be mono-, di-or tri-substituted, independently, with OH, COOH, lower alkyl, lower alkoxy, chloro, fluoro, trifluoromethyl and/or cyano.

The term "optionally substituted, saturated or unsaturated carbocyclic or heterocyclic ring of 3 to 7 atoms" as used with reference to a side chain of Formula ZB encompases side chains of the following structures:

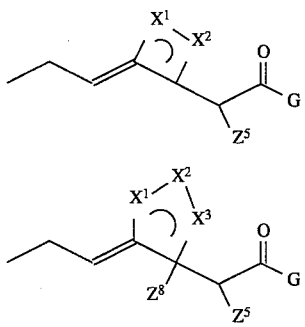

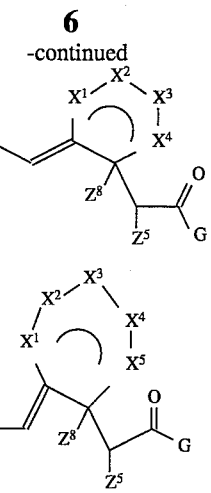

where the line inside each respective ring indicates the optional presence of a double bond and $X^1$, $X^2$, $X^3$, $X^4$ and $X^5$ can independently be —CHX$^a$—, —C(O)—, —C(N-X$^b$)—, —C(N-NX$^d$X$^e$)—, —O—, —S—, —S(O)—, —S(O)$_2$-or —NX$^c$—, where $X^a$ is H, lower alkyl or forms a double bond;

$X^b$ is acyl, carbamoyl or ureido;

$X^c$ is lower alkyl, C(O)X$^4$, S(O)$_2$X$^4$ or C(O)N$^d$X$^e$; and $X^d$ and $X^e$ are independently H or lower alkyl;

provided that if more than one heteroatom is present such heteroatoms are separated by at least one carbon atom. Thus, a sidechain of Formula ZB in which $D^1$ and $D^2$ together represent —CH$_2$CH$_2$CH$_2$CH$_2$—, and $Z^5$ and $Z^8$ are both hydrogen, would be named as a 2-[(2-ethylidene)-2-cyclohex-1-yl]acetic acid derivative. Likewise, a sidechain of Formula ZB in which $D^1$ and $D^2$ together represent —CH$_2$CH$_2$OCH$_2$—, and $Z^5$ and $Z^8$ are both hydrogen, would be named as a 2-[(2-ethylidene)-4-tetrahydropyran-3-yl]acetic acid derivative.

The term "optional" or "optionally" means that the subsequently described event or circumstance may or may not occur, and that the description includes instances in which said event or circumstance occurs and instances in which it does not. For example, "optionally substituted phenyl" means that the phenyl may or may not be substituted and that the description includes both unsubstituted phenyl and phenyl wherein there is substitution: "optionally" followed by "converting the free base to the acid addition salt" means that such conversion may or may not be carried out in order for the process described to fall within the invention, and the invention includes those processes wherein the free base is converted to the acid addition salt and those processes in which it is not.

A "pharmaceutically acceptable salt" may be any salt derived from an inorganic or organic acid or base. Salts may be derived from acids or bases.

The acid addition salts are derived from inorganic acids, such as hydrochloric acid, hydrobromic acid, sulfuric acid (giving the sulfate and bisulfate salts), nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, salicylic acid, p-toluenesulfonic acid, and the like.

The base addition salts are derived from inorganic bases such as sodium hydroxide, potassium hydroxide, lithium hydroxide, ammonia, calcium hydroxide, magnesium hydroxide and the like. Cations derived from organic bases include those formed from primary, secondary and tertiary amines, such as isopropylamine, diethylamine, trimethylamine, triethylamine, pyridine, cyclohexylamine, ethylene diamine, monoethanolamine, diethanolamine, triethanolamine, and the like.

As used herein, the term "inert organic solvent" or "inert solvent" means a solvent inert under the conditions of the reaction being described in conjunction therewith (including, for example, benzene, toluene, acetonitrile, tetrahydrofuran, diethyl ether, chloroform, methylene chloride, pyridine, xylene, dimethylformamide, 1,4-dioxane, dichloromethane, and the like).

As used herein, the term "treatment" or "treating" means any treatment of a disease in a mammal, and includes:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "effective amount" means a dosage sufficient to provide treatment. This will vary depending on the patient and the treatment being effected.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn-Ingold-Prelog R-S system. When the compound is a pure enantiomer the stereochemistry at each chiral carbon may be specified by either R or S. Resolved compounds whose absolute configuration is unknown are designated (+) or (−) depending on the direction (dextro-or laevorotary) which they rotate the plane of polarized light at the wavelength of the sodium D line.

When a compound is a racemic mixture the stereochemistry at each chiral carbon may be specified by either RS or SR by reference to a single enantiomer of the racemate. In this manner relative stereochemistry is conveyed unambiguously.

The compounds of the invention may possess one or more asymmetric centers, and can be produced as a racemic mixture or as individual enantiomers or diastereoisomers. The number of stereoisomers present in any given compound of Formula I depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis, or by resolution of the compound of Formula I by conventional means. The individual stereoisomers (including individual enantiomers and diastereoisomers) as well as racemic and non-racemic mixtures of stereoisomers are encompassed within the scope of the present invention, all of which are intended to be depicted by the structures of this specification unless otherwise specifically indicated. Specific examples of the separation of isomers are set forth in the Examples.

Unless specified to the contrary, the reactions described herein take place at atmospheric pressure over a temperature range from about −20° C. to about 100° C., more preferably from about 10° C. to about 50° C., and most preferably at about room temperature.

Isolation and purification of the confounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be found by reference to the examples hereinbelow. However, other equivalent separation or isolation procedures can, of course, also be used.

Nomenclature

The compounds of Formula I will be named using the numbering system illustrated below.

The isobenzofuranyl nucleus of the compounds of Formula I is numbered as follows:

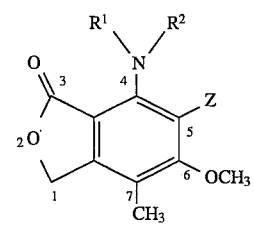

Following are examples of how some representative compounds of Formula I are named.

Sidechains of Formula ZA are numbered as shown below:

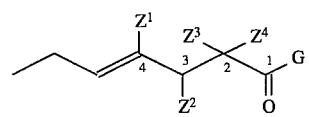

Representative compounds of Formula I where the sidechain is ZA are as follows:

| No. | $R^1$ | $R^2$ | $Z^1$ | $Z^2$ | $Z^3$ | $Z^4$ | G | Isomer |
|---|---|---|---|---|---|---|---|---|
| 1 | H | H | $CH_3$ | H | H | $CH_3$ | OH | S |
| 2 | H | $C(O)CF_3$ | $CH_3$ | H | H | $C_2H_5$ | OH | S |
| 3 | H | $CH_3$ | $CF_3$ | OH | $CH_3$ | Phenyl | $OCH_3$ | RS |
| 4 | H | $C(O)NMe_2$ | Cl | $CH_3$ | H | $SO_2CH_3$ | $SCH_3$ | RS | and are named:

1. (E)-6-(4-amino-1,3-dihydro-6-methoxy-7-methyl -3-oxoisobenzofuran- 5-yl)-2(S),4-dimethyl-4-hexenoic acid;

2. (E)-6-(1,3-dihydro-6-methoxy-7-methyl-3-oxo- 4-trifluoroacetylaminoisobenzofuran-5-yl)-2(S)-ethyl-4-methyl-4-hexenoic acid;

3. methyl (E)-6-(1,3-dihydro-6-methoxy-7-methyl-4-methylamino- 3-oxoisobenzofuran-5-yl)-3-hydroxy-2-methyl-2-phenyl-4-trifluoromethyl- 4-hexenoate;

4. thiomethyl (E)-4-chloro-6-(1,3-dihydro-4-(3,3-dimethylureido)- 6-methoxy- 7-methyl-3-oxoisobenzofuran-5-yl)-3-methyl-2-methylsulfonyl- 4-hexenoate.

| No. | $R^1$ | $R^2$ | $D^1-D^2$ | $Z^5$ | $Z^8$ | G | Isomer |
|---|---|---|---|---|---|---|---|
| 1 | H | H | $CH_2-O-CH_2$ | H | H | OH | RS |
| 2 | H | $C(O)CF_3$ | $(CH_2)_2-NH-CH_2$ | Methyl | Methyl | O-Hexyl | (3)-S |
| 3 | H | Methyl | $(CH_2)_2-S-CH_2$ | Hexyl | H | $NH^1G^2$ | RS |

Sidechains of Formula ZB in which $D^1$ and $D^2$ do not contain a hetero atom are numbered as shown below:

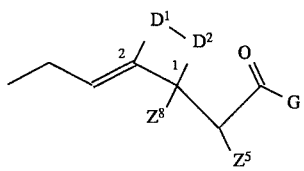

Representative compounds of Formula I where the sidechain is ZB in which $D^2$ does not include a hereto atom are as follows:

| No. | $R^1$ | $R^2$ | $D^1$ | $D^2$ | $Z^5$ | G | Isomer |
|---|---|---|---|---|---|---|---|
| 1 | H | H | $CH_2$ | $CH_2CH_2$ | H | OH | S |
| 2 | H | $CH_3$ | $(CH_2)_2$ | $CH_2CH_2$ | H | OH | RS |
| 3 | H | $C(O)CF_3$ | $(CH_2)_2$ | $(CH_2)_3$ | $CH_3$ | $NG^1G^2$ | RS |
| 4 | H | $C(O)NMe_2$ | $CH_2$ | $CH_2$ | Hexyl | $SCH_3$ | (1)-R | and are named:
1. (E)-2-{2-[2-[4-amino-1,3-dihydro-6-methoxy-7-methyl-3-oxoisobenzofuran-5-yl]ethylidene]cyclopent-1-(S)-yl} acetic acid;
2. (E)-2-{2-[2-(1,3-dihydro-6-methoxy-7-methyl-4-methylamino- 3-oxoisobenzofuran-5-yl)ethylidene]cyclohex-1-yl} acetic acid;
3. (E)-2-{2-[2-(1,3-dihydro-6-methoxy-7-methyl-4-trifluoroacetylamino- 3-oxoisobenzofuran-5-yl)ethylidene]cyclohept-1-yl}propionic acid dimethylamide (where $G^1$ and $G^2$ are both methyl);
4. thiomethyl (E)-2-{2-[2-(1,3-dihydro-4-(3,3-dimethylureido)- 6-methoxy-7-methyl-3-oxoisobenzofuran-5-yl)ethylidene]-cyclobut-1-(R)-yl} octanoate.

Sidechains of Formula ZB that include a heteroatom are numbered differently, depending upon the position of the heteroatom(s) in the ring. For example, a sidechain of Formula ZB in which $D^1$ and $D^2$ together with their adjacent carbon atoms form a saturated heterocyclic ring of 6 atoms is numbered as shown below:

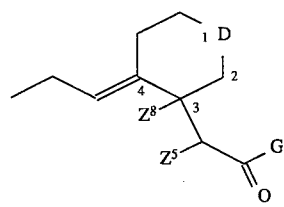

where D represents $-O-$, $-S(O)_p-$, $-N(R^9)-$, and the like.

Representative compounds of Formula I where the sidechain is ZB including a hetero atom are as follows:

and are named:
1. (E)-2-{4-[2-(4-amino-1,3-dihydro-6-methoxy-7-methyl-3-oxoisobenzofuran-5-yl)ethylidene]tetrahydrofuran-3-yl}acetic acid;
2. hexyl (E)-2-{4-[2-(1,3-dihydro-6-methoxy-7-methyl-4-trifluoroacetylamino-3-oxoisobenzofuran-5-yl)ethylidene]- 3-methylpiperidin-3(S)-yl}propionate;
3. (E)-2-{4-[2-(1,3-dihydro-6-methoxy-7-methyl-4-methylamino- 3-oxoisobenzofuran-5-yl)ethylidene]thiepan-3-yl} heptanoic acid dimethylamide (where $G^1$ and $G^2$ are both methyl).

Sidechains of Formula ZC are numbered as shown below:

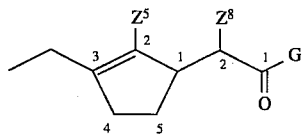

Representative compounds of Formula I where the sidechain is ZC are as follows:

| No. | $R^1$ | $R^2$ | $Z^5$ | $Z^8$ | G | Isomer |
|---|---|---|---|---|---|---|
| 1 | H | H | Methyl | H | OH | S |
| 2 | H | $C(O)CF_3$ | H | H | O-Hexyl | RS |
| 3 | H | Methyl | Methyl | i-Propyl | OH | 2-S, 1-S |
| 4 | H | H | Hexyl | H | $O(CH_2)_2NG^1G^2$ | RS | and are named:
1. 3-(4-amino-1,3-dihydro-6-methoxy-7-methyl-3-oxoisobenzofuran- 5-ylmethyl)-2-methylcyclopent-2-enyl-1-(S)-acetic acid;
2. hexyl 3-(1,3-dihydro-6-methoxy-7-methyl-4-trifluoroacetyl-amino- 3-oxoisobenzofuran-5-ylmethyl)cyclopent-2-enyl-1-acetate;
3. 2-(S)-[3-(1,3-dihydro-6-methoxy-7-methyl-4-methylamino- 3-oxoisobenzofuran-5-ylmethyl)-2-methylcyclopent-2-en-1(S)-yl]-1-(S)- 3-methylbutyric acid;
4. (2-dimethylamino)ethyl 3-(4-amino-1,3-dihydro-6-methoxy-7-methyl- 3-oxoisobenzofuran-5-ylmethyl)-2-hexyl-cyclopent-2-enyl-1-acetate (where $G^1$ and $G^2$ are both methyl).

Sidechains of Formula ZD are numbered as shown below:

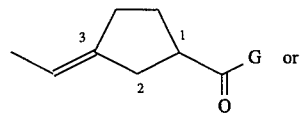

where $D^3$ is $CH_2$

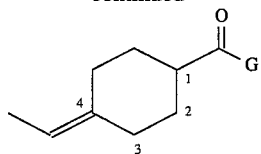

where $D^3$ is $CH_2CH_2$

Representative compounds of Formula I where the sidechain is ZD are as follows:

| No. | $R^1$ | $R^2$ | $D^3$ | G | Isomer |
|---|---|---|---|---|---|
| 1 | H | H | $CH_2$ | OH | R |
| 2 | H | $C(O)CF_3$ | $CH_2CH_2$ | O-Hexyl | RS |
| 3 | H | Methyl | $CH_2$ | S-Methyl | RS | are named as follows:
1. (E)-3-[2-(4-amino-1,3-dihydro-6-methoxy-7-methyl-3-oxoisobenzofuran- 5-yl)ethylidene] cyclopentane-1-(R)-carboxylic acid;
2. hexyl (E)-4-[2-(1,3-dihydro-6-methoxy-7-methyl- 4-trifluoroacetylamino-3-oxoisobenzofuran-5-yl)ethylidene] cyclohexane- 1-carboxylate;
3. methyl (E)-3-[2-(1,3-dihydro-6-methoxy-7-methyl-4-methylamino- 3-oxoisobenzofuran-5-yl)ethylidene]cyclopentane-1-thiocarboxylate.

Sidechains of Formula ZF are numbered as shown below:

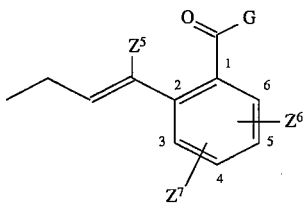

Representative compounds of Formula I where the sidechain is ZE are as follows:

| No. | $R^1$ | $R^2$ | $Z^5$ | $Z^6$ | $Z^7$ | G |
|---|---|---|---|---|---|---|
| 1 | H | H | Methyl | H | H | OH |
| 2 | H | $C(O)CF_3$ | H | 6-Methyl | H | $NG^1G^2$ |
| 3 | H | Methyl | Hexyl | 6-chloro | 4-$OCH_3$ | O-Hexyl | and are named:
1. (E)-2-[3-(4-amino-1,3-dihydro-6-methoxy-7-methyl-3-oxoisobenzofuran- 5-yl)-1-methylprop-1-en-1-yl]benzoic acid;
2. (E)-2-[3-(1,3-dihydro-6-methoxy-7-methyl-4-trifluoroacetylamino- 3-oxoisobenzofuran-5-yl)prop-1-en-1-yl]- 6-methylbenzoic acid dimethylamide (where $G^1$ and $G^2$ are both methyl);
3. hexyl (E)-6-chloro-2-[3-(1,3-dihydro-6-methoxy- 7-methyl-4-methylamino-3-oxoisobenzofuran-5-yl)-1-hexyl-prop- 1-en-1-yl]-4-methoxybenzoate.

Sidechains of Formula ZF are numbered as shown below:

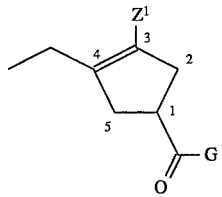

Representative compounds of Formula I where the sidechain is ZF are as follows:

| No. | $R^1$ | $R^2$ | $Z^1$ | G | Isomer |
|---|---|---|---|---|---|
| 1 | H | H | Methyl | OH | S |
| 2 | H | $C(O)CF_3$ | Hexyl | O-Ethyl | RS |
| 3 | H | Methyl | H | S-Methyl | RS | and are named:
1. 4-(4-amino-1,3-dihydro-6-methoxy-7-methyl-3-oxoisobenzofuran-5-ylmethyl)- 3-methylcyclopent-3-ene-1-(S)-carboxylic acid;
2. ethyl 4-(1,3-dihydro-6-methoxy-7-methyl-4-trifluoroacetylamino- 3-oxoisobenzofuran-5-ylmethyl)-3-hexyl-cyclopent-3-ene-1-carboxylate;
3. thiomethyl 4-(1,3-dihydro-6-methoxy-7-methyl-4-methylamino- 3-oxoisobenzofuran-5-ylmethyl)cyclopent-3-ene-1-carboxylate.

Sidechains of Formula ZG are numbered as shown below:

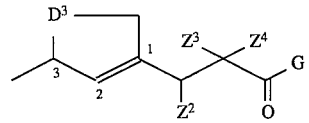

Representative compounds of Formula I where the sidechain is ZG are as follows:

| No. | $R^1$ | $R^2$ | $D^3$ | $Z^2$ | $Z^3$ | $Z^4$ | G | Isomer |
|---|---|---|---|---|---|---|---|---|
| 1 | H | H | $CH_2$ | H | H | H | OH | (3)-S |
| 2 | H | Methyl | $CH_2$ | Methyl | H | Phenyl | OH | RS | and are named:
1. 3-[3-(S)-(4-amino-1,3-dihydro-6-methoxy-7-methyl-3-oxoisobenzofuran-5-yl)cyclopent-1-en-1-yl]-propionic acid;
2. 3-[3-(1,3-dihydro-6-methoxy-7-methyl-4-methylamino-3-oxo-furan- 5yl)cyclopent-1-en-1-yl]-3-methyl-2-phenyl propionic acid.

Sidechains of Formula ZH are numbered as shown below:

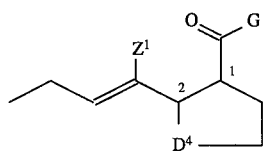

Representative compounds of Formula I where the sidechain is ZH are as follows:

| No. | R¹ | R² | D⁴ | Z¹ | H | Isomer |
|---|---|---|---|---|---|---|
| 1 | H | H | CH₂ | Methyl | OH | RS |
| 2 | H | C(O)CF₃ | (CH₂)₂ | Methyl | O-Ethyl | 1-R |
| 3 | H | Methyl | (CH₂)₃ | H | S-Methyl | RS | are named as follows:

1. (E)-2-[3-(4-amino-1,3-dihydro-6-methoxy- 7-methyl-3-oxoisobenzofuran- 5-yl)-1-methylprop-1-en-1-yl]cyclopentene-1-carboxylic acid;
2. Ethyl (E)-2-[3-(1,3-dihydro-6-methoxy-7-methyl- 4-trifluoroacetylamino-3-oxoisobenzofuran-5-yl)-1-methylprop- 1-en-1-yl]cyclohexane-1R-carboxylate;
3. Thiomethyl (E)-2-[3-(1,3-dihydro-6-methoxy-7-methyl-4-methylamino-3-oxoisobenzofuran-5-yl)prop-1-en-1-yl]cycloheptene- 1-carboxylate.

Compounds of Formula I where the side chain is ZH, in which D⁴ is a heteroatom, are numbered differently, in that the heteroatom is designated as position 1 of the ring. For example, the compound where D⁴ is oxygen, and R¹ and R³ are both hydrogen, Z¹ is methyl, and G is hydroxy, is named as follows:

(E)-2-[3-(4-amino-1,3-dihydro-6-methoxy-7-methyl-3-oxoisobenzofuran- 5-yl)-1-methylprop-1-en-1-yl]tetrahydrofuran-3-carboxylic acid.

PREPARATION OF COMPOUNDS OF FORMULA I

The compounds of Formula I are prepared from the lower alkyl 4-isocyanato esters of Formula 6, the structure of which is shown below:

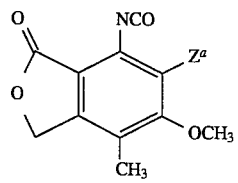

Formula 6 where $Z^a$ is a sidechain of Formula Z as defined in the Summary of the Invention in which G is lower alkoxy.

The compounds of Formula 6 are then converted to the compounds of Formula I by several different synthetic pathways, depending on the desired substitutions at the 4-position.

Many of the esterification routes and/or final esterification steps for the esters of the 4-substituted derivatives of mycophenolic acid are described in U.S. Pat. Nos. 4,686,234; 4,725,622; 4,727,069; 4,748,173; 4,753,935; 4,861,776; and the pending application entitled "Direct Esterification of Mycophenolic Acid", Ser. No. 07/911635, filed Jul. 10, 1992 (by inventors working in the same research organization as that of the present applicants, and subject to an obligation of assignment to the same assignee as in the present application) all previously incorporated herein by reference. By substituting the acids of Formula I for mycophenolic acid or its acid derivatives as described in the above references, the esterification routes and/or final steps described may likewise be used.

Starting Materials

The intermediates of Formula 6 are prepared starting from compounds of Formula 1, the structure of which is shown below:

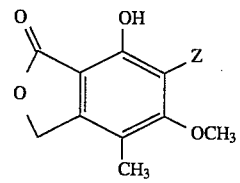

Formula 1 where Z is as defined in the Summary of the Invention.

The compounds of Formula I may be prepared as described below in Reaction Schemes I to XXII. The preparation of such compounds is also described in more detail in co-pending application Ser. No. 08/198,749, Attorney Docket No. 27960, entitled "5-Substituted Derivatives of Mycophenolic Acid", filed contemporaneously herewith, which is hereby incorporated by reference in its entirety.

Preparation of Compounds of Formula I where Z is Sidechain ZA

One method of preparing compounds of Formula 1 where Z is the sidechain of Formula ZA, illustrated as compounds of Formula 1A, is shown below in Reaction Schemes I to X.

REACTION SCHEME I

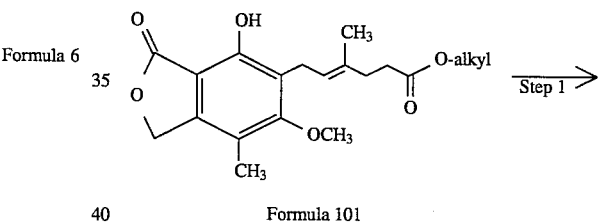

Formula 101

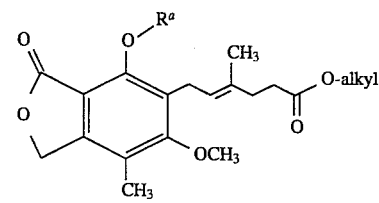

Formula 102

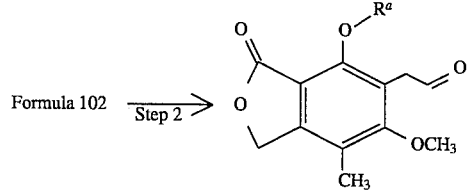

Formula 103

-continued
REACTION SCHEME I

Formula 103

+

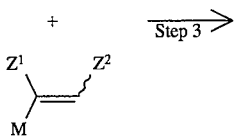

Formula 103a

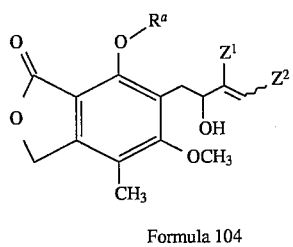

Formula 104

Formula 104

+

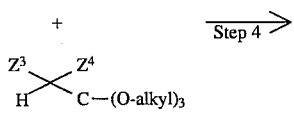

Formula 104a

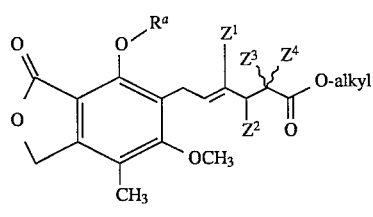

Formula 105

Formula 105 → Step 5 →

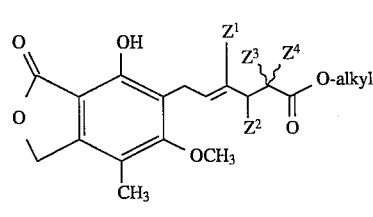

Formula 1A
as an ester

Preparation of Formula 102

As illustrated in Reaction Scheme I, Step 1, the phenolic hydroxyl group of a mycophenolic acid lower alkyl ester is protected.

A mycophenolic acid lower alkyl ester of Formula 101, in a solvent (such as ether, ethyl acetate, dimethylamide, or preferably dichloromethane), is reacted with an equimolar amount of a halogenated protecting group (such as: methoxyethoxymethyl chloride; a sulfonyl chloride, e.g., tosyl chloride, mesyl chloride; or a silyl chloride, e.g., trimethylsilyl chloride, diphenylmethylsilyl chloride, or preferably tert-butyldimethylsilyl chloride) in presence of an equimolar amount of an organic base (such as diisopropylethylamine, triethylamine, or imidazole). The reaction takes place at −20° to 35° C. (preferably at 25° C.) for 1 to 24 hours (preferably 16 hours) to give the corresponding compound of Formula 102 (where F is the protecting group).

Preparation of Formula 103

As illustrated in Reaction Scheme I, Step 2, the side chain double bond of a protected mycophenolic acid lower alkyl ester is ozonized to yield an aldehyde.

A stream of ozonized oxygen is passed through a solution of a protected compound of Formula 102 in a solvent (such as an alcohol, a halocarbon, or preferably a mixture of methanol and dichloromethane). The reaction takes place at −100° to −40° C. (preferably at −80° C.), and continues until the presence of excess ozone is detected by the development of a blue color. The intermediate hydroperoxide thus formed is reduced without further purification, by the addition of a reducing agent (such as zinc and acetic acid, dimethyl sulfide, or preferably thiourea). The reaction takes place at −80° C. to 25° C. (preferably 0° C.) over a period of 12 to 24 hours (preferably 16 hours), to give the corresponding aldehyde of Formula 103.

Preparation of Formula 104

As illustrated in Reaction Scheme I, Step 3, the aldehyde is converted to a carbinol by addition of an organometallic compound of Formula 103a [where M is MgBr or lithium, preferably MgBr (a Grignard reagent); $Z^1$ is H, lower alkyl or $CF_3$, and $Z^2$ is H or lower alkyl].

An organolithium reagent is formed by reaction of a halovinyl (preferably bromovinyl) compound of Formula 103a (where M is halo) with an alkyllithium (preferably n-butyllithium) in an ethereal solvent (such as ether, or preferably tetrahydrofuran). The reaction takes place at −100° to 0° C. (preferably −40° C.) over a period of 0.5 to 5 hours (preferably 1 hour).

Alternatively the halovinyl compound of Formula 103a is reacted with magnesium metal in an ethereal solvent (such as ether or preferably tetrahydrofuran). The reaction takes place at 30° to 60° C. (preferably 40° C.) over a period of 1 to 6 hours (preferably 2 hours).

The organometallic compound of Formula 103a where M is zinc or cadmium may be prepared by reaction of 103a where M is Li or MgBr with a zinc or cadmium halide, preferably chloride. The compound of Formula 103a where M is tin may be prepared by reaction of 103a where M is Li or MgBr with a trialkyl chlorostannane, preferably tributyltin chloride. The compound of Formula 103a where M is tin may also be prepared by reaction of 103a where M is trifluoromethanesulfonate by reaction with a compound of formula $(R_3Sn)_2$, where R is alkyl, preferably methyl, in the presence of a palladium catalyst, preferably tetrakis (triphenylphosphine) palladium. The compound of Formula 103a where M is trifluoromethanesulfonate may be prepared from a ketone of the formula:

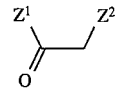

by reaction with a strong base (such as sodium hydride or potassium hexamethyldisilazide), followed by reaction of the anion thus produced with trifluoromethanesulfonic anhydride. Alternatively, the compound of Formula 103a where M is tin may be prepared by reacting a trialkyl tin hydride (preferably tributyl tin hydride) with an acetylene of the formula $Z^1$-C≡C-$Z^2$.

One molar equivalent of the resultant organometallic reagent is added to a solution of an aldehyde of Formula 103 (in the same solvent system used to make the organometallic reagent). The reaction takes place at −80° to 20° C. (preferably 0° C.) over a period of 5 to 60 minutes (preferably 10 minutes) to give the corresponding carbinol of Formula 104.

Preparation of Formula 105

As illustrated in Reaction Scheme I, Step 4, an alkyl ester of Formula 105 is formed by a Claisen ortho ester rearrangement reaction of a carbinol of Formula 104 and an orthoester of Formula 104a (where $Z^3$ is H, halo, lower alkyl, lower alkenyl, phenyl, alkoxy or -thio lower alkyl; and $Z^4$ is H or lower alkyl; or $Z^3$ and $Z^4$ taken together with the carbon to which they are attached form cycloalkyl).

A carbinol of Formula 104 is heated at 50° to 140° C. (preferably about 130° C.) with about 10 molar equivalents of an orthoester of Formula 104a, in the presence of from 0.05 to 0.25 molar equivalents (preferably 0.10 molar equivalents) of an organic acid catalyst (such as propionic, butyric, or preferably trimethylacetic acid). The reaction takes place over a period of 1 to 48 hours (preferably 3 hours) to give the corresponding alkyl ester of Formula 105.

Preparation of Formula 1A

Compounds of Formula 1A are prepared as esters by deprotection of compounds of Formula 105 as described below with reference to Reaction Scheme X, Step 1; they are hydrolyzed to the corresponding carboxylic acid as described below with reference to Reaction Scheme X, Step 2.

Preparation of Enantiomers of Formula 1A where $Z^2$ is Lower Alkyl

One method of preparing individual enantiomers of compounds of Formula 1A is from chiral compounds of Formula 104b, the preparation of which is shown below in Reaction Scheme II.

REACTION SCHEME II

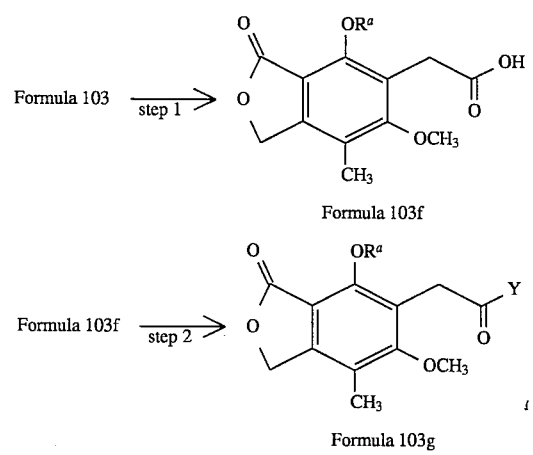

where Y is chloro or bromo.

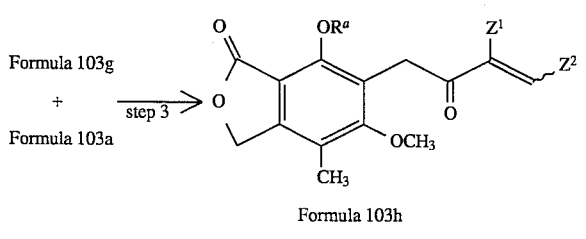

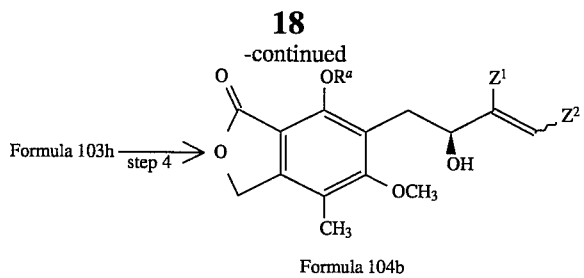

Formula 104b

Preparation of Formula 103f

As illustrated in Reaction Scheme II, Step 1, an aldehyde of Formula is oxidized to the corresponding carboxylic acid of Formula 103f.

An aldehyde of Formula 103 is reacted with about two molar equivalents of an oxidizing agent (for example, chromic acid, silver oxide, bleach, or preferably sodium periodate), in an inert solvent (such as toluene, or preferably ethyl acetate), in the presence of water and a catalytic amount (for example, about 0.01 molar equivalents) of a catalyst (such as ruthenium oxide, or preferably ruthenium trichloride). The reaction takes place at 0° to t0° C. (preferably 25° C.) for 30 minutes to 8 hours (preferably 2 hours), to give the corresponding carboxylic acid of Formula 103f.

Preparation of Formula 103g

As illustrated in Reaction Scheme II, Step 2, a carboxylic acid of Formula 103f is converted to the corresponding acyl halide of Formula 103g.

A carboxylic acid of Formula 103f is reacted with about one molar equivalent, preferably 1.1 molar equivalents, of an halogenating agent (for example, thionyl chloride, thionyl bromide, or preferably oxalyl chloride), in an inert solvent (such as dichloromethane, or preferably ethyl acetate), in the presence of a catalytic amount (for example, about 0.05 molar equivalents) of dimethylformamide. The reaction takes place at 0° to 40° C. (preferably 25° C.) for 30 minutes to 8 hours (preferably 2 hours), to give the corresponding acyl halide of Formula 103g.

Preparation of Formula 103h

As illustrated in Reaction Scheme II, Step 3, an acyl halide of Formula 103g is converted to the corresponding keto olefin of Formula 103h by addition of an organometallic compound of Formula 103a.

An acyl halide of Formula 103g is reacted with about one molar equivalent of a organometallic compound of Formula 103a (where M is cadmium, zinc, tin, or the like, prepared as shown in the preparation of compounds of Formula 104), in an inert solvent (such as dichloromethane, ether, or preferably tetrahydrofuran), optionally in the presence of a catalytic amount (for example, about 0.05 molar equivalents) of a palladium catalyst [preferably tetrakis(triphenylphosphine)palladium]. The reaction takes place at −10° to 20° C. (preferably 0° C.) for 30 minutes to 8 hours (preferably 4 hours), to give the corresponding keto olefin of Formula 103h.

Preparation of Formula 104b

As illustrated in Reaction Scheme II, Step 4, a keto olefin of Formula 103h is reduced stereospecifically to the corresponding carbinol of Formula 104b by reduction with borane methyl sulfide in the presence of a catalytic amount of (R)-tetrahydro-1-methyl-3,3-diphenyl-1H,3H-pyrrolo-[1,2-c][1,3,2]oxazaborole.

A keto olefin of Formula 103h is sterospecifically reduced with about one molar equivalent of borane methyl sulfide in the presence of a catalytic amount (0.05–0.3 molar equivalents) of (R)-tetrahydro-1-methyl- 3,3-diphenyl-1H,3H-pyrrolo-[1,2-c] [1,3,2]oxazaborole in an inert solvent (preferably a mixture of toluene and dichloromethane). The reaction takes place at −30° to 40° C. (preferably −20° C.) for 1–24 hours (preferably 12 hours), to give the corresponding carbinol of Formula 104b.

Preparation of Enantiomers of Compounds of Formula 1A

The chiral carbinol of Formula 104b is then converted to an enantiomer of a compound of Formula 1A in the same manner as shown above in Reaction Scheme I (conversion of compounds of Formula 104 to 105 to 1A).

Preparation of Compounds of Formula 1A where $Z^3$ is Lower Alkoxy

Compounds of Formula 1A where $Z^2$ is lower alkoxy are prepared from the corresponding hydroxy compounds as shown below in Reaction Scheme III.

REACTION SCHEME III

Formula 103

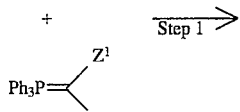

Formula 103b

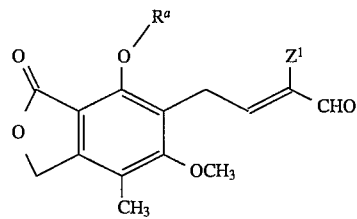

Formula 106

Formula 106

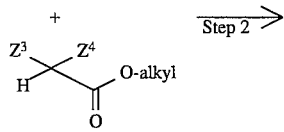

Formula 106a

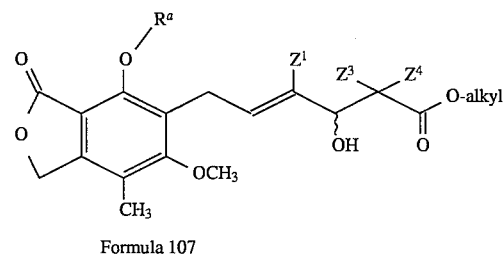

Formula 107

Preparation of Formula 106

As illustrated in Reaction Scheme III, Step 1, an aldehyde of Formula 103 is transformed into an unsaturated aldehyde of Formula 106 by a Wittig reaction with an ylid of Formula 103b (where $Z^1$ is H or lower alkyl).

An aldehyde of Formula 103 is reacted with one molar equivalent of an ylid of Formula 103b, in an organic solvent (such as dichloromethane, dimethylformamide or preferably toluene). The reaction takes place at 0° to 110° C. (preferably 80° C.) for 1 to 24 hours (preferably 8 hours) to give the corresponding unsaturated aldehyde of Formula 106.

Preparation of Formula 107

As illustrated in Reaction Scheme III, Step 2, an unsaturated aldehyde of Formula 106 is condensed with the anion of an ester of Formula 106a (where $Z^5$ is H, lower alkyl, lower alkenyl, or phenyl and $Z^4$ is H, lower alkyl, or phenyl) to give a beta-hydroxy ester of Formula 107.

An ester of Formula 106a is converted to an alkali metal salt by reacting a solution of the ester in an ethereal solvent (such as ether or preferably tetrahydrofuran) with an equimolar amount of an alkali metal hydride, hexamethyldisilazide or amide (preferably lithium diisopropylamide) at a temperature of –100° to 0° C. (preferably –80° C.), for minutes to 2 hours (preferably 30 minutes) to give a solution of the corresponding ester anion. The ester anion solution (1.0 to 1.5 molar equivalents, preferably 1.0 molar equivalents) is added to a solution of an unsaturated aldehyde of Formula 106 in the same ethereal solvent. The condensation reaction takes place at a temperature of –100° C. to 0° C. (preferably –80° C.) for 1 to 6 hours (preferably 2 hours) to give the corresponding beta-hydroxy ester of Formula 107.

Preparation of Compounds of Formula 1A where $Z^2$ is Lower Alkoxy

Compounds of Formula 1A where $Z^2$ is lower alkoxy are prepared from compounds of Formula 107 as shown below in Reaction Scheme IV.

REACTION SCHEME IV

Formula 107

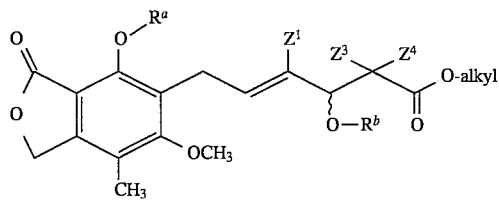

Formula 108

Preparation of Formula 108

As illustrated in Reaction Scheme IV, Step 1, the beta-hydroxy group of an ester of Formula 107 is O-alkylated to give the corresponding beta-alkoxy ester ($R^b$) of Formula 108.

An ester of Formula 107 is reacted with 1 to 3 (preferably 1.5) molar equivalents of an alkyl halide (preferably an alkyl iodide, such as methyl iodide or n-butyl iodide, preferably methyl iodide) and 1 to 3 (preferably 1.25) molar equivalents of silver oxide, in a polar organic solvent (such as dioxane, dimethylformamide or preferably acetonitrile). The reaction takes place at 25° to 100° C. (preferably 70° C.) for 1 to 24 hours (preferably 4 hours) to give the corresponding beta-alkoxy ester of Formula 108.

Preparation of Compounds of Formula 1A where $Z^4$ is Hydroxy

Compounds of Formula 1A where $Z^4$ is hydroxy are prepared as shown below in Reaction Scheme V.

REACTION SCHEME V

Formula 105

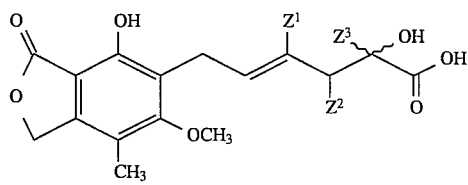

Formula 1A

Preparation of Formula 1A where $Z^4$ is Hydroxy

As illustrated in Reaction Scheme V, Step 1, an alpha-halo alkyl ester of Formula 105 (where $Z^1$ is H, lower alkyl or $CF_3$, $Z^2$ is H or lower alkyl, $Z^3$ is H, lower alkyl, lower alkenyl, or phenyl, and $Z^4$ is halo) is converted to an alpha-hydroxy acid of Formula 1A where $Z^4$ is hydroxy. The reaction takes place by hydrolysis of an alpha-alkanoyloxy ester intermediate, formed by displacement of the alpha-halo group with an alkali metal alkanoate.

An alpha-halo (preferably chloro) ester of Formula 105 is reacted with 1 to 5 (preferably 3) molar equivalents of an alkali metal alkanoate (the metal preferably potassium and the alkanoate preferably acetate) in a polar organic solvent (such as acetonitrile or preferably dimethylformamide) The reaction takes place at 40 to 100° C. (preferably 75° C.) for 1 to 24 hours (preferably 12 hours) to give the corresponding alpha-alkanoyloxy ester intermediate (not shown), which is employed without isolation or further purification.

The alpha-alkanoyloxy ester is then subjected to basic hydrolysis by reaction with 1 to 5 (preferably 2) molar equivalents of an alkali metal hydroxide (preferably sodium hydroxide) in a mixture of water and an organic solvent (such as methanol, dimethoxyethane or preferably tetrahydrofuran). The reaction takes place at 0° to 60° C. (preferably 40° C.) for 1 to 12 hours (preferably 4 hours), to afford the corresponding alpha-hydroxy acid of Formula 1A. As illustrated in Reaction Scheme V, when $R^a$ of Formula 105 is a silyl protecting group, the hydrolysis conditions are also effective for deprotection to restore the phenolic hydroxyl group. Alternatively, for example when $R^a$ is methoxymethylethyl, the deprotection and hydrolysis procedures described with reference to Reaction Scheme X, can be employed.

Preparation of Chiral Compounds of Formula 1A

One method of preparing chiral compounds of Formula 1A is shown below in Reaction Scheme VI.

REACTION SCHEME VI

Formula 106 $\xrightarrow{\text{Step 1}}$

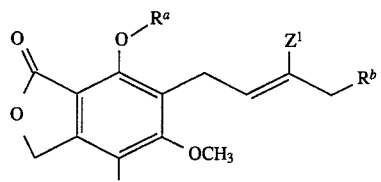

Formula 109

+ $\xrightarrow{\text{Step 2}}$

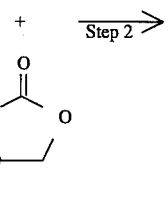

Formula 109a

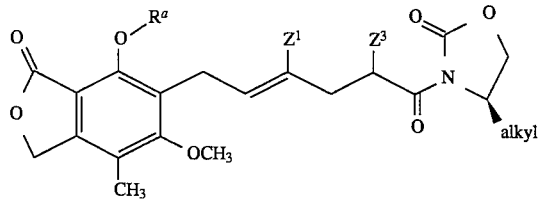

Formula 110

Formula 110 $\xrightarrow{\text{Step 3}}$

-continued
REACTION SCHEME VI

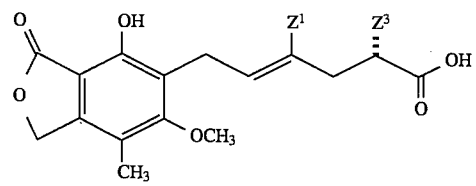

Formula 1A

Preparation of Formula 109

As illustrated in Reaction Scheme VI, Step 1, an unsaturated aldehyde of Formula 106 is reduced and then converted to the corresponding compound of Formula 109 in which $R^b$ is a leaving group (a sulfonate or halide, preferably a bromide).

An unsaturated aldehyde of Formula 106 is reacted with from 0.5 to 2 (preferably 1) molar equivalents of a reducing agent (such as sodium cyanoborohydride or preferably sodium borohydride) in an alcoholic solvent (such as ethanol, isopropanol or preferably methanol). The reaction takes place at 0° to 50° C. (preferably 25° C.) for 1 to 12 hours (preferably 2 hours) to give the corresponding allylic alcohol (not shown) which is used without isolation or further purification.

The allylic alcohol is reacted with from 1 to 1.5 (preferably 1.25) molar equivalents of a sulfonating agent (such as p-toluenesulfonyl chloride) and an organic base, or preferably reacted with a halogenating reagent (such as carbon tetrachloride/triphenylphosphine or preferably N-bromosuccinimide/triphenylphosphine) in an inert organic solvent (such as ether or preferably dichloromethane). The reaction takes place at a temperature of −40° to 40° C. (preferably −10° C.) for 1 to 12 hours (preferably 2 hours) to afford the corresponding compound of Formula 109.

Preparation of Formula 110

As illustrated in Reaction Scheme VI, Step 2, an allylic halide or sulfonate of Formula 109 is alkylated with a chiral 4-alkyl N-acyl oxazolidinone of Formula 109a to give the corresponding chiral substituted acyl oxazolidinone of Formula 110.

An alkali metal (preferably lithium) salt of a chiral 4-alkyl N-acyl oxazolidinone of Formula 109a (the alkyl group preferably being 4-isopropyl) by reaction of the N-acyl oxazolidinone with 1 to 1.25 (preferably 1.05) molar equivalents of an alkali metal hydride, hexamethyldisilazide or dialkylamide (preferably lithium diisopropylamide) in an inert organic solvent (such as ether or preferably tetrahydrofuran). The reaction takes place at −100° to −20° C. (preferably −80° C.) for 5 to 120 minutes (preferably 30 minutes). The solution of the salt (1 to 1.5, preferably 1.25 molar equivalents) is then added to a solution of an allylic compound of Formula 109 in the same solvent. The alkylation reaction takes place at −100° to 0° C. (preferably −80° C.) for 30 minutes to 6 hours (preferably 1 hour) to afford the corresponding chiral substituted acyl oxazolidinone of Formula 110.

Preparation of Chiral Formula 1A

As illustrated in Reaction Scheme VI, Step 3, a chiral substituted acyl oxazolidinone of Formula 110 is hydrolyzed to the corresponding chiral acid of Formula 1A. Use of an acyl oxazolidinone of Formula 109a having a 4-alkyl substituent of the opposite configuration in Reaction Scheme VI, Step 2, followed by hydrolysis as described in Step 3 results in the corresponding chiral acid where $Z^3$ has the opposite configuration.

An acyl oxazolidinone of Formula 110 is reacted with from 1.25 to 3.5 (preferably 3.0) molar equivalents of lithium hydroxide, in a mixture of water and a water-miscible organic solvent (such as dioxane or preferably tetrahydrofuran) containing from 6 to 10 (preferably 8) molar equivalents of 30% aqueous hydrogen peroxide. The reaction takes place at −20° to 40° C. (preferably 20° C.) for 1 to 24 hours (preferably 12 hours) to afford the corresponding chiral acid of Formula 1A.

Alternative Preparation of Compounds of Formula 1A

An alternative preparation of compounds of Formula 1A is shown below in Reaction Scheme VII.

REACTION SCHEME VII

Formula 109
+

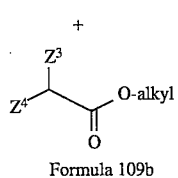

Formula 109b

Step 1 →

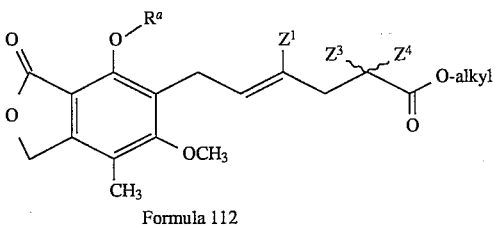

Formula 112

Preparation of Formula 112

As illustrated in Reaction Scheme VII, Step 1, an allylic compound of Formula 109 in which $R^b$ is a leaving group (a sulfonate or halide, preferably a bromide) is condensed with an ester of Formula 109b to give the mono-or di-alkyl ester of Formula 112 (where $Z^3$ is H, lower alkyl, lower alkenyl, or phenyl and $Z^4$ is H, lower alkyl, or phenyl).

An ester of Formula 109b is converted to an alkali metal salt by reaction with 1.05 to 1.25 (preferably 1.1) molar equivalents of an alkali metal amide (such as sodium hexamethyldisilazide, potassium tetramethylpiperidide or preferably lithium diisopropylamide) in an organic solvent (such as ether, dioxane or preferably tetrahydrofuran). The reaction takes place at −40° to 30° C. (preferably 0° C.) for 15 minutes to 3 hours (preferably 30 minutes). Without isolation or further purification, the resulting solution of the alkali metal salt of the ester of Formula 109b (1.2 to 1.6, preferably about 1.3 molar equivalents) is then reacted with an allylic compound of Formula 109, in the same solvent, optionally in the presence of from 2% to 10% (preferably about 5%) by volume of hexamethyl phosphoric triamide. The reaction takes place at −100° to −40° C. (preferably −80° C.) for 30 minutes to 6 hours (preferably 1 hour) to afford the corresponding alkyl ester of Formula 112.

Preparation of Formula 1A

Compound of Formula 1A are then obtained as esters by deprotection of compounds of Formula 105 as described below with reference to Reaction Scheme X, Step 1; they are hydrolyzed to the corresponding carboxylic acid as described below with reference to Reaction Scheme X, Step 2.

Preparation of Compounds of Formula 1A where $Z^3$ is $S(O)_m$alkyl

Compounds of Formula 1A where $Z^3$ is $S(O)_m$alkyl are prepared as shown below in Reaction Scheme VIII.

REACTION SCHEME VIII

Formula 1A where $Z^3$ is thioalkyl →

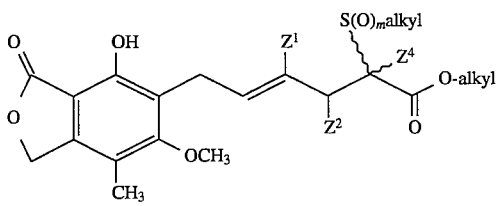

Formula 1A where $Z^3$ is $S(O)_m$alkyl

Preparation of Formula 1A where $Z^2$ is $S(O)_m$alkyl

As illustrated in Reaction Scheme VIII, Step 1, a 2-(alkylthio)-4-hexenoic acid ester of Formula 1A (where $Z^3$ is S-lower alkyl, and $Z^4$ is H or lower alkyl) is oxidized to give the corresponding 2-(alkylsulfinyl)- or 2-(alkylsulfonyl)-4-hexenoic acid ester of Formula 1A where $Z^3$ is S(O)lower alkyl or $S(O)_2$lower alkyl. Alternatively, the reaction can be performed with an acid of Formula 1A where $Z^3$ is S-lower alkyl, to give the corresponding acid where $Z^3$ is 2-(alkylsulfinyl) or 2-(alkylsulfonyl).

An alkylthio-4-hexenoic acid ester of Formula 1A is reacted with 1.0 to 1.25 (preferably 1.05) molar equivalents of an oxidizing agent (such as oxone®) optionally in the presence of an inert support (such as alumina), in a solvent (such as chloroform or preferably dichloromethane). The reaction takes place at 0° to 55° C. (preferably 35° C.) for 1 to 10 hours (preferably 2 hours) to afford the corresponding 2-(alkylsulfinyl)-4-hexenoic acid ester of Formula 1A where $Z^3$ is S(O)lower alkyl.

By repeating the foregoing procedure under the same conditions starting with the 2-(alkylsulfinyl)-4-hexenoic acid ester so-produced], or by conducting the reaction with the 2-(alkylthio)-4-hexenoic acid ester starting material [and using 2.0 to 2.5 (preferably 2.25) molar equivalents of oxone] the corresponding 2-alkylsulfonyl-4-hexenoic acid esters are produced.

A 2-(alkylsulfinyl)-or 2-(alkylsulfonyl)-4-hexenoic acid ester of Formula I-ZA-K is hydrolyzed to give the corresponding acid as described with reference to Reaction Scheme X, Step 2.

Preparation of Compounds of Formula ZA where $Z^1$ is Halo

Compounds of Formula 1A where $Z^1$ is halo are prepared as shown below in Reaction Scheme IX.

REACTION SCHEME IX

Formula 103
+

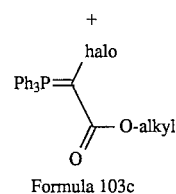

Step 1 →

Formula 103c

-continued
REACTION SCHEME IX

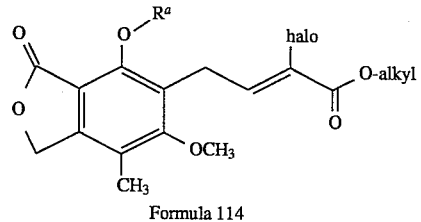

Formula 114

Formula 114 $\xrightarrow{\text{Step 2}}$

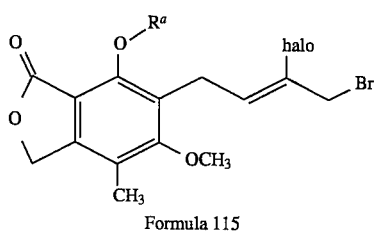

Formula 115

Formula 115
+
Z⁴CH(CO₂Et)₂
Formula 106b
$\xrightarrow{\text{Step 3}}$

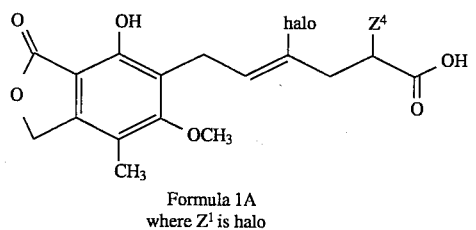

Formula 1A
where Z¹ is halo

Preparation of Formula 114

As illustrated in Reaction Scheme IX, Step 1, a protected aldehyde of Formula 103 and a triphenylphosphoranylideneacetate of Formula 103c are combined in a Wittig reaction to give the corresponding alkyl-2-halobutenoate ester of Formula 114.

An aldehyde of Formula 103 is reacted with 1.0 to 1.5 (preferably 1.1) molar equivalents of an alkyl 2-halo-2-triphenylphosphoranylidene-acetate of Formula 103c (the halo group preferably being chloro) in an organic solvent (such as acetonitrile, or preferably toluene). The reaction takes place at 50° to 120° C. (preferably 110° C.) for 4 to 48 hours (preferably 24 hours) to afford the corresponding alkyl 2-halo-4-aryl-2-butenoate ester of Formula 114.

Preparation of Formula 115

As illustrated in Reaction Scheme IX, Step 2, a protected alkyl 2-halo- 4-aryl-2-butenoate ester of Formula 114 is converted to the corresponding bromide of Formula 115 after reduction to the corresponding alcohol (not shown).

A 2-halo-4-aryl-2-butenoate ester of Formula 114 (preferably a t-butyl ester) is converted to the corresponding acid (preferably by dissolution in trifluoroacetic acid at room temperature for 1 to 2 hours). The acid is isolated and purified by conventional means, then reacted with 0.5 to 3 (preferably 1.6) molar equivalents of a reducing agent (such as sodium cyanoborohydride, sodium borohydride, or preferably borane dimethyl disulfide complex) in an inert solvent (such as methanol, ethanol, isopropanol or preferably THF). The reaction takes place at 0° to 50° C. (preferably 25° C.) for 1 to 48 hours (preferably 24 hours) to give the corresponding alcohol (not shown) which is used after purification.

The allylic alcohol so-produced is reacted with from 1 to 1.5 (preferably 1.25) molar equivalents of a sulfonating agent (such as p-toluenesulfonyl chloride) and an organic base, or preferably reacted with a halogenating reagent (such as carbon tetrachloride/triphenylphosphine or preferably N-bromosuccinimide/triphenylphosphine) in an inert organic solvent (such as ether or preferably dichloromethane). The reaction takes place at a temperature of −40° to 40° C. (preferably −10° C.) for 1 to 12 hours (preferably 2 hours) to afford the corresponding 2-halo-4-aryl-2-butenyl bromide compound of Formula 115.

Preparation of Formula 1A where Z¹ is Halo

As illustrated in Reaction Scheme IX, Step 3, a protected 2-halo-4-aryl- 2-butenyl bromide compound of Formula 115 is condensed with a dialkyl malonate of Formula 106b (substituted by Z⁴ where Z⁴ is hydrogen, lower alkyl, or phenyl), which is hydrolysed and decarboxylated to give the corresponding 4-halo-4-hexenoic acid derivative of Formula 1A where Z¹ is halo.

A malonic ester of Formula 106b (where Z⁴ is H, lower alkyl, or phenyl) is converted to an alkali metal salt by reaction with 1.05 to 1.25 (preferably 1.1) molar equivalents of an alkali metal hydride (preferably sodium hydride) in an organic solvent (such as ether, dioxane or preferably tetrahydrofuran). The reaction takes place at −40° to 30° C. (preferably 0° C.) for 15 minutes to 3 hours (preferably 30 minutes). Without isolation or further purification, the resulting solution of the alkali metal salt of the ester of Formula 106b (1.2 to 1.6, preferably about 1.3 molar equivalents) is then reacted with an allylic bromo compound of Formula 115 in the same solvent. The reaction takes place at −20 to 50° C. (preferably 25° C.) for 30 minutes to 6 hours (preferably 2 hours) to afford the corresponding dialkyl ester derivative.

The dialkyl ester thus produced is then hydrolysed conventionally, using a strong base, preferably aqueous sodium hydroxide, in a protic solvent, preferably ethanol, heating to reflux. The dicarboxylic acid thus produced is separated conventionally, and then decarboxylated by heating, preferably in a high-boiling inert solvent, most preferably 1,2-dichlorobenzene, to give the corresponding 4-halo-4-hexenoic acid derivative of Formula 1A where Z¹ is halo.

Preparation of Compounds of Formula 1A

Compounds of Formula 1A as esters and carboxylic acids are obtained by deprotection and hydrolysis as shown below in Reaction Scheme X.

REACTION SCHEME X

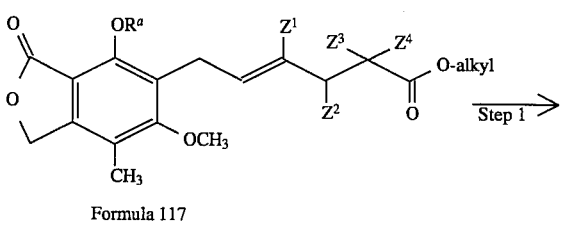

Formula 117

REACTION SCHEME X -continued

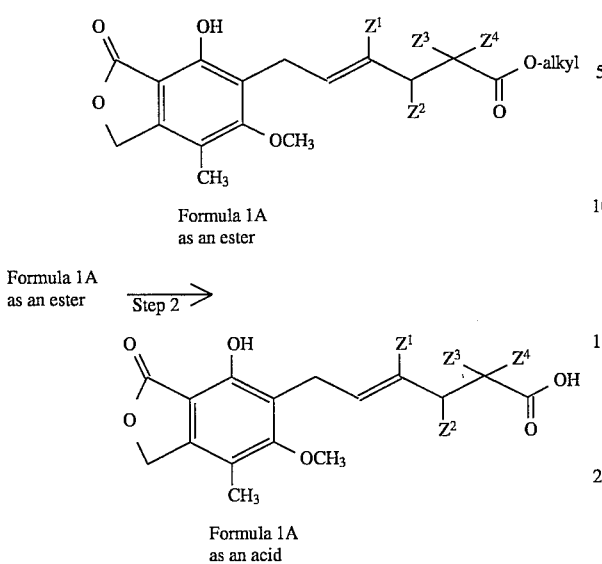

Formula 1A
as an ester

Formula 1A
as an ester $\xrightarrow{\text{Step 2}}$

Formula 1A
as an acid

Preparation of Formula 1A as an Ester

As illustrated in Reaction Scheme X, Step 1, a protected phenol of Formula 117 (which can be any of the corresponding protected compounds of Reaction Schemes I to IX, such as Formulae 105, 107, 108, 112, and the like) is deprotected to give the corresponding alkyl ester of Formula 1A as an ester.

An alkyl ester of Formula 117 (having either an acetal-type or a silyl-type protecting group) is treated with from 0.05 to 0.2 molar equivalents (preferably 0.1 molar equivalents) of an aqueous mineral acid (such as sulfuric, perchloric, or preferably hydrochloric acid), in a water-miscible organic solvent (such as methanol, acetone, or preferably ethanol). The reaction takes place at 0° to 50° C. (preferably 25° C.) over a period of 1 to 6 hours (preferably 2 hours) to give the corresponding free phenol of Formula 1A.

Alternatively, to remove acetal-type protecting groups (such as MEM) a compound of Formula 117 is treated with 0.05 to 0.25 molar equivalents (preferably 0.1 molar equivalents) of a Lewis acid (such as zinc chloride or preferably zinc bromide), in a solvent (such as benzene, chloroform, or preferably dichloromethane). The reaction takes place at 0° to 50° C. (preferably 25° C.) over a period of 1 to 12 hours (preferably 3 hours) to give the corresponding free phenol of Formula 1A.

Alternatively, to remove silyl-type protecting groups (such as t-butyldimethylsilyl) a compound of Formula 117 is reacted with 1.0 to 1.5 (preferably 1.25) moles of a tetraalkyl ammonium fluoride (preferably tetrabutylammonium fluoride) in an ethereal solvent (such as dioxane or preferably tetrahydrofuran). The reaction takes place at −10 to 25° C. (preferably 0° C.) over a period of 0.1 to 2 hours (preferably 0.5 hours) to give the corresponding free phenol of Formula 1A.

Preparation of Formula 1A as a Carboxylic Acid

As illustrated in Reaction Scheme X, Step 2, a compound of Formula 1A as an ester (prepared as described above) is hydrolyzed to give the corresponding acid of Formula 1A as a carboxylic acid.

An alkyl ester of Formula 1A is reacted with from 1.5 to 4 molar equivalents (preferably 2 molar equivalents) of an inorganic hydroxide (such as potassium, sodium, or preferably lithium hydroxide) in a mixture of water and an organic solvent (such as tetrahydrofuran, methanol, or preferably dimethoxyethane). The reaction takes place at 0° to 60° C. (preferably 40° C.) over a period of 1 to 12 hours (preferably 3 hours). The resulting anion is acidified with an aqueous mineral acid (such as hydrochloric acid). The acidification takes place at 0° to 40° C. (preferably 25° C.) over a period of 1 to 10 minutes (preferably 2 minutes) to give the corresponding carboxylic acid of Formula 1A.

Preparation of Compounds of Formula 1B

One method of preparing compounds of Formula i where Z is a sidechain of Formula ZB, illustrated as compounds of Formula 1B, is shown below in Reaction Schemes XI and XII.

REACTION SCHEME XI

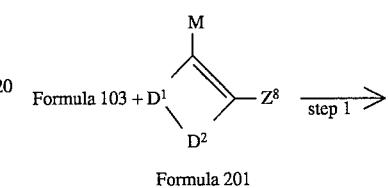

Formula 201

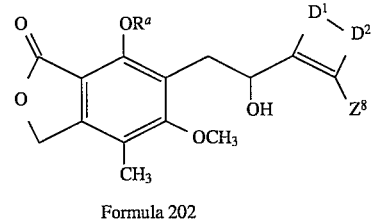

Formula 202 where M is Li or MgBr.

Formula 202 $\xrightarrow{\text{step 2}}$

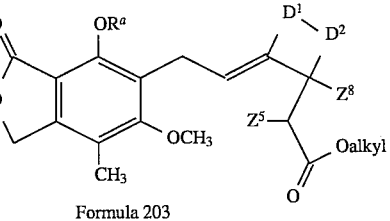

Formula 203

Formula 203 $\xrightarrow{\text{step 3}}$

Formula 1B

Preparation of Formula 202

As illustrated in Reaction Scheme XI, Step 1, the aldehyde of Formula 103 is converted to a carbinol of Formula 202 by addition of an unsaturated cyclic organometallic compound of Formula 201 where M is Li or MgBr, prepared for example as described above with reference to Reaction Scheme I, Step 3.

One molar equivalent of the organometallic reagent 201 is added to a solution of an aldehyde of Formula 103 (in the same solvent system used to make the organometallic reagent). The reaction takes place at −80° to −20° C. (preferably −40° C.) over a period of 5 to 60 minutes (preferably 15 minutes) to give the corresponding carbinol of Formula 202.

Resolution of Formula 202

The racemic compound of Formula 202 may be separated into its two enantiomers by conventional means, for example by conversion into two diastereoisomers that are then separated by crystallization, chromatography, or by any conventional separation technique. Preferably, the carbinol is reacted with a chiral isocyanate to give a mixture of diastereoisomeric carbamates, which are separated by chromatography and cleaved to give the pure enantiomers.

A carbinol of Formula 202 is heated at 30° to 100° C. (preferably about 60° C.) with 2 to 6 molar equivalents (preferably 4 molar equivalents) of a chiral isocyanate in the presence of 1 to 1.5 molar equivalents (preferably 1.2 molar equivalents) of a strong organic base, for example 4-dimethylaminopyridine, in a hindered tertiary amine (for example diisopropylethylamine) as a solvent. The reaction takes place over a period of 1 to 24 hours (preferably 7 hours) to give the corresponding carbamate as a mixture of diastereoisomers.

The mixture of diastereoisomeric carbamates is separated by conventional means, preferably chromatography. The individual diastereoisomers are then separately cleaved by treatment with 1 to 1.5 molar equivalents (preferably 1.2 molar equivalents) of a trihalosilane, for example trichlorosilane, in the presence of an excess of a tertiary amine, for example triethylamine, in an inert solvent, for example toluene. The reaction takes place at a temperature of 90°–120° C. (preferably 110° C.) over a period of 5 minutes to 2 hours (preferably 15 minutes) to give the corresponding enantiomer of the carbinol of Formula 202.

Preparation of Formula 203

As illustrated in Reaction Scheme XI, Step 2, an alkyl ester of Formula 203 is formed by a Claisen ortho ester reaction of a carbinol of Formula 201 (or an enantiomer thereof) with an appropriately substituted orthoester.

A carbinol of Formula 202 is heated at 50° to 140° C. (preferably 130° C.) with a large excess of an orthoester of Formula 104a (see Reaction Scheme I, step 4), in the presence of from 0.05 to 0.25 molar equivalents (preferably 0.10 molar equivalents) of an organic acid catalyst (such as propionic, butyric, or trimethylacetic acid, preferably trimethylacetic acid). The reaction takes place over a period of 1 to 24 hours (preferably 2.5 hours) to give the corresponding alkyl ester of Formula 203.

Preparation of Formula 1B

Compounds of Formula 1B are prepared as described with reference to Reaction Scheme X, Step 1 (deprotection to afford the corresponding alkyl ester of Formula 1B), and Step 2 (hydrolysis to afford the corresponding acid of Formula 1B).

Alternative Preparation of Enantiomers of Compounds of Formula 1B

Another method of preparing individual enantiomers of compounds of Formula 1 where Z is sidechain ZB, illustrated as compounds of Formula 1B, is from chiral compounds of Formula 202b, the preparation of which is shown below in Reaction Scheme XII.

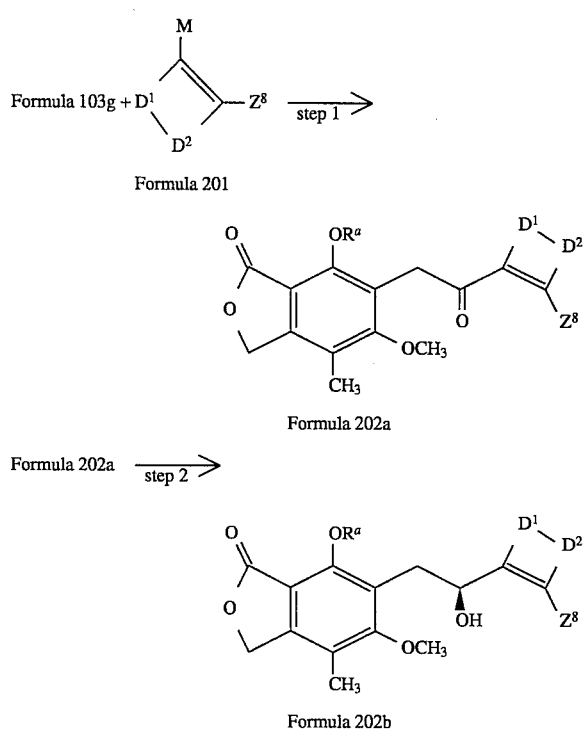

Preparation of Formula 202a

Compounds of Formula 202a are prepared as described above with reference to Reaction Scheme II, Step 3 (conversion of 103g to 103h).

Preparation of Formula 202b

Compounds of Formula 202b are prepared as described above with reference to Reaction Scheme II, Step 4 (conversion of 103h to 104b).

Preparation of Enantiomers of Compounds of Formula 1B

The chiral carbinol of Formula 202b is then converted to an enantiomer of a compound of Formula 1B in the same manner as shown above in Reaction Scheme XI (conversion of compounds of Formula 202 to 203 to 1B).

Preparation of Compounds of Formula 1C

One method of preparing compounds of Formula I where Z is a sidechain of Formula ZC, illustrated as compounds of Formula 1C, is shown below in Reaction Scheme XIII.

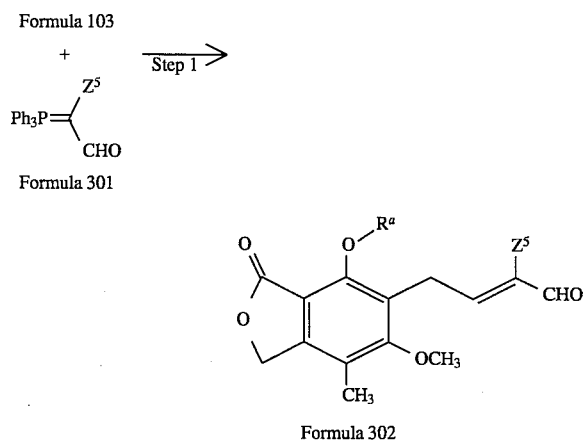

-continued
REACTION SCHEME XIII

Formula 302 $\xrightarrow{\text{Step 2}}$

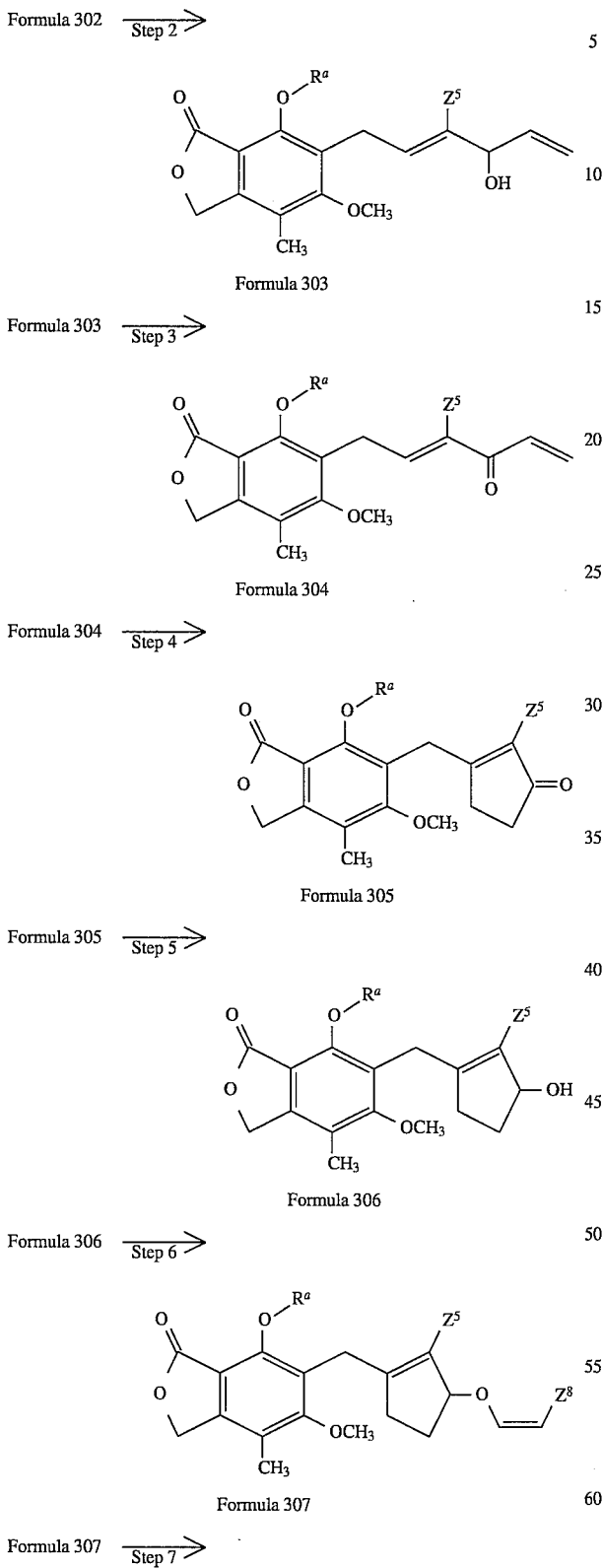

Formula 303

Formula 303 $\xrightarrow{\text{Step 3}}$

Formula 304

Formula 304 $\xrightarrow{\text{Step 4}}$

Formula 305

Formula 305 $\xrightarrow{\text{Step 5}}$

Formula 306

Formula 306 $\xrightarrow{\text{Step 6}}$

Formula 307

Formula 307 $\xrightarrow{\text{Step 7}}$

-continued
REACTION SCHEME XIII

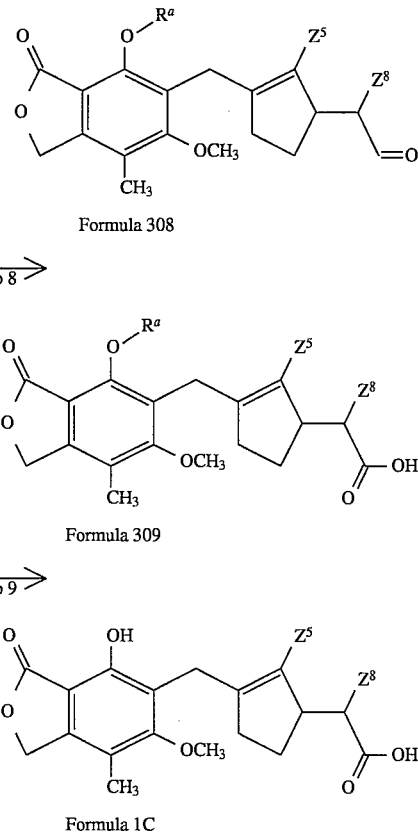

Formula 308

Formula 308 $\xrightarrow{\text{Step 8}}$

Formula 309

Formula 309 $\xrightarrow{\text{Step 9}}$

Formula 1C

Preparation of Formula 302

As illustrated in Reaction Scheme XIII, Step 1, an aldehyde of Formula 103 (prepared, for example as described above with reference to Reaction Scheme I, Steps 1 and 2) is transformed into an unsaturated aldehyde of Formula 302 by a Wittig reaction with an ylid of Formula 301 (where $Z^5$ is H or lower alkyl).

An aldehyde of Formula 103 is reacted with one molar equivalent of an ylid of Formula 301, in an organic solvent (such as dichloromethane, dimethylformamide or preferably toluene). The reaction takes place at 0° to 110° C. (preferably 80° C.) for 1 to 24 hours (preferably 8 hours) to give the corresponding unsaturated aldehyde of Formula 302.

Preparation of Formula 303

As illustrated in Reaction Scheme XIII, Step 2, an unsaturated aldehyde of Formula 302 is converted to the corresponding vinyl carbinol of Formula 303.

An aldehyde of Formula 302 is reacted with from 1.0 to 1.25 (preferably 1.1) molar equivalents of an organovinyl compound (preferably vinylmagnesium bromide) in a solvent (such as ether or preferably tetrahydrofuran). The reaction takes place at −30° to 20° C. (preferably at 0° C.) for 0.1 to 4 hours (preferably 0.5 hours) to give the corresponding vinyl carbinol of Formula 303.

Preparation of Formula 304

As illustrated in Reaction Scheme XIII, Step 3, a vinyl carbinol of Formula 303 is oxidized to give the corresponding dienone of Formula 304.

A vinyl carbinol of Formula 303 is reacted with 1.0 to 1.5 (preferably 1.1) molar equivalents of an oxidizing agent (such as manganese dioxide, pyridinium chlorochromate or preferably pyridinium dichromate) in a solvent (such as pyridine or preferably dichloromethane). The reaction takes place at 0° to 30° C. (preferably 25° C.) for 30 minutes to 4 hours (preferably 1 hour) to give the corresponding dienone of Formula 304.

Preparation of Formula 305

As illustrated in Reaction Scheme XIII, Step 4, a dienone of Formula 304 is cyclized to give the corresponding cyclopentenone of Formula 305.

A dienone of Formula 304 reacted with 0.3 to 1.5 (preferably 1.0) molar equivalents of a Lewis acid (such as boron trichloride, tin (IV) chloride or preferably boron trifluoride etherate) in a solvent (such as tetrachloroethane or preferably dichloromethane). The reaction takes place at 0° to 30° C. (preferably 25° C.) for 1 to 6 hours (preferably 2 hours) to give the corresponding cyclopentenone of Formula 305.

Preparation of Formula 306

As illustrated in Reaction Scheme XIII, Step 5, a cyclopentenone of Formula 305 is reduced to give the corresponding cyclopentenol of Formula 306.

A cyclopentenone of Formula 305 is reacted with 1.0 to 1.5 (preferably 1.1) molar equivalents of a reducing agent (such as lithium tri-tert-butoxyaluminium hydride or preferably sodium borohydride in the presence of an equimolar amount of cerium trichloride) in a mixture of an ethereal solvent (preferably tetrahydrofuran) and a lower alkanol (preferably methanol). The reaction takes place at 0° to 40° C. (preferably at 25° C.) for 1 to 6 hours (preferably 2 hours) to give the cyclopentenol of Formula 306.

Preparation of Formula 307

As illustrated in Reaction Scheme XIII, Step 6, a cyclopentenol of Formula 306 is transformed to the corresponding vinyl ether of Formula 307.

A cyclopentenol of Formula 306 is reacted with from 10 to 100 (preferably 50) molar equivalents of a 1-alkenyl ether, optionally in the presence of a co-solvent (such as ether or tetrahydrofuran), in the presence of from 0.1 to 0.5 (preferably 0.3) molar equivalents of a mercury (II) salt (preferably mercury (II) acetate). The reaction takes place at 0° to 50° C. (preferably 25° C.) for 1 to 5 days (preferably 2 days) to give the corresponding vinyl ether of Formula 307.

Preparation of Formula 308

As illustrated in Reaction Scheme XIII, Step 7, a vinyl ether of Formula 307 is rearranged to the corresponding acetaldehyde of Formula 308.

A vinyl ether of Formula 307 is reacted with from 10 to 100 (preferably 50) molar equivalents of a lithium salt (such as the tetrafluoroborate or preferably the perchlorate) in a solvent (such as tetrahydrofuran or preferably ether). The reaction takes place at 0° to 35° C. (preferably 25° C.) for 0.1 to 2 hours (preferably 0.5 hours) to give the corresponding acetaldehyde of Formula 308.

Preparation of Formula 309

As illustrated in Reaction Scheme XIII, Step 8, an acetaldehyde of Formula 308 is oxidized to give the corresponding acid of Formula 309.

An acetaldehyde of Formula 308 is reacted with 1 to 3 (preferably 1.5) molar equivalents of a suitable oxidizing agent (such as silver oxide, Jones reagent or preferably sodium chlorite) in the presence of an equimolar amount of a phenol (such as quinol or preferably resorcinol). The reaction is conducted in a mixture of water and a water-miscible organic solvent (such as tetrahydrofuran or preferably dioxane) at a pH of from 4 to 6 (preferably 5) at −10° to 25° C. (preferably 0° C.) for 10 minutes to 2 hours (preferably 30 minutes) to give the corresponding acid of Formula 309.

Preparation of Formula 1C

As illustrated in Reaction Scheme XIII, Step 9, an acid of Formula 309 is deprotected to give the corresponding acid of Formula 1C.

An acid of Formula 309 where $R^a$ is a sulphonyloxy protecting group hydrolyzed under basic conditions, using from 1 to 5 (preferably 3) molar equivalents of an alkali metal hydroxide (preferably lithium hydroxide) in a mixture of water and a water-miscible organic solvent (such as dioxane or preferably methanol). The reaction takes place at 40° to 100° C. (preferably 60° C.) for 1 to 48 hours (preferably 12 hours) to afford the corresponding cyclopentene carboxylic acid of Formula 1C.

Alternatively, for other protecting groups, the deprotection reaction takes place as described above with reference to Reaction Scheme X, Step 1.

Preparation of Compounds of Formula 1D

One method of preparing compounds of Formula 1 where Z is a sidechain of Formula ZD, illustrated as compounds of Formula 1D, is shown below in Reaction Scheme XIV.

REACTION SCHEME XIV

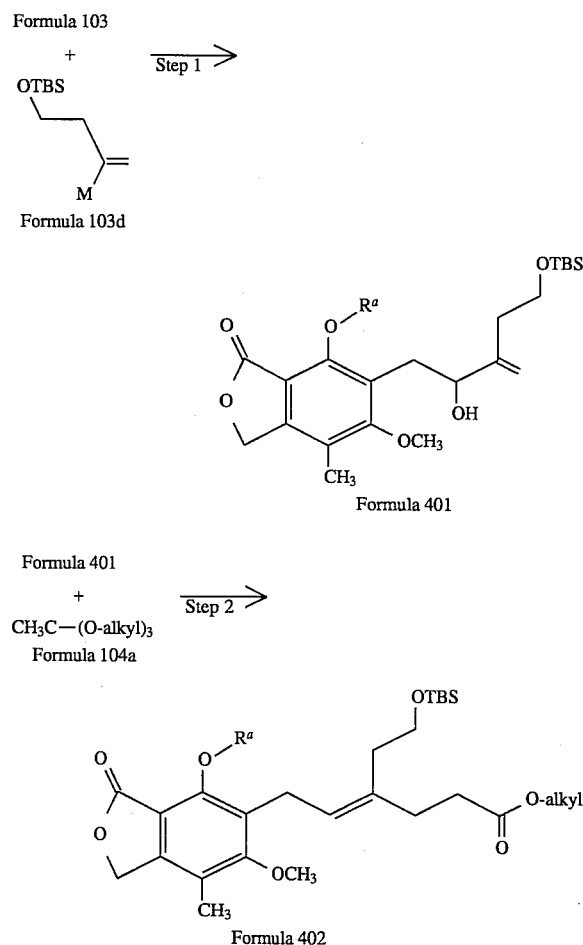

REACTION SCHEME XIV -continued

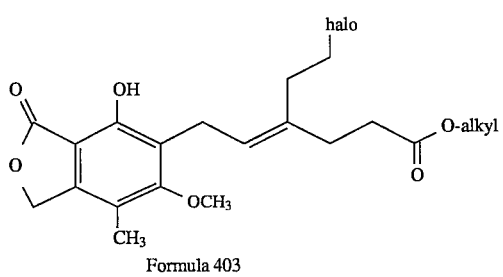

Formula 403

Formula 403 $\xrightarrow{\text{Step 4}}$

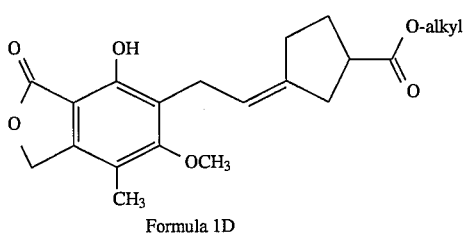

Formula 1D

Preparation of Formula 401

As illustrated in Reaction Scheme XIV, Step 1, an aldehyde of Formula 103 (where $R^a$ is a silyl protecting group) is converted to a carbinol by 40 addition of an organometallic confound of Formula 103d (such as a substituted vinyl organolithium, or preferably a Grignard reagent where: M is MgBr or Li; $Z^2$ is H or lower alkyl; and TBS is a tert-butyldimethylsilyl protecting group).

The aldehyde of Formula 103 is reacted with from 1.1 to 1.5 (preferably 1.25) molar equivalents of an organometallic, preferably organolithium, derivative of a protected 2-halo (preferably 2-bromo) but-1-en- 4-ol. The reaction is performed at from −100° to −40° C. (preferably at −78° C.) for from 30 minutes to 6 hours (preferably 1 hour) to afford the corresponding compound of Formula 401.

Preparation of Formula 402

As illustrated in Reaction Scheme XIV, Step 2, an alkyl ester of Formula 402 is formed by a Claisen ortho ester rearrangement reaction of a carbinol of Formula 401 and a trialkyl orthoacetate of Formula 104a.

A carbinol of Formula 401 is heated at 50° to 120° C. (preferably about 100° C.) with about 10 molar equivalents of an orthoester of Formula 104a, in the presence of from 0.05 to 0.25 (preferably 0.10) molar equivalents of an organic acid catalyst (such as propionic, butyric, or preferably trimethylacetic acid). The reaction takes place over a period of 1 to 48 hours (preferably 8 hours) to give the corresponding alkyl ester of Formula 402.

Preparation of Formula 403

As illustrated in Reaction Scheme XIV, Step 3, an alkyl ester of Formula 402 is reacted with a tetraalkylammonium fluoride and then halogenated to give a protected ester of Formula 403.

A compound of Formula 402 is reacted with from 2.0 to 3.0 (preferably 2.0) molar equivalents of a tetraalkylammonium (preferably tetrabutylammonium) fluoride, in a solvent (such as dioxane, tetrahydrofuran, or preferably methylene chloride) at from 0° to 25° C. (preferably 10° C.), for from 30 minutes to 4 hours (preferably 1 hour). The product so obtained is reacted with from 1.0 to 1.5 (preferably 1.25) molar equivalents of a halogenating agent (preferably a brominating agent, such as triphenylphosphine/carbon tetrabromide or preferably triphenylphosphine/N-bromosuccinimide) in a solvent such as ether or preferably dichloromethane. The reaction takes place at from −40° to 0° C. (preferably −10° C.) for from 1 to 6 hours (preferably 4 hours) to give the corresponding halogenated ester of Formula 403.

Preparation of Formula 1D

As illustrated in Reaction Scheme XIV, Step 4, a halogenated ester of Formula 403 is cyclized to give a cycloalkyl ester of Formula 1C.

A compound of Formula 403 is reacted with from 2.0 to 2.5 (preferably 2.25) molar equivalents of a strong base (such as lithium diisopropylamide, sodium hydride or preferably sodium hexamethyldisilazide) in an ethereal solvent (such as ether, dioxane or preferably tetrahydrofuran) The reaction takes place at from −100° to −60° C. (preferably −78° C.) for 1 to 12 hours (preferably 4 hours) to give the cycloalkyl ester of Formula 1D, which may be hydrolyzed to the carboxylic acid of Formula 1D as described above with reference to Reaction Scheme X, Step 2.

Preparation of Compounds of Formula 1E

Methods of preparing compounds of Formula 1 where Z is sidechain of Formula ZE, illustrated as compounds of Formula 1E, is shown below in Reaction Schemes XV to XVII.

REACTION SCHEME XV

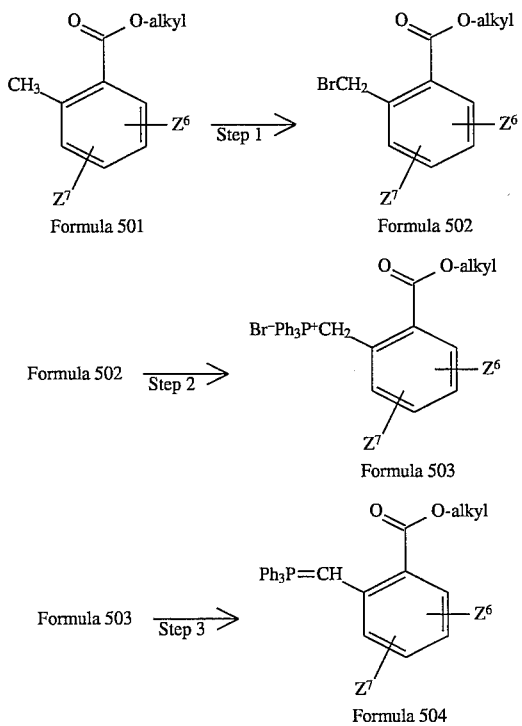

Formula 504
+
Formula 103
$\xrightarrow{\text{Step 4}}$

REACTION SCHEME XV -continued

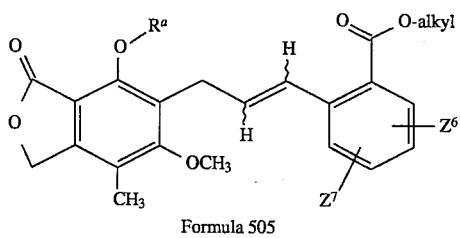

Formula 505

Formula 505 $\xrightarrow{\text{Step 5}}$

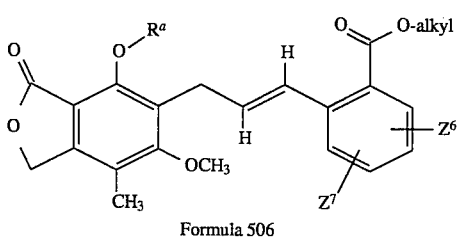

Formula 506

Preparation of Formula 502

As illustrated in Reaction Scheme XV, Step 1, the 2-methyl group of an alkyl 2-methylbenzoate of Formula 501 (where $Z^6$ and $Z^7$ are selected from H, lower alkyl, lower alkoxy, lower alkoxycarbonyl, halo and nitro) is brominated to give the corresponding compound of Formula 502.

An ester of Formula 501 is reacted with 1.0 to 1.2 (preferably 1.05) molar equivalents of a brominating agent (such as N-bromoacetamide or preferably N-bromosuccinimide), optionally in the presence of an initiator (such as visible light) or from 0.001 to 0.01 (preferably 0.005) molar equivalents of a chemical initiator (such as azobisisobutyronitrile or preferably benzoyl peroxide) in a solvent (such as ethyl formate or preferably carbon tetrachloride). The reaction takes place at 40° to 80° C. (preferably 75° C.) for 30 minutes to to 6 hours (preferably 2 hours) to afford the corresponding alkyl 2-bromomethylbenzoate of Formula 502, which can be purified by conventional means or preferably used directly for the next step.

Preparation of Formula 503

As illustrated in Reaction Scheme XV, Step 2, a 2-bromomethyl group of Formula 502 is converted to the corresponding phosphonium salt of Formula 503.

A 2-bromomethylbenzoate of Formula 502 is reacted with 1.0 to 1.25 (preferably 1.05) molar equivalents of a triaryl phosphine (preferably triphenyl phosphine) in a solvent (such as dimethylformamide or preferably acetonitrile). The reaction takes place at 25° to 90° C. (preferably 50° C.) for 1 to 24 hours (preferably 2 hours) to afford the corresponding phosphonium salt of Formula 503.

Preparation of Formula 504

As illustrated in Reaction Scheme XV, Step 3, a phosphonium salt of Formula 503 is converted to the corresponding substituted benzylidenetriphenylphosphorane ylid of Formula 504.

A phosphonium salt of Formula 503 is dissolved or suspended in a solvent (such as dioxane, ether or preferably dimethylformamide) and reacted with 1.0 to 1.25 (preferably 1.05) molar equivalents of a base (such as sodium hydride, triethylamine or preferably 1,5-diazabicyclo[4.3.0]non-5-ene). The reaction takes place at 0° to 60° C. (preferably 25° C.) for 1 to 6 hours (preferably 2 hours) to afford the corresponding ylid of Formula 504, which can be isolated by conventional means or its solution can be used directly for the next step.

Preparation of Formulae 505 and 506

As illustrated in Reaction Scheme XV, Step 4, an ylid of Formula 504 and a protected aldehyde of Formula 103 (prepared, for example, as described in connection with Reaction Scheme ZA-A, Step 2) are employed in a Wittig reaction to give the corresponding protected substituted benzoic acid alkyl ester of Formula 505 as a mixture of E and Z isomers, from which the desired E isomer of Formula 506 is isolated, as illustrated in Reaction Scheme XV, Step 5.

A solution of 0.8 to 1.0 (preferably 0.95) molar equivalents of a protected aldehyde of Formula 103 in a solvent (such as ether, dioxane or preferably dimethylformamide) is added to a solution of an ylid of Formula 504 in the same solvent. The reaction takes place at 0° to 50° C. (preferably 25° C.) for 1 to 24 hours (preferably 12 hours) to afford the corresponding protected substituted benzoic acid alkyl ester of Formula 505 as a mixture of E and Z isomers, from which the desired E-isomer of Formula 506 can be isolated by conventional means (such as distillation, chromatography or preferably fractional crystallization).

REACTION SCHEME XVI

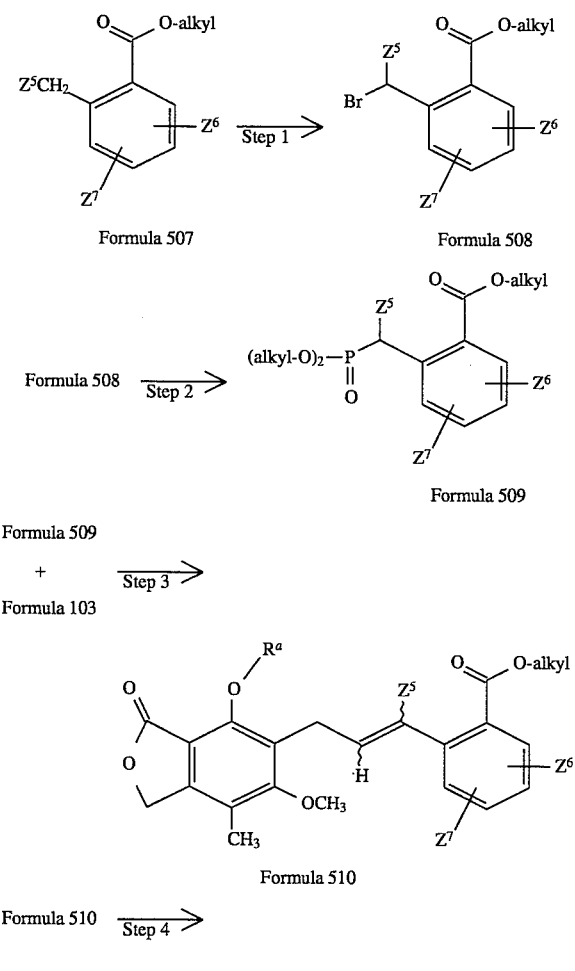

Formula 510 $\xrightarrow{\text{Step 4}}$

-continued
REACTION SCHEME XVI

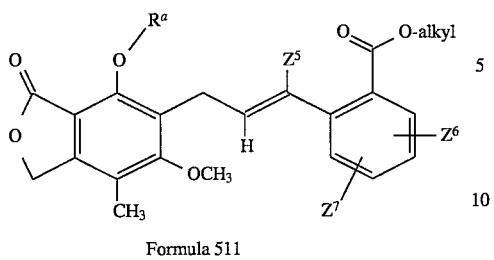

Formula 511

Preparation of Formula 508

As illustrated in Reaction Scheme XVI, Step 1, the alpha carbon of an alkyl 2-alkylbenzoate of Formula 507 (where $Z^5$ is H or lower alkyl, and $Z^6$ and $Z^7$ are selected from H, lower alkyl, lower alkoxy, lower alkoxycarbonyl, halo and nitro) is brominated to give the corresponding compound of Formula 508. The reaction takes place under the conditions described with reference to Reaction Scheme XV, Step 1.

Preparation of Formula 509

As illustrated in Reaction Scheme XVI, Step 2, an alkyl 2-bromoalkylbenzoate of Formula 508 and a trialkyl phosphite are combined in an Arbuzov reaction to give the corresponding phosphonate of Formula 509.

A compound of Formula 508 is reacted with from 5 to 20 (preferably 10) molar equivalents of a trialkyl phosphite (preferably triethyl phosphite). The reaction takes place at 100° to 200° C. (preferably 150° C.) for 1 to 24 hours (preferably 6 hours) to afford the corresponding phosphonate of Formula 509.

Preparation of Formulae 510 and 511

As illustrated in Reaction Scheme XVI, Step 3, a phosphonate of Formula 509 and a protected aldehyde of Formula 103 (prepared, for example, as described in connection with Reaction Scheme I, Step 2) are reacted to give the corresponding protected substituted benzoic acid alkyl ester of Formula 510 as a mixture of E and Z isomers, from which the desired E isomer of Formula 511 is isolated, as illustrated in Reaction Scheme XV, Step 4.

A phosphonate of Formula 509 is reacted with 1.0 to 1.5 (preferably 1.1) molar equivalents of a base such (as sodium amide, potassium tert-butoxide or preferably sodium hydride) for from 1 to 4 hours (preferably 2 hours) at 0° to 50° C. (preferably 25° C.) in a solvent (such as dioxane, dimethylformamide or preferably dimethoxyethane), to give a solution or suspension of the corresponding alkali metal salt of Formula 509, which is employed without isolation or further purification. The alkali metal salt is reacted with from 0.9 to 1.1 (preferably 1.0) molar equivalents of a protected aldehyde of Formula 103, dissolved in the same solvent. The reaction takes place at 0° to 60° C. (preferably 40° C.) for 1 to 6 hours (preferably 2 hours) to afford the corresponding protected optionally substituted benzoic acid alkyl ester of Formula 510 as a mixture of E and Z isomers, from which the desired E-isomer of Formula 511 can be isolated by conventional means (such as distillation, chromatography or preferably fractional crystallization).

REACTION SCHEME XVII

Formula 103

+

Formula 512

-continued
REACTION SCHEME XVII

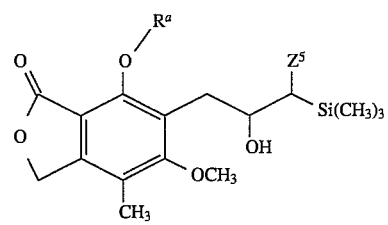

Formula 513

Formula 513 $\xrightarrow{\text{Step 2}}$

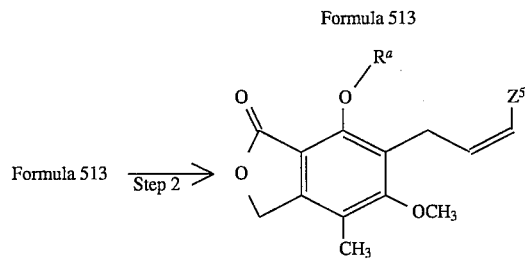

Formula 514

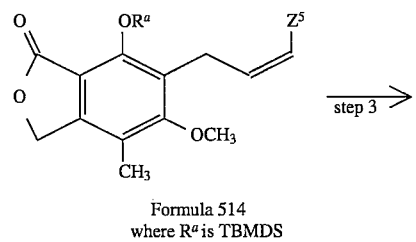

Formula 514
where $R^a$ is TBMDS $\xrightarrow{\text{step 3}}$

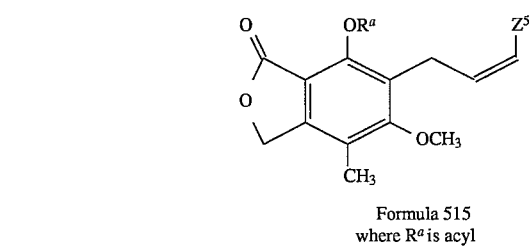

Formula 515
where $R^a$ is acyl

Formula 515

+

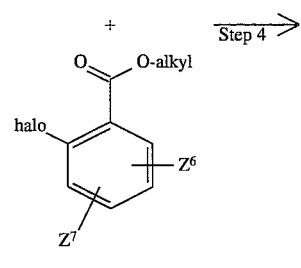

Formula 516

$\xrightarrow{\text{Step 4}}$

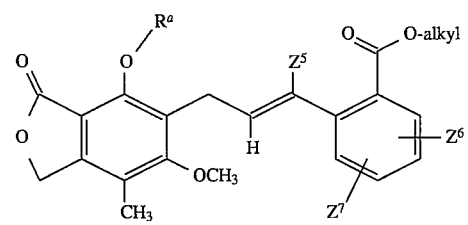

Formula 511

Preparation of Formula 513

As illustrated in Reaction Scheme XVII, Step 1, a protected aldehyde of Formula 103 is converted to a trialkylsilylcarbinol of Formula 513 in a Grignard reaction.

An aldehyde of Formula 103 is reacted with from 1.0 to 1.25 (preferably 1.1) molar equivalents of a trialkylsilylalkyl-magnesium bromide (such as trimethylsilylpropylmagnesium bromide, or preferably trimethylsilylmethylmagnesium bromide) of Formula 512, in an ethereal solvent (such as ether, dimethoxyethane or preferably tetrahydrofuran). The reaction takes place at –40° to 40° C. (preferably 0° C.) for 30 minutes to 4 hours (preferably 1 hour) to give the corresponding trialkylsilylcarbinol of Formula 513.

Preparation of Formula 514

As illustrated in Reaction Scheme XVII, Step 2, a protected trialkylsilylcarbinol of Formula 513 is dehydrated to give the corresponding protected alkene as a mixture of E and Z isomers, from which the desired Z isomer of Formula 514 is isolated.

A carbinol of Formula 513 is reacted with from 1.0 to 1.5 (preferably 1.05) molar equivalents of a sulphonyl chloride (such as p-toluenesulphonyl chloride or preferably methanesulphonyl chloride) in the presence of the same molar proportion of a tertiary organic base (such as N-methylpyrrolidine or preferably triethylamine). The reaction takes place at 0° to 40° C. (preferably 15° C.) for 30 minutes to 4 hours (preferably 2 hours) to afford the corresponding protected alkene of Formula 514 as a mixture of E and Z isomers, from which the desired Z-isomer of Formula 514 can be isolated by conventional means (such as distillation, chromatography or preferably fractional crystallization).

Preparation of Formula 515

As illustrated in Reaction Scheme XVII, Step 3, an alkene of Formula 514 where F is a silyl protecting group is converted to an alkene of Formula 515 where F is an acyl group.

An alkene of Formula 514 is heated at 50°–130° C. (preferably about 118° C.) with a large excess of a mixture (preferably about equimolar) of a carboxylic acid of Formula $R^aOH$ and an anhydride of Formula $(R^a)_2O$ (where $R^a$ is the desired acyl group), preferably a mixture of acetic acid and acetic anhydride. The reaction takes place over a period of 6 to 48 hours (preferably 18 hours) to give the corresponding alkene of Formula 515 where $R^a$ is the acyl group.

Preparation of Formula 511

As illustrated in Reaction Scheme XVII, Step 4, a protected alkene of Formula 515 is converted to a protected optionally substituted benzoic acid alkyl ester of Formula 511 in a Hack reaction with an alkyl-2-halo-benzoate of Formula 515.

An alkene of Formula 515 is reacted with 1.0 to 2.0 (preferably 1.25) molar equivalents of an alkyl 2-halobenzoate (such as an alkyl 2-bromobenzoate or preferably 2-iodobenzoate). The reaction is conducted in the presence of from 0.001 to 0.1 (preferably 0.05) molar equivalents of a palladium catalyst [such as tetrakis(tri-o-tolylphosphine) palladium, or tetrakis(triphenylphosphine)palladium or preferably palladium (II) acetate] optionally in the presence of from 1.0 to 1.25 (preferably 1.05) molar equivalents of a base (such silver carbonate, sodium bicarbonate or preferably triethylamine), in a solvent (such as acetonitrile or preferably dimethylformamide). The reaction is conducted at from 0° to 120° C. (preferably 60PC) for 1 to 48 hours (preferably 6 hours) to yield the corresponding protected optionally substituted benzoic acid alkyl ester of Formula 511.

Preparation of Formula 1E

The protected optionally substituted benzoic acid ester of Formula 506 or Formula 511 are then deprotected to give the corresponding ester of Formula 1E. The deprotection reaction takes place as described above with reference to Reaction Scheme X, Step 1. The optionally substituted benzoic acid ester of Formula 1E may then be hydrolyzed to give the corresponding acid of Formula 1E as described above with reference to Reaction Scheme X, Step 2.

Preparation of Formula 1E where $Z^4$ is Amino

The compounds of Formula 1E where $Z^6$ is nitro are employed as precursors to the corresponding compounds of Formula 1E where $Z^6$ is amino. The nitro compounds are also active as IMPDH inhibitors when tested as described below.

A nitrobenzoic acid of Formula 1E (where $Z^6$ is nitro) is reacted with 1.0 to 3.0 (preferably 2.0) molar proportions of a reducing agent (such as sodium hydrosulfite or preferably tin (II) chloride) in hydrochloric acid solution, optionally in the presence of a water-miscible co-solvent (such as methanol or preferably acetic acid). The reaction takes place at 25° to 100° C. (preferably 75° C.) for 1 to 24 hours (preferably 4 hours) to afford the corresponding amino-substituted benzoic acid of Formula 1E (where $Z^6$ is amino).

REACTION SCHEME XVIII

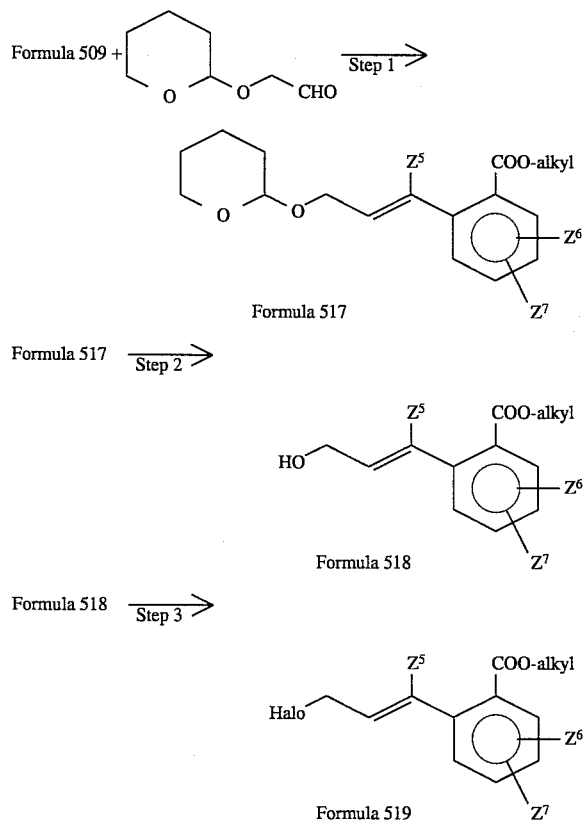

REACTION SCHEME XVIII -continued

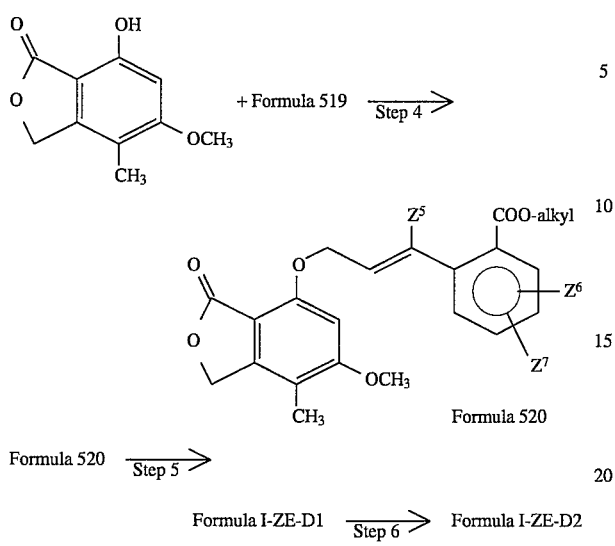

Formula 520 →(Step 5)→

Formula I-ZE-D1 →(Step 6)→ Formula I-ZE-D2

Preparation of Formula 517

As illustrated in Reaction Scheme XVIII, Step 1, a phosphonate of Formula 509 undergoes a base catalyzed condensation (e.g., using 1 molar equivalent of sodium hydride) with tetrahydropyranyloxyacetaldehyde, in a solvent such as dimethylformamide. The reaction takes place at 25° C. over a period of 1 to 4 hours, to give E/Z mixture from which the desired product of Formula 517 can be isolated by conventional means, such as chromatography.

Preparation of Formula 518

As illustrated in Reaction Scheme) XVIII, Step 2, the tetrahydropyranyloxy group of a compound of Formula 517 is hydrolyzed in the presence of a catalytic amount of a dilute acid (e.g., HCl) in aqueous tetrahydrofuran. The reaction takes place at 25° C. over a period of 1 to 4 hours, to give the corresponding carbinol of Formula 518.

Preparation of Formula 519

As illustrated in Reaction Scheme XVIII, Step 3, a carbinol of Formula 518 is converted to the halo (e.g., chloro or bromo) derivative of Formula 519 using 1 molar equivalent of triphenylphosphine and either carbon tetrachloride or carbon tetrabromide, in dichloromethane. The reaction takes place at 25° C. over a period of 2 hours.

Preparation of Formula 520

As illustrated in Reaction Scheme XVIII, Step 4, a halo derivative of Formula 519 undergoes a base-catalyzed ether formation with the indicated phenol, using 5 molar equivalents of potassium carbonate, in dimethylformamide. The reaction takes place at 25° C. over a period of 4 hours.

Preparation of Formula 1E

As illustrated in Reaction Scheme XVIII, Step 5, an ether of Formula is rearranged to give the corresponding ester of Formula 1E by a thermal rearrangement catalysed by florisil. The rearrangement takes place in toluene at 110° C. over a period of one to four days.

As illustrated in Reaction Scheme XVIII, Step 6, the ether so-produced is hydrolyzed to the corresponding acid of Formula 1E as described with reference to Reaction Scheme X, Step 2.

Preparation of Compounds of Formula 1F

One method of preparing compounds of Formula 1 where Z is a sidechain of Formula ZF, illustrated as compounds of Formula 1F, is shown below in Reaction Scheme XIX.

REACTION SCHEME XIX

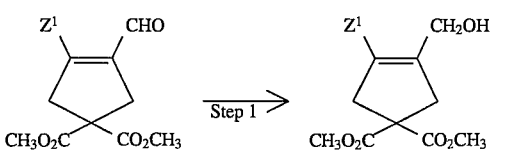

Formula 601 →(Step 1)→ Formula 602

Formula 603 + Formula 602 →(Step 2)→

Formula 604

Formula 604 →(Step 3)→

Formula 605

Formula 605 →(Step 4)→

Formula 606

Formula 606 →(Step 5)→

Formula 1F

Preparation of Formula 602

As illustrated in Reaction Scheme XIX, Step 1, an aldehyde of Formula 601, prepared for example as shown in *J. Org. Chem.*, 1977, p3408, is reduced to a carbinol of Formula 602.

An aldehyde of Formula 601 is reacted with a reducing agent capable of selectively reducing an aldehyde in the presence of ester groups, preferably from 1 to 2 (preferably 1.5) molar equivalents of sodium borohydride in the presence of from 1 to 2 (preferably 1.5) molar equivalents of cerium chloride trihydrate, in an alcoholic/ethereal solvent mixture (preferably 4:1 tetrahydrofuran:methanol). The reaction takes place at 0° to 40° C. (preferably 25° C.) for 10 minutes to 2 hours (preferably minutes) to give the corresponding carbinol of Formula 602.

Preparation of Formula 604

As illustrated in Reaction Scheme XIX, Step 2, a phenol of Formula 603 is alkylated with a carbinol of Formula 602 by means of the Mitsonobu reaction to give an ether of Formula 604.

A carbinol of Formula 602 is reacted with an equimolar amount of a phenol of Formula 603 in the presence of from i to 3 (preferably 2) molar equivalents of a triarylphosphine, preferably triphenylphosphine, plus from 1 to 3 (preferably 1.5) molar equivalents of diethyl azodicarboxylate in an ethereal solvent (preferably tetrahydrofuran). The reaction takes place at 0° to 40° C. (preferably 25° C.) for 1 to 10 hours (preferably 3 hours) to give the corresponding ether of Formula 604.

Preparation of Formula 605

As illustrated in Reaction Scheme XIX, Step 3, a phenol of Formula 604 is thermally rearranged to give a diester of Formula 605.

An ether of Formula 604 is heated in an inert solvent (preferably toluene) in the presence of about 10 parts by weight of an activated magnesium silicate, preferably Florisil©. The reaction takes place at reflux temperature for 1 to 10 days (preferably 4 days) to give the corresponding diester of Formula 605.

Preparation of Formula 606

As illustrated in Reaction Scheme XIX, Step 4, a diester of Formula 605 is hydrolyzed to give a dicarboxylic acid of Formula 606.

A diester of Formula 605 is reacted with an excess of an inorganic base, preferably about 50 molar equivalents of lithium hydroxide, in an aqueous solvent (preferably 5:1 methanol:water). The reaction takes place at 0° to 40° C. (preferably 25° C.) for 1 to 10 days (preferably 2 days) to give the corresponding dicarboxylic acid of Formula 606.

Preparation of Formula 1F

As illustrated in Reaction Scheme XIX, Step 5, a dicarboxylic acid of Formula 606 is decarboxylated to give a monocarboxylic acid of Formula 1F.

A dicarboxylic acid of Formula 606 is heated (optionally in the presence of a high boiling inert solvent, for example tetramethylbenzene, but preferably in the absence of any solvent). The reaction takes place at 160° to 240° C. (preferably 195° C.) for about 5 minutes to give the corresponding monocarboxylic acid of Formula 1F.

Preparation of Compounds of Formula 1G

One method of preparing confounds of Formula 1 where Z is sidechain of Formula ZG, illustrated as compounds of Formula 1G, is shown below in Reaction Scheme XX.

REACTION SCHEME XX

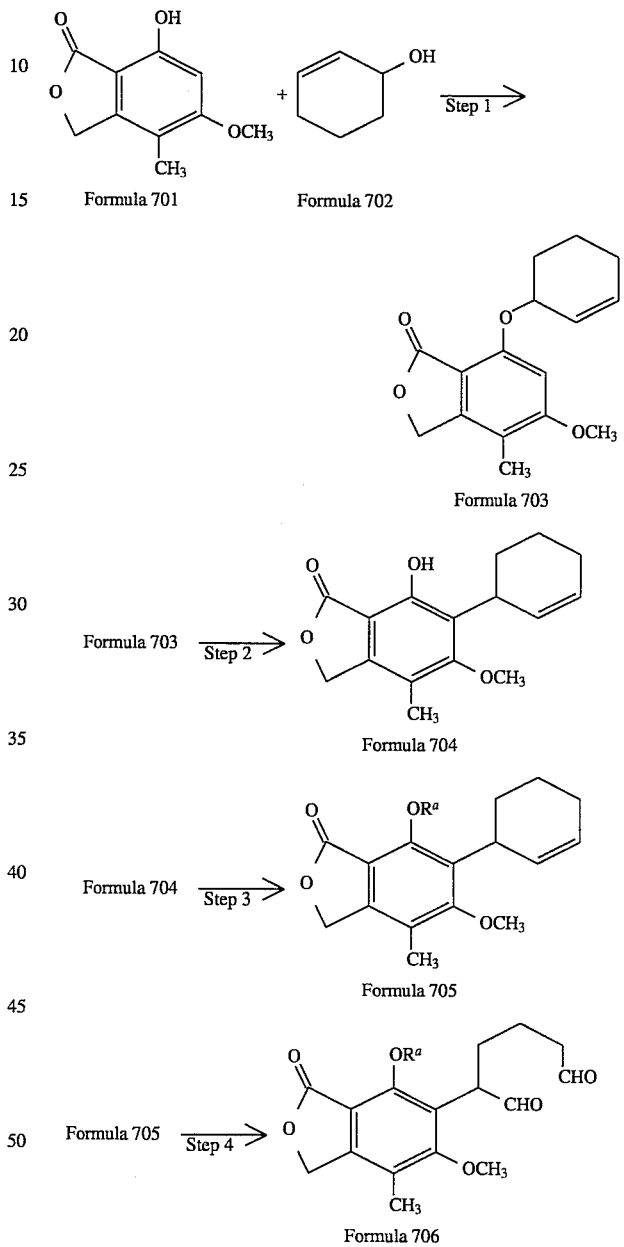

-continued
REACTION SCHEME XX

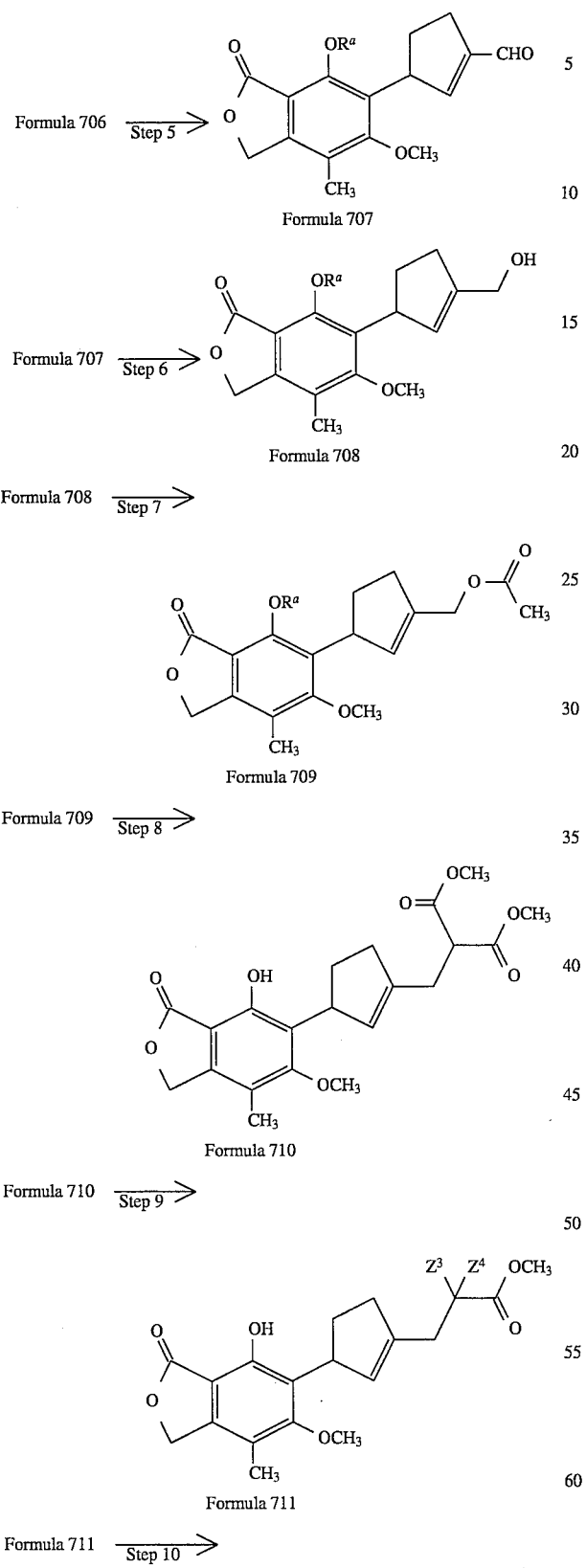

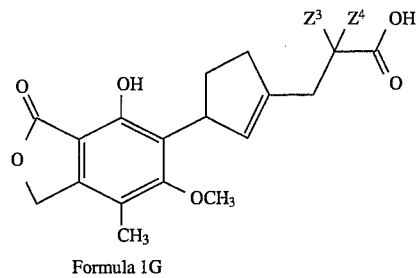

Preparation of Formula 703

As illustrated in Reaction Scheme XX, Step 1, the phenol of Formula 701 is alkylated with 3-hydroxycyclohexene to give the corresponding ether of Formula 703, by means of the Mitsonobu reaction. The Mitsonobu reaction takes place as described with reference to Reaction Scheme XIX, Step 2.

Similarly, by substituting 3-cyclohexene with 3-cycloheptene, and carrying out the procedures of Reaction Scheme XX, the corresponding compounds where Z is a side chain of Formula ZG where $D^3$ is —$CH_2$—$CH_2$— are obtained.

Preparation of Formula 704

As illustrated in Reaction Scheme XX, Step 2, a Claisen rearrangement of the ether of Formula 703 gives the alkylated phenol of Formula 704. The reaction takes place, e.g., at 200° C. for 12 to 16 hours in the presence of N,N-diethylaniline.

Preparation of Formula 705

As illustrated in Reaction Scheme XX, Step 3, the alkylated phenol of Formula 704 is protected to give a protected phenol of Formula 705 (where $R^a$ is silyl or tosyl).

An alkylated phenol of Formula 704 is reacted with an equimolar amount of t-butyl dimethylsilyl chloride or p-toluenesulfonyl chloride, in the presence of an equimolar amount, respectively, of imidazole or 4-dimethylaminopyridine. The reaction takes place in dichloromethane at a temperature of 25° C. for 1 to 4 hours to give the corresponding protected phenol of Formula 705.

Preparation of Formula 706

As illustrated in Reaction Scheme XX, Step 4, a protected phenol of Formula 705 is converted to the corresponding dialdehyde of Formula 706 by ozonolysis. The ozonolysis reaction takes place as described with reference to Reaction Scheme I, Step 2.

Preparation of Formula 707

As illustrated in Reaction Scheme XX, Step 5, an intramolecular base-catalyzed aldol reaction with a dialdehyde of Formula 706 produces the corresponding formyl cyclopentene of Formula 707. The reaction is conducted with 0.1 moles of dibenzylamine or n-methylaniline trifluoroacetate in benzene, taking place at 50° C. for 30 minutes.

Preparation of Formula 708

As illustrated in Reaction Scheme XX, Step 6, a formyl cyclopentene of Formula 707 is reduced to the corresponding carbinol. The reaction employs sodium borohydride/cerium chloride, as described with reference to Reaction Scheme XIX, Step 1.

Preparation of Formula 709

As illustrated in Reaction Scheme XX, Step 7, a carbinol of Formula 708 is converted to the corresponding acetate of Formula 709. The reaction is conducted with equimolar amounts of acetyl chloride and triethylamine, taking place in methylene chloride at 0° C. for 1 hour.

49

Preparation of Formula 710

As illustrated in Reaction Scheme XX, Step 8, an acetate of Formula 709 is converted to the corresponding diester of Formula 710. The reaction is conducted as described in *J. Am. Chem. Soc.*, 102:4730 (1980), with 4 moles of sodium dimethylmalonate, 0.5 moles triphenylphosphine and 0.25 moles of tetrakis triphenylphosphine palladium at 50° C. in tetrahydrofuran. Use of sodium dimethylmalonate substituted by $Z^3$ or $Z^4$ leads to a compound of Formula 711 where one of $Z^3$ and $Z^4$ is as defined in the Summary of the Invention and the other is hydrogen.

Preparation of Formula 711

As illustrated in Reaction Scheme XX, Step 9, a diester of Formula is converted to the corresponding ester of Formula 711, by reaction with cesium acetate in hexamethylphosphoric triamide at 120° C. for 1 to 3 hours.

Preparation of Formula 1B

As illustrated in Reaction Scheme XX, Step 10, an ester of Formula 111 is hydrolyzed to give the corresponding compound of Formula 1G. The reaction takes place as described with reference to Reaction Scheme X, Step 2.

Preparation of Compounds of Formula 1B

One method of preparing compounds of Formula 1 where Z is sidechain of Formula ZH, illustrated as compounds of Formula 1H, is shown below in Reaction Scheme XXI.

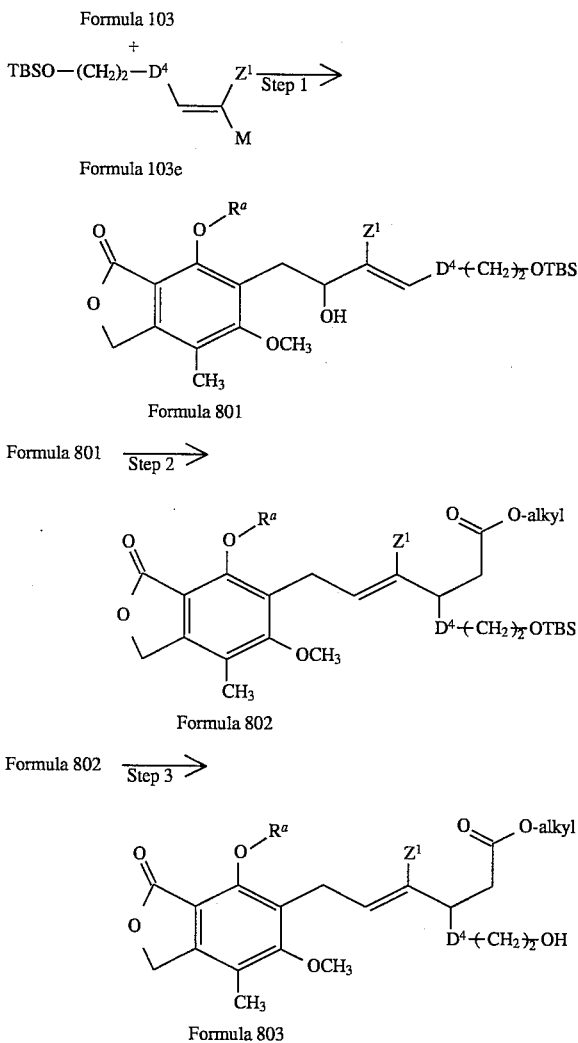

50

-continued
REACTION SCHEME XXI

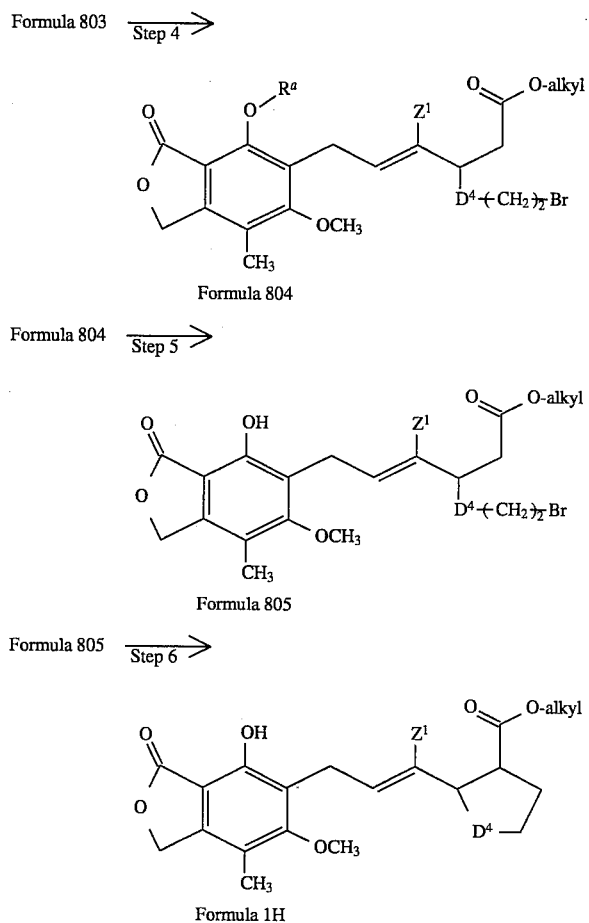

Preparation of Formula 801

As illustrated in Reaction Scheme XXI, Step 1, an aldehyde of Formula 103 is converted to a carbinol by addition of an organometallic compound of Formula 103e (such as a substituted vinyl organolithium, or preferably a Grignard reagent, where M is MgBr; TBS is a tert-butyldimethylsilyl protecting group; and n is 3–5).

A halovinyl (preferably bromovinyl) compound of Formula 103e (where M is halo) is reacted with magnesium metal in an ethereal solvent (such as ether or preferably tetrahydrofuran). The reaction takes place at 30° to 60° C. (preferably 40° C.) over a period of 1 to 6 hours (preferably 2 hours). One molar equivalent of the resultant organometallic reagent is added to a solution of an aldehyde of Formula 103 (in the same solvent system used to make the organometallic reagent). The reaction takes place at −80° to 20° C. (preferably 0° C.) over a period of 5 to 60 minutes (preferably 10 minutes) to give the corresponding silyl-protected carbinol of Formula 801.

Preparation of Formula 802

As illustrated in Reaction Scheme XXI, Step 2, an alkyl ester of Formula 802 is formed by a Claisen ortho ester rearrangement reaction of a carbinol of Formula 801 and an orthoester compound of Formula 104a (as illustrated in Reaction Scheme I, where $Z^3$ and $Z^4$ are H).

A silyl-protected carbinol of Formula 801 is heated at 50° to 120° C. (preferably about 100° C.) with about 10 molar equivalents of an orthoester of Formula 104a, in the presence of from 0.05 to 0.25 molar equivalents (preferably 0.10 molar equivalents) of an organic acid catalyst (such as propionic, butyric, or preferably trimethylacetic acid). The reaction takes place over a period of 1 to 48 hours (preferably 8 hours) to give the corresponding alkyl ester of Formula 802.

Preparation of Formula 803

As illustrated in Reaction Scheme XXI, Step 3, the silyl-protected carbinol of an alkyl ester of Formula 802 is deprotected.

A compound of Formula 803 is reacted with from 5 to 30 (preferably 20) molar equivalents of hydrogen fluoride, in a mixture of water and a water-miscible organic solvent (preferably acetonitrile). The reaction takes place at −20° to 40° C. (preferably 25° C.) for 5 to 60 minutes (preferably 30 minutes) to afford the corresponding unprotected carbinol/alkyl ester of Formula 803.

Preparation of Formula 804

As illustrated in Reaction Scheme XXI, Step 4, a carbinol of Formula 803 is converted to a halide (preferably a bromide) of Formula 804, by means of a one-step or a two-step procedure.

In the one-step procedure, a carbinol of Formula 803 is reacted with from 1.0 to 1.3 (preferably 1.1) molar equivalents of a triaryl (preferably triphenyl) phosphine, and from 1.0 to 1.3 (preferably 1.1) molar equivalents of a halogen source (such as N-bromosuccinimide or preferably carbon tetrabromide). The reaction is conducted in an inert solvent (such as ether or preferably tetrahydrofuran). The reaction takes place at 0° to 50° C. (preferably 25° C.) for 1 to 12 hours (preferably 3 hours) to afford the corresponding halide of Formula 804.

Alternatively, in the two-step procedure, which is preferred, a carbinol of Formula 803 is converted first into a sulphonate ester (such as a p-toluenesulphonate or preferably a methanesulphonate) by reaction with from 1.0 to 1.5 (preferably 1.3) molar equivalents a sulphonyl halide (preferably methanesulphonyl chloride) in the presence of an equimolar amount of a tertiary organic base (preferably diisopropylethylamine) in a solvent (such as chloroform or preferably dichloromethane). The reaction takes place at −20° to 30° C. (preferably 0° C.) for 10 to 60 minutes (preferably 30 minutes). The so-obtained sulphonate ester is then reacted with from 5 to 20 (preferably 20) molar equivalents of an alkali metal halide (preferably lithium bromide) in a solvent (such as 2-butatone or preferably acetone). The reaction takes place at 0° to 56° C. (preferably at reflux) for 30 to 180 minutes (preferably 90 minutes) to afford the corresponding halide of Formula 804.

Preparation of Formula 805

As illustrated in Reaction Scheme XXI, Step 5, a halogenated carbinol/alkyl ester of Formula 804 is deprotected at the phenolic group to give the corresponding halogenated carbinol/alkyl ester of Formula 805. The deprotection reaction takes place as described above with reference to Reaction Scheme X, Step 1.

Preparation of Formula 1H

As illustrated in Reaction Scheme XXI, Step 6, a halogenated carbinol/alkyl ester of Formula 805 is subjected to a base-induced cyclization reaction to afford the product of Formula 1H.

A compound of Formula 805 is reacted with from 2.0 to 2.5 (preferably 2.3) molar equivalents of a strong base (such as lithium diisopropylamide, sodium hydride or preferably sodium hexamethyldisilazide) in a solvent (such as dioxane or preferably tetrahydrofuran). The reaction takes place at −20° to 30° C. (preferably at 0° C.) for 5 to 60 minutes (preferably 15 minutes) to afford the corresponding cycloalkylester of Formula 1H. The cycloalkyl ester of Formula I-ZH-A1 may then be hydrolyzed to give the corresponding acid of Formula 1H. The hydrolysis takes place as described above with reference to Reaction Scheme X, Step 2.

Compounds of Formula I where Z is a sidechain of Formula ZH in which $D^4$ is O or $O-CH_2$ are preferably prepared as described below in Reaction Scheme XXII.

REACTION SCHEME XXII

Formula 302

+   Step 1 →

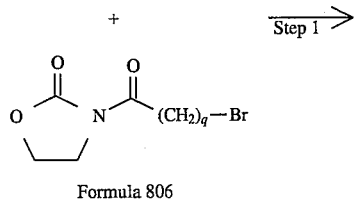

Formula 806

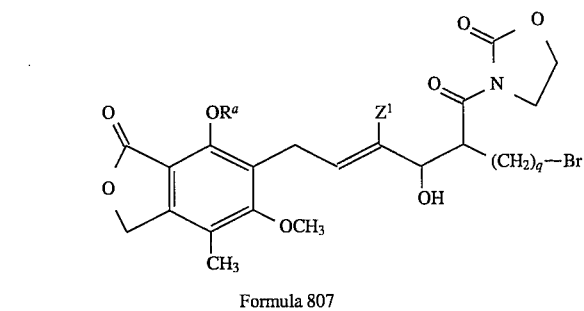

Formula 807

Formula 807   Step 2 →

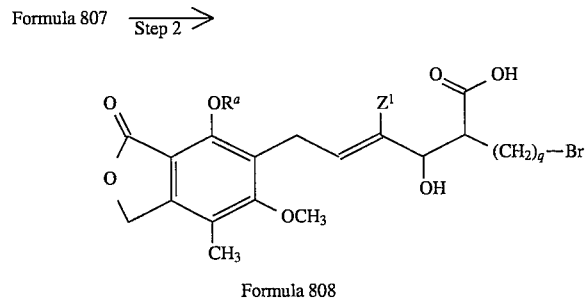

Formula 808

Formula 808   Step 3 →

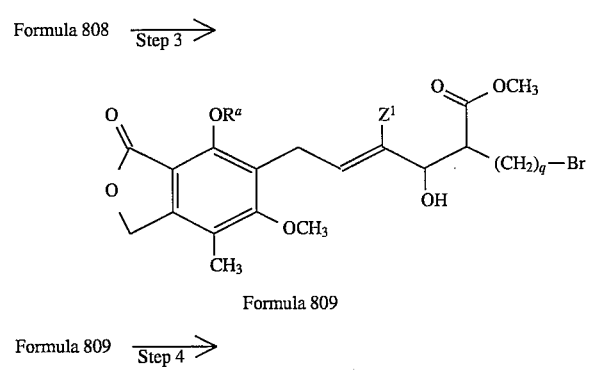

Formula 809

Formula 809   Step 4 →

REACTION SCHEME XXII -continued

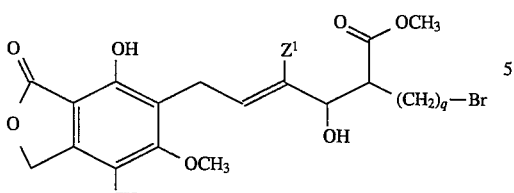

Formula 810

Formula 810 $\xrightarrow{\text{Step 5}}$

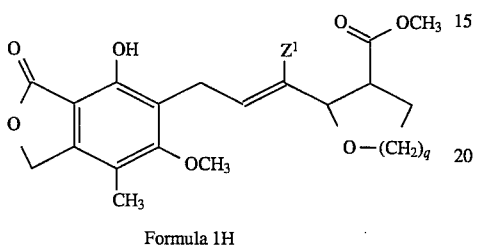

Formula 1H

Preparation of Formula 807

As illustrated in Reaction Scheme XXII, Step 1, an aldehyde of Formula 302 (where $Z^5$ is methyl) undergoes an aldol reaction with the bromo-alkyl oxazolidinone of Formula 806 (where q is 1 or 2), which can be prepared by analogy with the reactions described in *J. Amer. Chem. Soc.*, 103, 2127, 1981, to give the acyloxazolidinone of Formula 807.

An oxazolidinone of Formula 806 is reacted with an equimolar amount of a base (such as lithium diisopropylamide or preferably di-n-butylboryl trifluoromethane sulphonate/triethylamine), and then with an aldehyde of Formula 302. The reaction takes place at −78° C. to 0° C. (preferably 31 40° C.) for 1 to 12 hours (preferably 3 hours) to afford the corresponding acyloxazolidinone of Formula 807.

Preparation of Formula 808

As illustrated in Reaction Scheme XXII, Step 2, an acyloxazolidinone of Formula 807 is hydrolyzed to the carboxylic acid of Formula 808.

An acyloxazolidinone of Formula 807 is reacted with 1–5 (preferably 3) molar equivalents of lithium hydroxide in 3:1 tetrahydrofuran containing 5–20 (preferably 12) molar equivalents of hydrogen peroxide. The reaction takes place at −10° to 25° C. (preferably 0°) for 5 to 60 minutes (preferably 30 minutes) to give the corresponding carboxylic acid of Formula 808.

Preparation of Formula 809

As illustrated in Reaction Scheme XXII, Step 3, a carboxylic acid of Formula 808 is deprotected to give the corresponding phenol of Formula 809, using the method described with respect to Reaction Scheme X, Step 1.

Preparation of Formula 810

A phenol of Formula 809 is esterified to give the corresponding ester of Formula 810.

A phenol of Formula 809 is treated with methanol in the presence of 0.05 to 0.2 (preferably 0.1) molar equivalents of an acid catalyst (preferably p-toluenesulphonic acid). The reaction takes place at 0° to 50° C. (preferably 25° C.) for 1 to 24 hours (preferably 12 hours) to give the corresponding methyl ester of Formula 810.

Preparation of Formula 1H

A methyl ester of Formula 810 undergoes an intramolecular cyclization reaction to give the corresponding cyclized ester of Formula 1H.

A methyl ester of Formula 810 is treated with 1.9 to 2.5 (preferably 2.0) molar equivalents of a strong base (such as lithium diisopropylamide or preferably sodium hydride) in tetrahydrofuran (or preferably dimethylformamide). The reaction takes place at −10° to 25° C. (preferably 0°) for 1–12 hours (preferably 2 hours) to give the corresponding cyclized ester of Formula 1H, which may be hydrolyzed to give the corresponding acid of Formula 1H, using the method described with respect to Reaction Scheme X, Step 2.

Preparation of Esters of Formula 1

The esters of Formula 1 (compounds where G is not OH) can be prepared as described in U.S. Pat. Nos. 4,727,069 and 4,753,935, incorporated herein by reference, by deprotection of a precursor (e.g., as described with reference to Reaction Scheme X, Steps 1) or as described below by attachment of a leaving group and its replacement by the desired ester.

Preparation of Intermediates of Formula 6

The preparation of a compound of Formula 6 is shown in Reaction Scheme XXIII below.

REACTION SCHEME XXIII

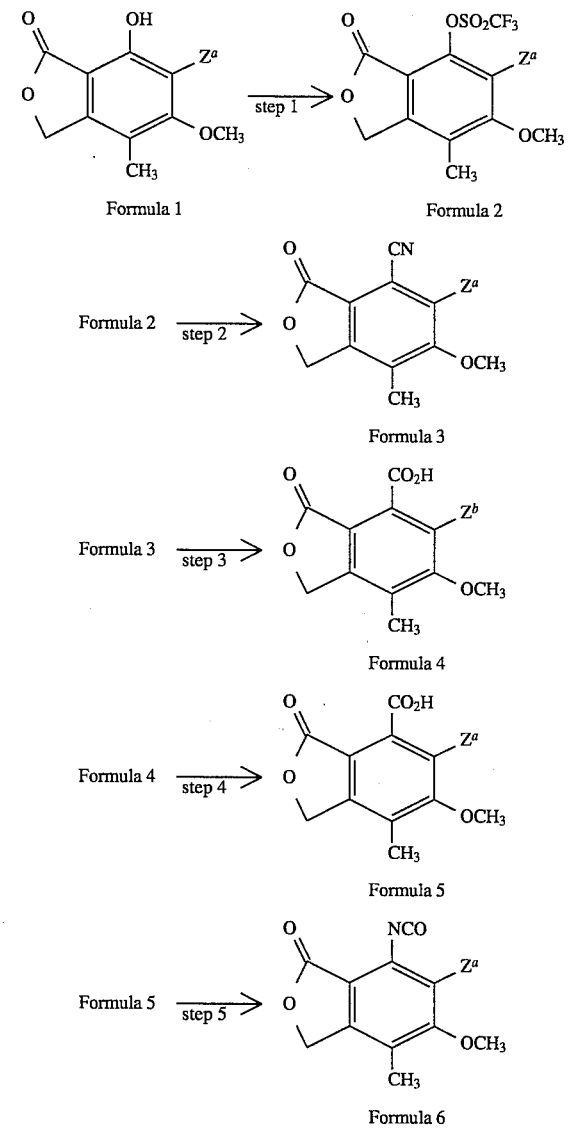

where $Z^a$ is a sidechain of Formula Z as defined in the Summary of the Invention in which G is lower alkoxy, and $Z^b$ is a sidechain of Formula Z as defined in the Summary of the Invention in which G is hydroxy.

Preparation of Starting Materials

The compound of Formula 1 (an ester) may be prepared from the corresponding carboxylic acid by reaction with a large excess of an alcohol of the formula GH, where G is lower alkoxy, preferably methanol, with a catalytic amount of an acid catalyst, (such as methanesulfonic acid, sulfuric acid, hydrochloric acid and p-toluenesulfonic acid), preferably p-toluenesulfonic acid). The reaction is carried out in the temperature range from about 0° C. to 40° C., preferably at about 20° C., for about 1 to 7 days, preferably about 24 hours. The lower alkyl ester of Formula 1 is isolated and purified by conventional means.

Preparation of Compounds of Formula 2

As illustrated in Reaction Scheme XXIII, Step 1, an ester of Formula 1 is converted to the trifluoromethylsulfonyl compound of Formula 2.

A compound of Formula 1 is reacted in an organic solvent, preferably dichloromethane, with about 1 to 3 molar equivalents, preferably about 2 molar equivalents, of a base, preferably pyridine, and with a slight excess, preferably about 1.1 molar equivalents, of a sulfonic anhydride, (such as a halo lower alkyl sulfonic anhydride, halomethyl sulfonic anhydride, and halosulfonic anhydride, or preferably trifluoromethane-sulfonic anhydride or fluorosulfonic anhydride) or a sulfonyl halide, (such as trifluoromethylsulfonyl bromide, preferably trifluoromethylsulfonyl chloride). The reaction is carried out in an inert solvent, preferably dichloromethane, in the temperature range from about −20° C. to 20° C., preferably at about 0° C., for about 15 to 45 minutes, preferably about 30 minutes. The trifluoromethylsulfonyl reaction product, a compound of Formula 2, is isolated and purified by conventional means.

Preparation of Compounds of Formula 3

As illustrated in Reaction Scheme XXIII, Step 2, a trifluoromethylsulfonyl derivative of Formula 2 is converted to the cyano compound of Formula 3.

A compound of Formula 2 is reacted with about 1 to 3 molar equivalents, preferably about 1.85 molar equivalents, of potassium cyanide with a catalytic amount of a tri-arylphosphine palladium complex, preferably tetrakis(triphenylphosphine) palladium, in an organic solvent, preferably 1,4-dioxane. The reaction is carried out in the temperature range from about 70° C. to 130° C., preferably at about the reflux temperature of 1,4-dioxane, for about 10 to 30 hours, preferably about 18 hours. The cyano reaction product, a compound of Formula 3, is isolated and purified by conventional means, preferably with extraction by an organic solvent and column chromatography.

Preparation of Compounds of Formula 4

As illustrated in Reaction Scheme XXIII, Step 3, the cyano compound of Formula 3 is hydrolyzed to the carboxy compound of Formula 4.

A compound of Formula 3 is hydrolyzed by reacting it with about 1 to 10 molar equivalents, preferably about 4 molar equivalents, of an inorganic base (e.g., sodium hydroxide, lithium hydroxide, or potassium hydroxide, preferably sodium hydroxide,) in a large excess of organic solvent, preferably in about 3:2 water:methanol solution. The reaction is carried out in the temperature range from about 40° C. to 130° C., preferably at about the reflux temperature of the 3:2 water/methanol solvent, for about 1 to 3 hours, preferably about 2 hours. The reaction solution is distilled, and an additional of about 1 to 1.6 molar equivalents, preferably about 1.3 molar equivalents, of an inorganic base (e.g., sodium hydroxide, lithium hydroxide, or potassium hydroxide, preferably sodium hydroxide,) is added and the reaction is continued in the temperature range from about 40° C. to 130° C., preferably at about the reflux temperature of the remaining solution, for about 1 to 3 days, preferably about 2 days. The reaction product, a compound of Formula 4, is isolated and purified by conventional means.

Alternatively, the compound of Formula 4 may be prepared by reacting a corresponding compound of Formula 2 with a catalytic amount of 1,1'-bis (diphenylphosphine)ferrocene palladium dichloride in a large excess of an alkanol (preferably methanol) in an organic solvent (preferably dimethylformamide) with a slight excess, preferably 1.01 molar equivalents, of an organic base (preferably triethylamine), under a carbon monoxide atmosphere of increased pressure of about 400–1000 PSI, preferably at about 600 PSI. The reaction product, which is a diester of a compound of Formula 4, is then hydrolyzed by reacting it with about 1 to 10 molar equivalents, preferably about 4 molar equivalents, of an inorganic base, preferably aqueous lithium hydroxide, in a large excess of an organic solvent, preferably 4:1 methanol/water solution. The solution is heated to a temperature range from about 30° C. to 80° C., preferably from about 50° C. to 60° C., for about 1 to 10 hours, preferably for about 2 to 6 hours. The reaction product, a compound of Formula 4, is isolated and purified by conventional means.

Preparation of Compounds of Formula 5

As illustrated in Reaction Scheme XXIII, Step 4, a carboxy derivative of Formula 4 is converted to the ester of Formula 5.

The compound of Formula 4 is reacted in a large excess of a compound of the formula GH, where G is lower alkoxy, preferably methanol, with catalytic amounts of an acid catalyst, preferably p-toluenesulfonic acid. The reaction is carried out in the temperature range from about 0° C. to 40° C., preferably at about 20° C., for about 4 hours to 3 days, preferably about 24 hours. The reaction product, a 4-carboxy derivative of Formula 5, is isolated and purified by conventional means.

Preparation of Compounds of Formula 6

As illustrated in Reaction Scheme XXIII, Step 5, a 4-carboxy derivative of Formula 5 is converted to the 4-isocyanate derivative of Formula 6.

A compound of Formula 5 is reacted with about 1 to 3 molar equivalents, preferably about 2 molar equivalents, of an organic base, preferably triethylamine, in a large excess of an organic solvent, preferably dimethylformamide, and about 1 to 2 molar equivalents, preferably about 1.3 molar equivalents, of an alkyl or phenyl haloformate or of a dialkyl or diphenyl halophosphate, preferably diphenyl chlorophosphate, in the temperature range from about −20° C. to 20° C., preferably at about 0° C., allowing it to warm to the temperature range from about 0° C. to 40° C., preferably at about 20° C., allowing the reaction to proceed for about 0.5 to 2 hours, preferably about 1 hour. The reaction mixture is recooled to the temperature range from about −20° C. to 20° C., preferably at about 0° C., and a large excess of sodium azide is added and the reaction proceeds for about 10 to 30 hours, preferably about 18 hours. The isocyanato reaction product, a compound of Formula 6, is isolated and purified by conventional means.

Alternatively, a compound of Formula 5 is reacted with about 1 to 3 molar equivalents, preferably about 2 molar equivalents, of an organic base, preferably triethylamine, in a large excess of an organic solvent, preferably dimethylformamide, and with a slight excess, preferably 1.2 molar equivalents, of a diphenyl or dialkyl phosphoroazide, preferably diphenyl phosphoroazide, in the temperature range from about 0° C. to 40° C., preferably at about 20° C., for about 12 to 36 hours, preferably for about 24 hours. The isocyanato reaction product, a compound of Formula 6, is isolated and purified by conventional means.

PREPARATION OF COMPOUNDS OF FORMULA I

In the following Reaction Schemes, it should be noted that $Z^a$ represents a sidechain of Formula Z as defined in the Summary of the Invention in which G is lower alkoxy, and $Z^b$ represents a sidechain of Formula Z as defined in the Summary of the Invention in which G is hydroxy.

1. Preparation of Compounds of Formula I where $R^1$ and $R^2$ are both Hydrogen Compounds of Formula I where $R^1$ and $R^2$ are both hydrogen are depicted as Formula IA:

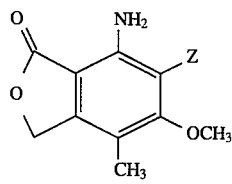

Formula IA

The preparation of compounds of Formula IA is shown in Reaction Scheme XXIV below.

REACTION SCHEME XXIV

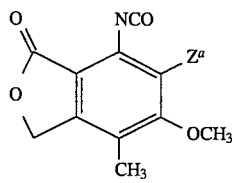

Formula 6

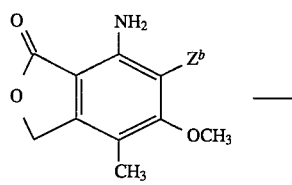

Formula IA

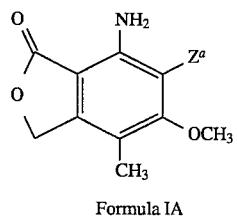

Formula IA where $Z^a$ and $Z^b$ are as defined above.

Preparation of Formula IA where Z is $Z^b$

A compound of Formula 6 is hydrolyzed with about 1 to 20 molar equivalents, preferably 10 molar equivalents, of an inorganic base, preferably lithium hydroxide monohydrate, in an inert organic solvent, preferably 3:10 water:1,4-dioxane. The reaction is carried out in the temperature range from about 0° C. to 40° C., preferably at about 20° C., for about 1 to 3 hours, preferably about 2 hours. The reaction product, a 4-amino compound of Formula IA where Z is $Z^b$, is isolated and purified by conventional means, preferably column chromatography.

Preparation of Formula IA where Z is $Z^a$

A compound of Formula IA is esterified with a lower alkanol of formula GH, where G is lower alkoxy, as described in the preparation of a compound of Formula I as an ester.

Preparation of Compounds of Formula I where $R^1$ is Hydrogen and $R^2$ is —C(O)NR$^4$R$^5$ Compounds of Formula I where $R^1$ is hydrogen and $R^2$ is —C(O)NR$^4$R$^5$ are depicted as Formula IB:

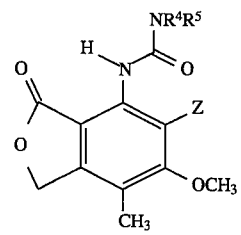

Formula IB

The preparation of compounds of Formula IB is shown in Reaction Scheme XXV below.

REACTION SCHEME XXV

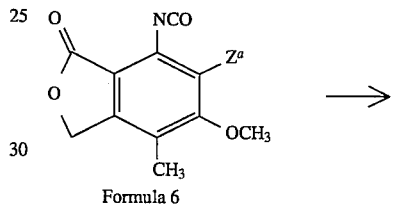

Formula 6

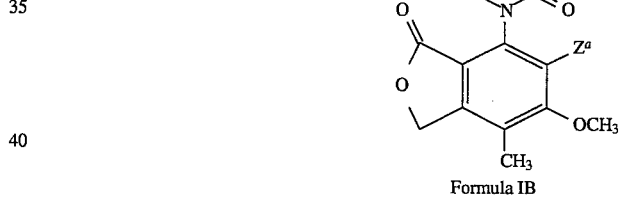

Formula IB

Preparation of Formula IB where Z is $Z^a$

A compound of Formula 6 is reacted with a large excess of an amine compound of the formula HNR$^4$R$^5$, where R$^4$ and R$^5$ are as defined in the Summary of Invention, for example, methylamine, dimethylamine, methylphenylamine, ammonia, and the like, in an inert organic solvent, preferably tetrahydrofuran. The reaction is carried out in the temperature range from about 0° C. to 40° C., preferably at about 20° C., for about 30 minutes to 2 hours, preferably about 1 hour. The reaction product, a 4-(optionally substituted ureido) ester of Formula IB is isolated and purified by conventional means.

Preparation of Formula IB where Z is $Z^b$

An ester of Formula IB is hydrolyzed by reacting with about 1 to 10 molar equivalents, preferably about 4 molar equivalents of an inorganic base, preferably aqueous lithium hydroxide, in a large excess of an organic solvent, preferably 4:1 methanol/water. The solution is heated to a temperature range from about 30° C. to 80° C., preferably from about 50° C. to 60° C., for about 1 to 10 hours, preferably for about 2 to 6 hours. The reaction product, a 4-(optionally substituted ureido) acid compound of Formula IB, is isolated and purified by conventional means.

Preparation of Compounds of Formula I where $R^1$ is Hydrogen and $R^2$ is —C(O)R$^3$ Compounds of Formula I where $R^1$ is hydrogen and $R^2$ is —C(O)$R^3$ are depicted as Formula IC:

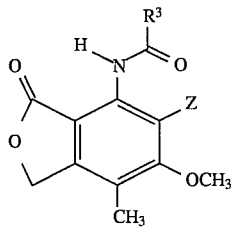

Formula IC

The preparation of compounds of Formula IC is shown in Reaction Scheme XXVI below.

REACTION SCHEME XXVI

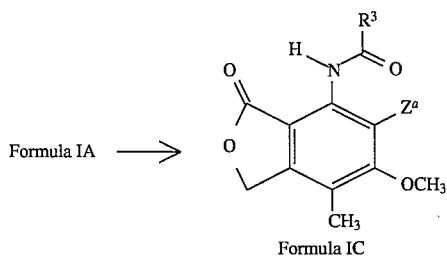

Preparation of Compounds of Formula IC where Z is $Z^a$

A compound of Formula IA is reacted in a large excess of an inert organic solvent, preferably dichloromethane, with about 1 to 6 molar equivalents, preferably about 2.5 molar equivalents, of an anhydride compound of the formula $(R^3C(O))_2O$ or of a acyl chloride of the formula $R^3C(O)Cl$, where $R^3$ is as defined in the Summary of the Invention. The reaction is carried out in the temperature range from about 0° C. to 40° C., preferably at about 20° C., for about 30 minutes to 2 hours, preferably about hour. The reaction product, a carbamate ester of Formula IC, is isolated and purified by conventional means, preferably by recrystallization.

Preparation of Formula XC where Z is $Z^b$

A compound of Formula IC as an ester is hydrolyzed as described in the preparation of a compound of Formula IB to give the corresponding compound of Formula IC as a carboxylic acid.

Preparation of Compounds of Formula I where $R^1$ is Lower Alkyl and $R^2$ is —C(O)$R^3$ Compounds of Formula I where $R^1$ is lower alkyl and $R^2$ is —C(O)$R^3$ are depicted as Formula ID:

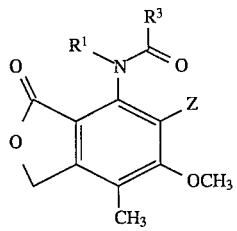

Formula ID

The preparation of compounds of Formula ID is shown in Reaction Scheme XXVII below.

REACTION SCHEME XXVII

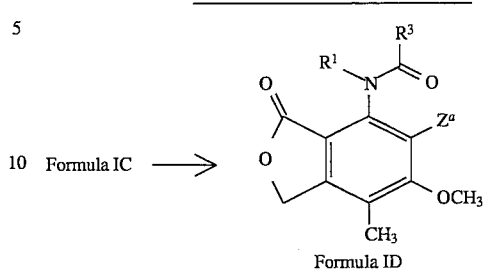

Preparation of Formula ID wherein $R^1$ is Lower Alkyl and Z is $Z^a$

A compound of Formula IC is reacted with about 1 to 10 molar equivalents, preferably about 4.5 molar equivalents, of a week base, preferably potassium carbonate, and with about 1 to 10 molar equivalents, preferably about 4 molar equivalents, of a lower alkyl bromide or iodide, preferably an iodide, in an inert organic solvent, preferably dimethylformamide. The reaction is carried out in the temperature range from about 0° C. to 40° C., preferably at about 20° C., for about 12 to 48 hours, preferably about 24 hours. The organic layer is purified to give a carbamate ester of Formula ID where $R^1$ is lower alkyl and G is lower alkoxy.

Preparation of Formula ID wherein $R^1$ is Lower Alkyl and Z is $Z^b$

A carbamate ester of Formula ID where $R^1$ is lower alkyl is hydrolyzed as described in the preparation of a compound of Formula IB to give the corresponding carboxylic acid of Formula ID where $R^1$ is lower alkyl.

Preparation of Compounds of Formula I where $R^a$ is Lower Alkyl and $R^2$ is Hydrogen Compounds of Formula I where $R^1$ is lower alkyl and $R^2$ is hydrogen are depicted as Formula IB:

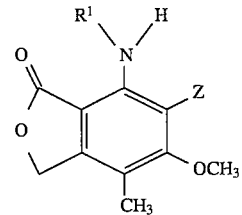

Formula IE

The preparation of compounds of Formula IE is shown in Reaction Scheme XXVIII below.

REACTION SCHEME XXVIII

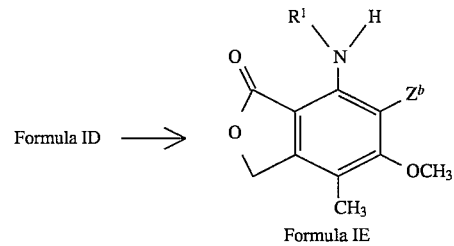

Preparation of Formula II where $R^1$ is Lower Alkyl and Z is $Z^b$

An amido enter of Formula ID is hydrolyzed by reacting with about 1 to 10 molar equivalents, preferably about 4 molar equivalents of an inorganic base (for example sodium hydroxide, preferably lithium hydroxide), in a large excess of an organic solvent, preferably 4:1 methanol/water. The solution is heated to a temperature range from about 50° C. to 100° C., preferably from about 60° C. to 80° C., for about 4 to 24 hours, preferably for about 12 hours. The reaction product, a 4-alkylamino acid compound of Formula IE, is isolated and purified by conventional means.

Preparation of Compounds of Formula I where G is Lower Alkoxy, Lower Thioalkoxy, or —O—$(CH_2)_m$—N=Y The compounds of Formula I where Z is a sidechain as defined in the Summary of the Invention in which G is lower alkoxy, lower thioalkoxy, or —O—$(CH_2)_m$—N=$G^3$ (i.e., the ester derivatives) may be prepared from the corresponding compounds of Formula I where G is hydroxy (i.e. where Z is $Z^b$), including compounds of Formulae IA, IB, IC, ID, and IE, by conventional means, for example as described in the preparation of a compound of Formula 1 as an ester.

Preferred Preparation of Esters of Formula I where G is —O—$(CH_2)_m$—N=Y

In a preferred procedure, a compound of Formula I where G is hydroxy is esterified with an heterocyclic aminoalkyl alcohol of the formula GH, where G is —O—$(CH_2)_m$—N—Y, in which m and Y are as defined in the Summary of the Invention, by the direct esterification procedure described in the pending application entitled "Direct Esterification of Mycophenolic Acid", Ser. No. 07/911635, filed Jul. 10, 1992.

In the direct esterification route, an acid compound of Formula I where G is hydroxy is esterified slowly in a refluxing inert organic solvent capable of azeotropic removal of water (such as toluene, xylene, or a mixture thereof) using only a slight excess (between 1.01 to 1.20 molar equivalents, and preferably, 1.05 to 1.06 molar equivalents) of an heterocyclic aminoalkyl alcohol of the formula HO$(CH_2)_m$—N—$G^3$. Water generated by the reaction is removed azeotropically.

For example, with toluene as the solvent: 1) the reaction takes place with (a) a reaction time of 20 to 120 hours, preferably 50 to 100 hours and most preferably 100 hours and (b) an initial pot temperature range of 114° to 120° C. increasing to a final pot temperature range of 118° to 130° C., preferably an initial pot temperature range of 115° to 118° C. increasing to a final pot temperature range of 118° to 125° C., each depending on solute concentration and atmospheric pressure, and most preferably an initial pot temperature of 116° C. increasing to a final pot temperature of 121° C. with a ratio of the acid compound of Formula I (where G is hydroxy) to toluene of 1 gm:2 ml at one atmosphere of pressure. The reaction product, a confound of Formula I where Z is a sidechain as defined in the Summary of the Invention in which G is —O—$(CH_2)_m$—N=$G^3$, is isolated and purified by conventional means.

Salts of Compounds of Formula I

Some of the compounds of Formula I may be converted to corresponding base addition salts by virtue of the presence of a carboxylic acid group. The conversion is accomplished by treatment with a stoichiometric amount of an appropriate base, such as potassium carbonate, sodium bicarbonate, ammonia, ethylenediamine, monoethanolamine, diethanolamine, triethanolamine and the like. Typically, the free acid is dissolved in a polar organic solvent such as ethanol, methanol or ethyl acetate, and the base added in water, ethanol, methanol or isopropanol. The temperature is maintained at about 0° C. to 50° C. The resulting salt precipitates spontaneously or may be brought out of solution with a less polar solvent.

The base addition salts of the compounds of Formula I may be decomposed to the corresponding free acids by treating with at least a stoichiometric amount of a suitable acid, such as hydrochloric acid or sulfuric acid, typically in the presence of aqueous solvent, and at a temperature of between about 0° C. and 50° C. The free acid form is isolated by conventional means, such as extraction with an organic solvent.

By virtue of the presence of an amine group in the 4-position or in the group G, some of the compounds of Formula I may be converted to the acid addition salts by the substitution of an organic or inorganic acid for the base in the above procedure. The acid salts can be decomposed to the corresponding free bases by similar treatment with an appropriate base.

Preferred Processes

In summary, compounds of Formula I are prepared according to the following last steps:

1. A process for preparing compounds of Formula I, wherein:

$R^1$ is hydrogen or lower alkyl;

$R^2$ is hydrogen, lower alkyl, —C(O)$R^3$, —C(O)N$R^4R^5$, —CO$_3R^4$, or —SO$_2R^3$ where:

$R^3$ is hydrogen, lower alkyl, halo lower alkyl or optionally substituted phenyl;

$R^4$ is hydrogen, lower alkyl or optionally substituted phenyl;

$R^5$ is hydrogen, lower alkyl or optionally substituted phenyl;

$R^6$ is lower alkyl or optionally substituted phenyl; and

Z is as defined in the Summary of the Invention, in which G is hydroxy:

comprises:

reacting a compound of the formula:

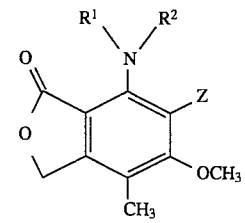

where Z is as defined in the Summary of the Invention, in which G is lower alkoxy, lower thioalkyl, N$G^1G^2$, O—$(CH_2)_a$—$N^1G^2$, or —O—$(CH_2)_a$—N=$G^3$, in which n, $G^1$, $G^2$, and $G^3$ are as defined in the Summary of the Invention; with an inorganic base.

2. Alternatively, a process for preparing compounds of Formula I, wherein:

$R^1$ and $R^2$ are as defined above, and G is lower alkoxy, lower thioalkyl, N$G^1G^2$, —O—$(CH_2)_n$—N$G^1G^2$, or O—$(CH_2)_a$N—$G^3$, in which n, $G^1$, $G^2$, and $G^3$ are as defined in the Summary of the Invention; comprises:

reacting a compound of the formula:

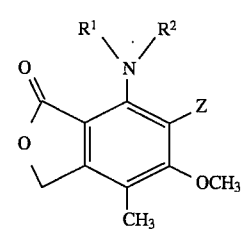

where Z is as defined in the Summary of the Invention, in which G is hydroxy, with a compound of the formula GH, where G is as defined above, except that G cannot be hydroxy.

3. Alternatively, a process for preparing compounds of Formula I, wherein:

$R^1$ is hydrogen;

$R^2$ is —C(O)NR$^4$R$^5$, where $R^4$ and $R^5$ are independently hydrogen, lower alkyl or optionally substituted phenyl; and Z is as defined in the Summary of the Invention, in which G is lower alkoxy:

comprises:

reacting a combed of the formula:

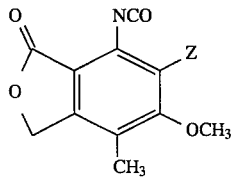

Formula 7 where Z is as defined in the Summary of the Invention, in which G is lower
alkoxy:

with a compound of the formula HNR$^4$R$^5$, where $R^4$ and $R^5$ are as defined above.

4. Alternatively, a process for preparing compounds of Formula I, wherein:

$R^1$ is hydrogen;

$R^2$ is —C(O)R$^3$, where $R^3$ is lower alkyl, halo lower alkyl or optionally substituted phenyl; and Z is as defined in the Summary of the Invention, in which G is lower alkyl, optionally substituted phenyl, or —(CH$_2$)$_m$—N=Y$_i$;

comprises:

reacting a compound of the formula:

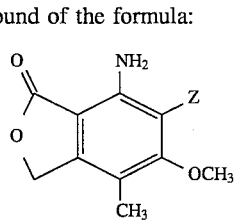

where $R^1$, $R^2$, and Z are as defined above;

with a compound of the formula (R$^3$C(O))$_2$O or R$^3$C(O)Cl.

5. Alternatively, a process for preparing compounds of Formula I, wherein:

$R^1$ is lower alkyl;

$R^2$ is —C(O)R$^3$, where $R^3$ is lower alkyl, halo lower alkyl or optionally substituted phenyl; and Z is as defined in the Summary of the Invention, in which G is lower alkoxy:

comprises:

reacting a compound of the formula:

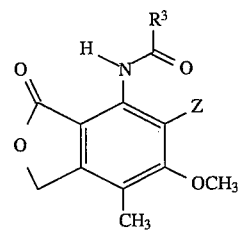

where Z is as defined in the Summary of the Invention, in which a is lower alkoxy:

with a compound of the formula R$^1$X, where $R^1$ is lower alkyl and X is iodine or bromine.

Preferred Compounds

Among the family of compounds of the present invention, one preferred category includes the compounds where Z is a sidechain of Formula ZA. Within this category a preferred group includes the compounds where $Z^1$ is hydrogen, especially where $R^1$ is hydrogen and $R^2$ is hydrogen or —C(O)R$^3$. Within this group a preferred subgroup includes the compounds where $R^2$, $Z^2$ and $Z^3$ are all hydrogen, especially where $Z^4$ is methyl. Another preferred subgroup includes the compounds where $R^2$, $Z^3$ and $Z^3$ are all hydrogen, especially where $Z^2$ is methyl.

Another preferred category includes the compounds where Z is a sidechain of Formula ZB, especially where $R^1$ is hydrogen and $R^2$ is hydrogen or —C(O)R$^3$. Within this category a preferred group includes the compounds where $D^1$ and $D^2$ together with the their adjacent carbon atoms form a saturated carbocyclic ring of 5 or 6 carbon atoms. Within this group a preferred subgroup includes the compounds where $D^1$ and $D^2$ together represent —CH$_2$CH$_2$CH$_2$—, especially where $Z^5$ and $Z^8$ are both hydrogen. A preferred class within this subgroup includes the compounds in which $R^1$ and $R^2$ are both hydrogen.

Another preferred subgroup includes the compounds where $D^1$ and $D^2$ together represent —CH$_2$CH$_2$CH$_2$CH$_2$—, especially where $Z^5$ and $Z^6$ are both hydrogen. A preferred class within this subgroup includes the compounds in which $R^1$ and $R^2$ are both hydrogen.

Yet another preferred subgroup includes the compounds where $D^1$ and $D^2$ together represent —CH$_2$CH$_2$—, especially where $Z^5$ and $Z^6$ are both hydrogen. A preferred class within this subgroup includes the compounds in which $R^1$ and $R^2$ are both hydrogen.

At present, the most preferred compounds are:

(E)-6-(4-amino-1,3-dihydro-6-methoxy-7-methyl - 3-oxoisobenzofuran-5-yl)-2(S), 4-dimethyl-4-hexenoic acid;

(E)-6-(4-amino-1,3-dihydro-6-methoxy-7-methyl - 3-oxoisobenzofuran-5-yl)-3(S), 4-dimethyl-4-hexenoic acid;

(E)-2-[2-[2-[4-amino-1,3-dihydro- 6-methoxy-7-methyl-3-oxoisobenzofuran- 5-yl]ethylidene]cyclopent-1(S)-yl] acetic acid; and (E)-2-{4-[2-(4-amino-1,3-dihydro-6-methoxy- 7-methyl-3-oxoisobenzofuran-5-yl)ethylidene]tetrahydropyran-3(S)-yl}acetic acid.

Utility, Testing and Administration

General Utility

The compounds of the present invention, the pharmaceutically acceptable salts thereof and pharmaceutical compositions therewith (collectively the "compounds" for purposes of the following description) are useful as immunosuppressive agents, anti-inflammatory agents, anti-tumor agents, anti-proliferative agents, anti-viral agents and anti-psoriatic agents in mammals, whether domestic (cattle, pigs, sheep, goats, horses), pets (cats, dogs), or preferably humans. The compounds are inhibitors of inosine monophosphate dehydrogenase (IMPDH) and thus inhibit de novo purine synthesis; they have anti-proliferative effects (e.g., against smooth muscle cells and both B and T lymphocytes) and inhibit antibody formation and the glycosylation of cell adhesion molecules in lymphocytes and endothelial cells.

As immunosuppressive agents, the compounds are useful in treating auto-immune related disorders, for example: Type I Diabetes Mellitus; Inflammatory Bowel Disease (e.g., Crohn's Disease and Ulcerative Colitis); Systemic Lupus Erythematosus; Chronic Active Hepatitis; Multiple Sclerosis; Grave's Disease; Hashimoto's Thyroiditis; Bahcat's Syndrome; Myasthenia Gravis; Sjogren's Syndrome; Pernicious Anemia; Idiopathic Adrenal Insufficiency; and Polyglandular Autoimmune Syndromes Type I and II.

The compounds are also useful as therapeutic immunosuppressive agents in the treatment of Asthma, Immunohemolytic Anemia, Glomerulonephritis, and Hepatitis. Preventative uses of the compounds as immunosuppressive agents include the treatment of allograft rejection, for example, in cardiac, lung, pancreatic, renal, liver, skin and corneal allografts, and prevention of Graft vs. Host Disease.

The compounds are useful for inhibiting proliferative responses to vascular injury, for example, stanosis following an insult to a blood vessel wall in post-angioplasty restenosis, and post-cardiac by-pass surgery restenosis.

The compounds are useful as anti-inflammatory agents, for example, in treating Rheumatoid Arthritis, Juvenile Rheumatoid Arthritis and Uveitis.

As anti-tumor agents, the compounds are useful in treating solid tumors and malignancies of lymphoreticular origin. For example, the compounds, utility for treatment of solid tumors includes: cancers of the head and neck, including squamous cell carcinoma; lung cancer, including small cell and non-small cell lung carcinoma; mediastinal tumors; esophageal cancer, including squamous cell carcinoma and adenocarcinoma; pancreatic cancer; cancer of the hepatobiliary system, including hepatocellular carcinoma, cholangiocarcinoma, gall bladder carcinoma and biliary tract carcinoma; small intestinal carcinoma, including adenocarcinoma, sarcoma, lymphoma and carcinoids; colorectal cancer, including colon carcinoma and rectal carcinoma; metastatic carcinoma; cancers of the genitourinary system, including ovarian cancer, uterine sarcoma, and renal cell, ureteral, bladder, prostate, urethral, penile, testicular, vulvar, vaginal, cervical, entometrial, and fallopian tube carcinoma; breast cancer; endocrine system cancer; soft tissue sarcomas; malignant mesotheliomas; skin cancer, including squamous cell carcinoma, basal cell carcinoma and melanoma; cancer of the central nervous system; malignant bone tumors; and plasma cell neoplasms.

As anti-tumor agents for the treatment of malignancies of lymphoreticular origin, the compounds are useful in treating, for example: Lymphomas and Leukemias, including B, T and promonocyte cell line malignancies, Mycoses Fungoides, Non-Hodgkins Lymphoma, Malignancies of Burkitt Lymphoma Cells and other EBV-transformed B-lymphocytes, Lymphomas resulting from Epstein-Bart vital infections in allograft recipients, Chronic Lymphocytic Leukemia, Acute Lymphocytic Leukemia and Hairy Cell Leukemia.

As anti-viral agents, the compounds are useful in treating, for example: retroviruses, including Human T-leukemia Viruses, Types I and II (HTLV-1 and HTLV-2), Human Immune Deficiency Viruses, Types I and II (HIV-1, HIV-2) and, Human Nasopharyngeal Carcinoma Virus (NPCV) and in treating Herpes Viruses, including EBV infected B-lymphocytes, CMV infection, Herpes Virus Type 6, Herpes Simplex, Types 1 and 2, (HSV-1, HSV-2 ) and Herpes Zoster.

As anti-psoriatic agents, the compounds are useful in treating, for example, psoriasis and psoriatic arthritis.

Testing

Activity testing is conducted as described in the following references, and by modifications thereof.

General anti-inflammatory, anti-viral, anti-tumor, anti-psoriatic and/or immunosuppressive activity is associated with the inhibition of Inosine 5'-Monophosphate Dehydrogenase ("IMPDH"). In vitro assays measuring the inhibition of IMPDH, for example, by determining the level of NADH formation according to the method of Anderson, J. H. and Sartorelli, A. C., *J. Biol. Chem.*, 243:4762–4768 (1968) are predictive of such activity.

Initial animal screening tests to determine anti-inflammatory activity potential include the adjuvant arthritis assay, e.g., according to the method of Pearson, *Proc. Sec. Exp. Biol. Med.*, 91:95–101 (1956). Also, in vitro tests, for example those using synovial explants from patients with rheumatoid arthritis, Dayer, et el., *J. Exp. Med.*, 145:1399–1404 (1977), are useful in determining whether compounds exhibit anti-inflaommtory activity.

Autoimmune activity is determined, for example, utilizing experimental allergic encephalomyelitis, by a modification of a procedure initially described by Grieg, et. al., *J. Pharmacol. Exp. Ther.*, 173:85 (1970).

Human clinical trials for efficacy in the treatment of asthma are conducted, e.g., as described by Erzurum, Leff, Cochran, et al. "Lack of benefit of methotrexate in severe, steroid-dependent asthma. A double-blind, placebo controlled study." *Ann. Int. Med.*, 114:353–360 (1991).

Activity to prevent the rejection of organ or tissue allografts in experimental animals is determined, for example, as described by Hao, et el., *J. Immunol.*, 139:4022–4026 (1987). In addition, U.S. Pat. No. 4,707,443 and EP 226062, incorporated herein by reference, also describe assays for activity in prevention of allograft rejection by detection of IL-2R levels. Human clinical trials to establish efficacy in preventing rejection of solid organ transplants (such as renal) are conducted, e.g., as described by Lindholm, Albrechtsen, Tufveson, et al., "A randomized trial of cyclosporin and prednisolone versus cyclosporin, azathioprine and prednisolone in primary cadaveric renal transplantation," *Transplantation*, 54:624–631 (1992). Human clinical trials for graft vs. host disease are conducted, e.g., as described by Storb, Deeg, Whitehead, et al., "Methotrexate and cyclosporin compared with cyclosporin alone for prophylaxis of acute graft versus host disease after marrow transplantation for leukemia." *New England J. Med.*, 314:729–735 (1986).

Immunosuppressive activity is determined by both in vivo and in vitro procedures. In vivo activity is determined, e.g., utilizing a modification of the Jerne hemolytic plaque assay, [Jerne, et al., "The agar plaque technique for recognizing antibody producing cells," Cell-bound Antibodies, Amos, B. and Kaproweki, H. editors (Wistar institute Press, Philadelphia) 1963, p. 109]. In vitro activity is determined, e.g., by an adaptation of the procedure described by Greaves, et al., "Activation of human T and B lymphocytes by polyclonal mitogens," *Nature*, 248:698–701 (1974).

Anti-viral activity is determined, for example, by the procedure described by Smee, et al. ["Anti-Herpesvirus Activity of the Acyclic Nucleoside 9-(1,3-Dihydroxy-2-Propoxymethyl) Guanine," *Antimicrobial Agents and Chemotherapy,* 23(5):676–682 (1983)], or as described by Planterose ["Antiviral and cytotoxic effects of mycophenolic acid," Journal of General Virology, 4:629 (1969)].

Anti-vital activity can likewise be determined by measurement of reverse transcriptase activity, for example, according to the method described by Chen et el., *Biochem. Pharm.,* 36:4361 (1987).

Human clinical trials for anti-HIV efficacy (together with clinical treatment scenarios) are described and cited, for example, by Sands, et al., "Antiretroviral Therapy for Adult HIV-Infected Patients," JAMA, 270(21):2583–2589 (1993). A large scale clinical trial can be conducted, e.g., as described by Volberding, P. A., et al. "Zidovudine in asymptomatic human immunodeficiency virus infection: a controlled trial in persons with fewer than 500 CD4 positive cells per cubic millimeter," *New England J. Med.,* 322(14):941–949 (1990). A smaller scale (Phase I) clinical trial can be conducted, e.g., as described by Browne, et al., "240 ,3'-Didehydro-3'-deoxythymidine (d4T) in Patients with AIDS or AIDS-Related Complex: A Phase I Trial," *J. Infectious Diseases,* 167:21–29 (1993).

Tests for systemic activity in psoriasis can be carried out, for example, as described by Spats, et al., "Mycophenolic acid in psoriasis," *British Journal of Dermatology,* 98:429 (1978).

Tests for anti-tumor activity can be performed, for example, as described by Carter, et al. ["Mycophenolic acid: an anticancer compound with unusual properties," *Nature,* 223:848 (1969)].

In vitro activity for treating stenosis is demonstrated, for example, by inhibiting the proliferation of smooth muscle cells, as established by the following human arterial smooth muscle cell proliferation assay. Human smooth muscle cells are grown in culture. A test group is treated with the test compound added at selected concentrations in fresh media. Both groups receive 2μCi tritiated thymidine ($^3$HTdR), a radioisotope label. After 24 hours, the cells are harvested and the amount of label incorporated into DNA is counted by scintillation; this is compared for the test and control groups, the amount being proportional to cell proliferation. Inhibition of smooth muscle proliferation is established when the test group has a lower radioisotope count than the control group. The concentrations of test compound required to inhibit proliferation by 50% (the $IC_{50}$), and to inhibit proliferation by more than 95% are determined.

In vivo activity for treating stenosis is demonstrated, for example, in rat and pig models for arterial stenosis. In the rat model, a test group is treated with the test compound, starting 6 days before and continuing for 14 days after injury to the left carotid artery; the test group is compared to a control group receiving vehicle without the test compound. Injury is achieved by a gentle perfusion of air through a 10 mm long section of the left artery. The right artery is left intact. Arterial cross-sections (10 μm) are taken free both the left and right arteries of each subject, and the area of the vessel wall (endothelium, intima, media) is measured, The amount of vascular proliferation is calculated by subtracting the mean area of the intact, right carotid artery from the mean area of the injured, left carotid artery. Reduction in vascular proliferation is established when the test group shows less proliferation than the control group.

Human clinical trials for restenosis after coronary angioplasty are conducted, e.g., as described by Serruys, Rutsch, Heyndrickx, et al., "Prevention of restenosis after percutaneous transluminal coronary antioplasty with thromboxane $A_2$-receptor blockade: a randomozed, double-blind, placebo-controlled trial." Circulation, 84: 1568–80 (1991).

Administration

The compounds of Formula I are administered at a therapeutically effective dosage, e.g., a dosage sufficient to provide treatment for the disease states previously described. Administration of the compounds of the invention or the pharmaceutically acceptable salts thereof can be via any of the accepted modes of administration for agents that serve similar utilities. The compounds can be used both prophylactically (e.g., to prevent allograft rejection) and therapeutically.

While human dosage levels have yet to be optimized for the compounds of the invention, generally, a daily dose is from about 0.01 to 100.0 mg/kg of body weight, preferably about 0.1 to 64.3 mg/kg of body weight, and most preferably about 0.3 to 43.0 mg/kg of body weight. Thus, for administration to a 70 kg person, the dosage range would be about 0.7 mg to 7 g per day, preferably about 7.0 mg to 4.5 g per day, and most preferably about 21 mg to 3.0 g per day. The amount of active compound administered will, of course, be dependent on the subject and disease state being treated, the severity of the affliction, the manner and schedule of administration (e.g., oral administration one day prior to cancer chemotherapy and intravenous administration during cancer chemotherapy) and the judgment of the prescribing physician.

In employing the compounds of this invention for treatment of the above conditions, any pharmaceutically acceptable mode of administration can be used. The compounds of Formula I can be administered either alone or in combination with other pharmaceutically acceptable excipients, including solid, semi-solid, liquid or aerosol dosage forms, such as, for example, tablets, capsules, powders, liquids, injectables, suspensions, suppositories, aerosols or the like. The compounds of Formula I can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages. The compositions will typically include a conventional pharmaceutical carrier or excipient and a compound of Formula I or a pharmaceutically acceptable salt thereof. In addition, these compositions may include other medicinal agents, pharmaceutical agents, carriers, adjuvants, etc., such as multidrug resistance modifying agents, steroids, immunosuppressants such as cyclosporine A, azathioprene, rapamycin, FK-506, brequinar, leflunomide and vincrystine.

Generally, depending on the intended mode of administration, the pharmaceutically acceptable composition will contain about 0.1% to 90%, preferably about 0.5% to 50%, by weight of a compound or salt of Formula I, the remainder being suitable pharmaceutical excipients, carriers, etc.

One preferred manner of administration for the conditions detailed above is oral, using a convenient daily dosage regimen which can be adjusted according to the degree of affliction. For such oral administration, a pharmaceutically acceptable composition is formed by the incorporation of any of the normally employed excipients, such as, for example, mannitol, lactose, starch, povidone, magnesium stearate, sodium saccharine, talcum, cellulose, croscarmellose sodium, glucose, gelatin, sucrose, magnesium carbonate, and the like. Such compositions take the form of solutions, suspensions, tablets, dispersible tablets, pills, capsules, powders, sustained release formulations and the like.

Preferably the compositions will take the form of a pill or tablet and thus the composition will contain, along with the active ingredient, a diluent such as lactose, sucrose, dicalcium phosphate, or the like; a lubricant such as magnesium stearate or the like; a disintegrant such as croscarmellose sodium or the like; and a binder such as search, gum acacia, polyvinylpyrrolidine, gelatin, cellulose and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, suspending agents, emulsifying agents, or solubilizing agents, pH buffering agents and the like, for example, sodium acetate, sodium citrate, cyclodextrine derivatives, polyoxyethylene, sorbitan monolaurate or stearate, etc. Actual methods of preparing such dosage forms are known, or will be apparent, to those skilled in this art; for example, see *Remington's Pharmaceutical Sciences*, Mack Publishing Company, Easton, Pa., 15th Edition, 1975. The composition or formulation to be administered will, in any event, contain a quantity of the active compound in an amount effective to alleviate the symptoms of the subject being treated.

Dosage forms or compositions containing active ingredient in the range of 0.005% to 95% with the balance made up from pharmaceutically acceptable carrier may be prepared.

For oral administration, a pharmaceutically acceptable composition is formed by the incorporation of any of the normally employed excipients, such as, for example pharmaceutical grades of mannicol, lactose, starch, magnesium stearate, talcum, povidone, cellulose derivatives, croscarmellose sodium, glucose, sucrose, magnesium carbonate, sodium saccharin, talcum and the like. Such compositions take the form of solutions, suspensions, tablets, capsules, powders, sustained release formulations and the like. Such compositions may contain 0.01%–95% active ingredient, preferably 0.1–50%.

For a solid dosage form containing liquid, the solution or suspension, in for example propylene carbonate, vegetable oils or triglycerides, is preferably encapsulated in a gelatin capsule. Such ester solutions, and the preparation and encapsulation thereof, are disclosed in U.S. Pat. Nos. 4,328,245; 4,409,239; and 4,410,545. For a liquid dosage form, the solution, e.g. in a polyethylene glycol, maybe diluted with a sufficient quantity of a pharmaceutically acceptable liquid carrier, e.g. water, to be easily measured for administration.

Alternatively, liquid or semi-solid oral formulations may be prepared by dissolving or dispersing the active compound or salt in vegetable oils, glycols, triglycerides, propylene glycol esters (e.g. propylene carbonate) and the like, and encapsulating these solutions or suspensions in hard or soft gelatin capsule shells.

Other useful formulations include those set forth in U.S. Pat. Nos. Re. 28,819 and 4,358,603.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, polyoxyethylene, sorbitan monolaurate, triethanolamine oleate, cyclodextrins, etc.

A more recently devised approach for parenteral administration employs the implantation of a slow-release or sustained-release system, such that a constant level of dosage is maintained. See, e.g., U.S. Pat. No. 3,710,795.

The percentage of active compound contained in such parenteral compositions is highly dependent on the specific nature thereof, as well as the activity of the compound and the needs of the subject. However, percentages of active ingredient of 0.01% to 10% in solution are employable, and will be higher if the composition is a solid which will be subsequently diluted to the above percentages. Preferably the composition will comprise 0.2–2% of the active agent in solution.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, preferably less than 10 microns.

EXAMPLES

The following examples are given to enable those skilled in the art to more clearly understand and to practice the present invention. They should not be considered as limiting the scope of the invention, but merely as being illustrative and representative thereof.

PREPARATION 1

Preparation of compounds of Formula 1

1A. Preparation of 1 Where S is ZA, in which $Z^1$ is Methyl, $Z^2$, $Z^3$, and $Z^4$ are Hydrogen, and G is Methoxy A solution of 15.1 g (47.1 mmol) of (E)-6-(1,3-dihydro-4-hydroxy-6-methoxy-7-methyl-3-oxoisobenzofuran-5-yl)-4-methyl-4-hexenoic acid (mycophenolic acid) and 0.7 g (3.7 mmol) of p-toluenesulfonic acid in 400 ml of methanol was allowed to stand at room temperature for 3 days. The mixture was concentrated under reduced pressure to approximately 75 ml and then partitioned between aqueous sodium bicarbonate and ethyl acetate. The organic phase was further washed with brine and then dried over sodium sulfate. Concentration of the organic phase under reduced pressure gave 15.4 g (46.0 mmol, 98%) of methyl (E)-6-(1,3-dihydro-4-hydroxy-6-methoxy-7-methyl-3-oxoisobenzofuran-5-yl)-4-methyl-4-hexenoate as a white solid, mp 104°–105° C.

1B. Preparation of 1, varying Z

Similarly, following the procedures of Preparation 1A above, but replacing (E)-6-(1,3-dihydro-4-hydroxy-6-methoxy-7-methyl-3-oxoisobenzofuran-5-yl)-4-methyl-4-hexenoic acid with:

(E)-6-(1,3-dihydro-4-hydroxy-6-methoxy-7-methyl-3-oxoisobenzofuran-5-yl)-2(RS), 4-dimethyl-4-hexenoic acid;

(E)-6-(1,3-dihydro-4-hydroxy- 6-methoxy-7-methyl-3-oxoisobenzofuran-5-yl)- 2(R), 4-dimethyl-4-hexenoic acid;

(E)-6-(1,3-dihydro-4-hydroxy-6-methoxy- 7-methyl-3-oxoisobenzofuran-5yl)- 2(S), 4-dimethyl-4-hexenoic acid;

(E)-6-(1,3-dihydro-4-hydroxy-6-methoxy- 7-methyl-3-oxoisobenzofuran-5-yl)- 3(RS), 4-dimethyl-4-hexenoic acid;

(E)-2-[2-[2-[1,3-dihydro- 4-hydroxy-6-methoxy-7-methyl- 3-oxoisobenzofuran- 5-yl] ethylidene]cyclopent-1(S)-yl]acetic acid;

(E)-2-[2-[2-[1,3-dihydro-4-hydroxy- 6-methoxy-7-methyl- 3-oxoisobenzofuran- 5-yl] ethylidene] cyclohex-1 (RS)-yl] acetic acid;

(E)-2-[2-[2-[1,3-dihydro-4-hydroxy- 6-methoxy-7-methyl -3-oxoisobenzofuran- 5-yl] ethylidene] cyclohex-1(S)-yl] acetic acid; and (E)-2-{ 4-[2-(1,3-dihydro-4-hydroxy- 6-methoxy-7-methyl -3-oxoisobenzofuran- 5-yl)ethylidene]tetrahydropyran-3(RS)-yl} acetic acid; and optionally replacing methanol by ethanol, the following intermediates of Formula 1 were prepared:

ethyl (E)-6-(1,3-dihydro-4-hydroxy-6-methoxy- 7-methyl -3-oxoisobenzofuran- 5-yl)-2(RS), 4-dimethyl-4-hexenoate, mp 59–63;

methyl (B)-6-(1,3-dihydro-4-hydroxy- 6-methoxy-7-methyl-3-oxoisobenzofuran- 5-yl}-2(R), 4-dimethyl-4-hexenoate;

methyl (E)-6-(1,3-dihydro-4-hydroxy- 6-methoxy-7-methyl-3 oxoisobenzofuran- 5-yl)-2(S), 4-dimethyl-4-hexenoate;

methyl (E)-6-(1,3-dihydro-4-hydroxy-6-methoxy- 7-methyl-3-oxoisobenzofuran-5-yl)-3(RS), 4-dimethyl-4-hexenoate;

methyl (E)-2-[2-[2-[1,3-dihydro-4-hydroxy- 6-methoxy-7-methyl-3-oxoisobenzofuran- 5-yl]ethylidene]cyclopent-1(S)-yl]acetate;

methyl (E)-2-[2-[2-[1,3-dihydro- 4-hydroxy-6-methoxy-7-methyl-3-oxoisobenzofuran- 5-yl] ethylidene]cyclohex-1(RS)-yl] acetate, mp 92°–99° C.;

ethyl (E)-2-[2-[2-[1,3-dihydro-4-hydroxy- 6-methoxy-7-methyl-3-oxoisobenzofuran- 5-yl]ethylidene]cyclohex-1(S)-yl]acetate, mp 72°–74° C.; and methyl (B)-2-{4-[2-(1,3-dihydro-4-hydroxy- 6-methoxy-7-methyl-3-oxoisobenzofuran- 5-yl)ethylidene]tetrahydropyran-3(RS)-yl} acetate.

1C. Preparation of 1, varying Z

Similarly, following the procedures of Preparation 1A above, but optionally replacing (E)-6-(1,3-dihydro-4-hydroxy- 6-methoxy-7-methyl-3-oxoisobenzofuran- 5-yl)-4-methyl-4-hexenoic acid with other compounds of Formula (1) where Z is a sidechain of Formula ZA, ZB, ZC, ZD, ZE, ZF. ZG, or ZH, in which G is hydroxy, and optionally replacing methanol with other alkanols of formula GH, where G is lower alkoxy, other intermediates of Formula 1 in which Z is a sidechain of Formula ZA, ZB, ZC, ZD, ZE, ZF. ZG, or ZH, in which G is lower alkoxy, are prepared.

PREPARATION 2

Preparation of Compounds of Formula 2

2A. Preparation of 2 where Z is ZA, in which $Z^1$ is Methyl, $Z^2$, $Z^3$, and $Z^4$ are Hydrogen, and G is Methoxy To a 0° C. solution of 4.59 g (13.7 mmol) of methyl (E)-6-(1,3-dihydro 4-hydroxy-6-methoxy-7-methyl- 3-oxoisobenzofuran-5-yl)-4-methyl-4-hexenoate and 2.22 ml (27.4 mmol) of pyridine in 100 ml of methylene chloride was added 2.55 ml (15.1 mmol) of trifluoromethanesulfonic anhydride dropwise. After 30 minutes, the reaction mixture was poured into 1N aqueous sodium hydrogen sulfate. This mixture was extracted with dichloromethane, and the organic phase was further washed with water and brine. The organic phase was dried over magnesium sulfate and concentrated under reduced pressure. Trituration of the residue with hexane gave 5.7 g of methyl (E)-6-(1,3-dihydro-6-methoxy-7-methyl-4-trifluoromethylsulfonyloxy-3-oxoisobenzofuran- 5-yl)-4-methyl-4-hexenoate as a white solid, mp 53°–55° C.

2B. Preparation of 2, varying Z

Similarly, following the procedures of Preparation 2A above, but replacing methyl (=)-6-(1,3-dihydro-4-hydroxy-6-methoxy-7-methyl-3-oxoisobenzofuran- 5-yl)-4-methyl-4-hexenoate with other compounds of Formula 1, the following intermediates of Formula 2 were prepared:

ethyl (E)-6-(1,3-dihydro-6-methoxy- 7-methyl-4-trifluoromethylsulfonyloxy- 3-oxoisobenzofuran-5-yl)-2(RS),4-dimethyl-4. hexenoate, oil;

methyl (E)-6-(1,3-dihydro- 6-methoxy-7-methyl-4-trifluoromethylsulfonyloxy- 3-oxoisobenzofuran-5-yl)-2(R),4-dimethyl-4-hexenoate;

methyl (B)-6-(1,3-dihydro- 6-methoxy-7-methyl-4-trifluoromethylsulfonyloxy- 3-oxoisobenzofuran-5-yl)-2(S),4-dimethyl-4-hexenoate;

methyl (E)-6-(1,3-dihydro-6-methoxy- 7-methyl-4-trifluoromethylsulfonyloxy- 3-oxoisobenzofuran-5-yl)-3(RS), 4-dimethyl-4-hexenoate;

ethyl (E)-2-[2-[2-[1,3-dihydro-6-methoxy-7-methyl-4-trifluoromethylsulfonyloxy- 3-oxoisobenzofuran-5-yl]ethylidene]cyclopent-1(S)-yl] acetate, oil;

methyl (E)-2-[2-[2-[1,3-dihydro- 6-methoxy-7-methyl-4-trifluoromethylsulfonyloxy- 3-oxoisobenzofuran-5-yl]ethylidene]cyclohex-1(RS)-yl] acetate, oil;

ethyl (E)-2-[2-[2-[1,3-dihydro- 6-methoxy-7-methyl-4-trifluoromethylsulfonyloxy- 3-oxoisobenzofuran-5-yl]ethylidene]cyclohex-1(S)-yl]acetate, oil; and methyl (E)-2-{4-[2-(1,3-dihydro- 6-methoxy-7-methyl-4 -trifluoromethylsulfonyloxy- 3-oxoisobenzofuran-5-yl)ethylidene] tetrahydropyran-3(RS)-yl} acetate.

2C. Preparation of 2, varying Z

Similarly, following the procedures of Preparation 2A above, but replacing methyl (E)-6-(1,3-dihydro-4-hydroxy-6-methoxy-7-methyl-3-oxoisobenzofuran- 5-yl)-4-methyl-4-hexenoate with other compounds of Formula 1 where Z is a sidechain of Formula ZA, ZB, ZC, ZD, ZE, ZF. ZG, or ZH, in which G is lower alkoxy, other intermediates of Formula 2 are prepared.

PREPARATION 3

Preparation of Compounds of Formula 3

3A. Preparation of 3 where Z is ZA, in which $Z^1$ is Methyl, $Z^2$, $Z^3$, and $Z^4$ are Hydrogen, and G is Methoxy A nitrogen-flushed mixture of 5.8 g (12.4 mmol) of methyl (E)-6-(1,3-dihydro- 6-methoxy-7-methyl-4-trifluoromethyl-sulfonyloxy-3-oxoisobenzofuran- 5-yl)-4-methyl-4-hexenoate, 1.5 g (23.0 mmol) of potassium cyanide, and 1.11 g (0.96 mmol) of tetrakis(triphenylphosphine) palladium in 100 ml of 1,4-dioxane was heated at reflux for 18 hours. Upon cooling, the mixture was partitioned between water and ethyl acetate. The organic phase was washed with water six times, with brine once, and then dried over magnesium sulfate. The solvent was evaporated under reduced pressure and the resulting solid was stirred with hexane for 18 hours and then filtered off. This solid was further purified by silica gel chromatography using 5:4 hexane:ethyl acetate to give 4.0 g (11.7 mmol) of methyl (E)-6-(4-cyano- 1,3-dihydro-6-methoxy-7-methyl-3-oxoisobenzofuran- 5-yl)-4-methyl-4hexenoate, mp 87°–88° C.

3B. Preparation of 3, varying Z

Similarly, following the procedures of Preparation 3A above, but replacing methyl (B)-6-(1,3-dihydro-6-methoxy-7-methyl-4-trifluoromethylsulfonyloxy- 3-oxoisobenzofuran-5-yl)-4-methyl-4-hexenoate with other compounds of Formula 2, the following intermediates of Formula 3 were prepared:

ethyl (E)-6-(4-cyano-1,3-dihydro- 6-methoxy-7-methyl-3-oxoisobenzofuran- 5-yl)-2(RS),4-dimethyl-4-hexenoate, mp 63°–66° C.;

methyl (E)-6-(4-cyano-1,3-dihydro-6-methoxy- 7-methyl -3 oxoisobenzofuran-5-yl)-2(R),4-dimethyl-4-hexenoate;

methyl (E)-6-(4-cyano-1,3-dihydro- 6-methoxy-7-methyl-3-oxoisobenzofuran-5-yl)- 2(S),4-dimethyl-4-hexenoate;

methyl (E)-6-(4-cyano-1,3-dihydro- 6-methoxy-7-methyl -3-oxoisobenzofuran- 5-yl)-3(RS),4-dimethyl -4-hexenoate;

ethyl (E)-2-[2-[2-[4-cyano- 1,3-dihydro-6-methoxy-7-methyl-3-oxoisobenzofuran- 5-yl]ethylidene]cyclopent-1(S)-yl] acetate, oil;

methyl (E)-2-[2-[2-[4-cyano- 1,3-dihydro-6-methoxy-7-methyl-3-oxoisobenzofuran- 5-yl]ethylidene] cyclohex-1(RS)-yl] acetate, mp 150°–151° C.;

ethyl (E)-2-[2-[2-[4-cyano- 1,3-dihydro-6-methoxy-7-methyl-3-oxoisobenzofuran- 5-yl]ethylidene]cyclohex-1(S)-yl]acetate, mp 126°–128° C.; and methyl (E)-2-{4-[2-(4-cyano-1,3-dihydro- 6-methoxy-7-methyl-3-oxoisobenzofuran- 5-yl)ethylidene] tetrahydropyran-3(RS )-yl} acetate.

3C. Preparation of 3, varying Z

Similarly, following the procedures of Preparation 3A above, but replacing methyl (g)-6-(1,3-dihydro-6-methoxy-7-methyl-4-trifluoromethylsulfonyloxy- 3-oxoisobenzofuran-5-yl)-4-methyl-4-hexenoate with other compounds of Formula 2, where Z is a sidechain of Formula ZA, ZB, ZC, ZD, ZE, ZF. ZG, or ZH, in which G is lower alkoxy, other intermediates of Formula 3 are prepared:

PREPARATION 4

Preparation of Compounds of Formula 4

4A. Preparation of 4 where Z is ZA. in which $Z^1$ is Methyl, $Z^2$, $Z^3$, and $Z^4$ are Hydrogen, and G is Hydroxy A mixture of 4.0 g (11.7 mmol) of methyl (E)-6-(4-cyano-1,3-dihydro- 6-methoxy-7-methyl-3-oxoisobenzofuran-5-yl)- 4-methyl-4-hexenoate and 1.86 g (46.5 mmol) of sodium hydroxide in 100 ml of 3:2 water:methanol was heated at reflux for 2 hours. The resulting homogenous solution was distilled until 30 ml of distillate was recovered. An additional 0.6 g (15 mmol) of sodium hydroxide was added to the reaction solution and it was refluxed for 2 days. Upon cooling the solution was partitioned between 1N aqueous HCl and ethyl acetate. The organic phase was washed twice with water, once with brine, and then dried over magnesium sulfate. The solvent was evaporated under reduced pressure to give a solid. This solid was stirred with hexane and then filtered off to give 3.88 g (11.1 mmol) of (E)-6-(4-carboxy- 1,3-dihydro-6-methoxy-7-methyl-3-oxoisobenzofuran- 5-yl)-4-methyl-4-hexenoic acid as a white solid, mp 172°–174° C.

4B. Preparation of 4, varying Z

Similarly, following the procedures of Preparation 4A above, but replacing methyl (E)-6-(1,3-dihydro-4-cyano-6-methoxy-7-methyl -3-oxoisobenzofuran- 5-yl)-4-methyl-4-hexenoate with other compounds of Formula 3, the following intermediates of Formula 4 were prepared:

(E)-6-(4-carboxy-1,3-dihydro-6-methoxy- 7-methyl -3-oxoisobenzofuran-5-yl)- 2 (RS),4-dimethyl-4-hexenoic acid, mp 149°–150° C.;

(E)-6-(4-carboxy-1,3-dihydro- 6-methoxy-7-methyl -3-oxoisobenzofuran-5-yl)- 2(R), 4-dimethyl-4-hexenoic acid;

(E)-6-(4-carboxy-1,3-dihydro-6-methoxy- 7-methyl-3-oxoisobenzofuran-5-yl)- 2(S), 4-dimethyl-4-hexenoic acid;

(E)-6-(4-carboxy-1,3-dihydro-6-methoxy- 7-methyl-3-oxoisobenzofuran-5-yl)- 3(RS), 4-dimethyl-4-hexenoic acid;

(E)-2-[2-[2-[4-carboxy- 1,3-dihydro-6-methoxy-7-methyl-3-oxoisobenzofuran- 5-yl] ethylidene] cyclopent-1(S)-yl] acetic acid, mp 142°–148° C.;

(E)-2-[2-[2-[4-carboxy-1,3-dihydro- 6-methoxy-7-methyl-3-oxoisobenzofuran- 5-yl]ethylidene]cyclohex-1(RS)-yl]acetic acid, mp 194°– 195° C.;

(E)-2-[2-[2-[4-carboxy-1,3-dihydro- 6-methoxy-7-methyl -3-oxoisobenzofuran-5-yl]ethylidene]cyclohex- 1(S)-yl] acetic acid, mp 193°–197° C.; and (E)-2-{4-[2-(4-carboxy- 1,3-dihydro-6-methoxy-7-methyl -3-oxoisobenzofuran- 5-yl) ethylidene]tetrahydropyran-3(RS)-yl} acetic acid.

4C. Preparation of 4, varying Z

Similarly, following the procedures of Preparation 4A above, but replacing methyl (E)-6-(4-cyano-1,3-dihydro-6-methoxy-7-methyl -3-oxoisobenzofuran- 5-yl)-4-methyl-4-hexenoate with other compounds of Formula 3 where Z is a sidechain of Formula ZA, ZB, ZC, ZD, ZE, ZF. ZG, or ZH, in which G is lower alkoxy, other intermediates of Formula 4 where G is hydroxy are prepared.

PREPARATION 5

Preparation of Compounds of Formula 5

5A. Preparation of 5 where Z is ZA, in which $Z^1$ is Methyl, $Z^2$, $Z^3$, and $Z^4$ are Hydrogen, and G is Methoxy A solution of 3.88 g (11.1 mmol) of (B)-6-( 4-carboxy-1,3-dihydro-6methoxy- 7-methyl -3-oxoisobenzofuran-5-yl)-4-methyl- 4-hexenoic acid and 0.2 g (1.0 mmol) of p-toluenesulfonic acid in methanol (60 ml) was stirred at room temperature for 8 hours. The solvent was evaporated under reduced pressure. The residue was dissolved in ethyl acetate, and this solution was washed twice with water, once with brine, and dried over magnesium sulfate. The solvent was evaporated under reduced pressure to give a solid which was recrystallized from ethyl acetate to give 3.37 g (9.3 mmol) of methyl (E)-6-(4-carboxy-1,3-dihydro-6-methoxy-7-methyl-3-oxoisobenzofuran-5-yl)-4-methyl- 4-hexenoate as a white solid, mp 169°–170° C.

5B. Preparation of 5, varying Z

Similarly, following the procedures of Preparation 5A above, but replacing (E)-6-(4-carboxy-1,3-dihydro- 6-methoxy-7-methyl-3-oxoisobenzofuran- 5-yl)-4-methyl-4-hexenoic acid with other compounds of Formula 4, the following intermediates of Formula 5 were prepared:

methyl (E)-6-(4-carboxy-1,3-dihydro-6-methoxy- 7-methyl-3-oxoisobenzofuran- 5-yl)-2(RS),4-dimethyl -4-hexenoate, mp 157°–159° C.;

methyl (E)-6-(4-carboxy-1,3-dihydro- 6-methoxy-7-methyl -3 oxoisobenzofuran-5-yl)- 2(R),4-dimethyl -4-hexenoate;

methyl (E)-6-(4-carboxy-1,3-dihydro- 6-methoxy-7-methyl-3 oxoisobenzofuran- 5-yl)-2(S),4-dimethyl-4-hexenoate;

methyl (E)-6-(4-carboxy-1,3-dihydro- 6-methoxy-7-methyl -3-oxoisobenzofuran- 5-yl)-3(RS),4-dimethyl-4-hexenoate;

methyl (E)-2-[2-[2-[4-carboxy- 1,3-dihydro-6-methoxy-7-methyl-3-oxoisobenzofuran- 5-yl]ethylidene] cyclopent-1(S)-yl] acetate, mp 145°–146° C.;

methyl (E)-2-[2-[2-[4-carboxy- 1,3-dihydro-6-methoxy-7-methyl-3-oxoisobenzofuran- 5-yl] ethylidene] cyclohex-1(RS)-yl] acetate, mp 155°–157° C.;

methyl (E)-2-[2-[2-[4-carboxy-1,3-dihydro- 6-methoxy-7-methyl-3-oxoisobenzofuran- 5-yl]ethylidene]cyclohex-1(S)-yl]acetate, mp 156°–157° C.; and methyl (E)-2-{4-[2-(4-carboxy- 1,3-dihydro-6-methoxy-7-methyl-3-oxoisobenzofuran- 5-yl)ethylidene]tetrahydropyran-3(RS)-yl} acetate.

5C. Preparation of 5. varying Z

Similarly, following the procedures of Preparation 5A above, but replacing (E)-6-(4-carboxy-1,3-dihydro- 6-methoxy-7-methyl-3-oxoisobenzofuran- 5-yl)-4-methyl-4-hexenoic acid with other compounds of Formula 4 where Z is a sidechain of Formula ZA, ZB, ZC, ZD, ZE, ZF. ZG, or ZH, in which G is hydroxy, and optionally replacing methanol with other alkanols of formula GH, where G is lower alkoxy, other intermediates of Formula 5 where G is lower alkoxy are prepared.

PREPARATION 6

Preparation of Compounds of Formula 6

6A. Preparation of 6 where Z is ZA, in which $Z^1$ is Methyl, $Z^2$, $Z^3$, end $Z^4$ are Hydrogen, and G is Methoxy To a stirred, 0° C. solution of 6.0 g (16.6 mmol) of methyl (E)-6-(4-carboxy- 1,3-dihydro-6-methoxy-7-methyl- 3-oxoisobenzofuran-5-yl).4-methyl-4-hexenoate in 150 ml of dimethylformamide was added 4.62 ml (33.1 mmol) of triethylamine followed by dropwise addition of 4.5 ml (21.8 mmol) of diphenylchlorophosphate. The mixture was allowed to stir at room temperature for 1 hour and then recooled to 0° C., and treated with 10.8 g (166 mmol) of sodium azide. This mixture was stirred for 24 hours at 0° C. and then partitioned between aqueous sodium hydrogen sulfate and ethyl acetate. The organic phase was washed four times with water, dried over magnesium sulfate, and concentrated under reduced pressure. The residue was triturated with hexane to give 5.8 g of methyl (E)-6-( 1,3-dihydro-4-isocyanato- 6-methoxy-7-methyl-3-oxoisobenzofuran-5-yl)-4-methyl-4-hexenoate. A small sample was further purified by rapid silica gel chromatography with an eluant of 1:1 hexane:ethyl acetate followed by recrystallization from hexane-ethyl acetate to give purified methyl (E)- 6(1,3-dihydro-4-isocyanato-6-methoxy-7-methyl- 3-oxoisobenzofuran-5-yl)-4-methyl- 4-hexenoate, mp 95°–101° C.

6B. Preparation of 6, varying Z

Similarly, following the procedures of Preparation 6A above, but replacing methyl (B)-6-(4-carboxy-1,3-dihydro-6-methoxy-7-methyl -3-oxoisobenzofuran- 5-yl)-4-methyl-4-hexenoate with other compounds of Formula 5, the following intermediates of Formula 6 were prepared:

methyl (R)-6-(1,3-dihydro-4-isocyanato- 6-methoxy-7-methyl-3-oxoisobenzofuran- 5-yl)-2(RS),4-dimethyl-4-hexenoate;

methyl-(1,3-dihydro-4-isocyanato-6-methoxy- 7-methyl-3-oxoisobenzofuran- 5-yl)-2 (R),4-dimethyl-4-hexenoate;

methyl (E)-6-(1, 3-dihydro-4-isocyanato- 6-methoxy-7-methyl -3 -oxoisobenzofuran- 5-yl)-2 (S),4-dimethyl-4-hexenoate;

methyl (E)-6-(1, 3-dihydro-4-isocyanato- 6-methoxy-7-methyl -3-oxoisobenzofuran- 5-yl)-3 (RS),4-dimethyl-4-hexenoate;

methyl (B)-2-[2-[2-[1,3-dihydro- 4-isocyanato-6-methoxy-7-methyl-3-oxoisobenzofuran- 5-yl] ethylidene] cyclopent-1(S)-yl] acetate;

methyl (E)-2-[2-[2-[1,3-dihydro- 4-isocyanato-6-methoxy-7-methyl -3-oxoisobenzofuran- 5-yl] ethylidene] cyclohex-1(RS)-yl]acetate;

methyl (E)-2-[2-[1,3-dihydro-4-isocyanato- 6-methoxy-7-methyl -3-oxoisobenzofuran- 5-yl]ethylidene] cyclohex-1(S)-yl] acetate; and methyl (E)-2-[ 2-(1,3-dihydro-4-isocyanato- 6-methoxy-7-methyl-3-oxoisobenzofuran- 5-yl) ethylidene] tetrahydropyran-3(RS)-yl}acetate.

6C. Preparation of 6. varying Z

Similarly, following the procedures of Preparation 6A above, but replacing methyl (E)-6-(4-carboxy-1,3-dihydro-6-methoxy-7-methyl-3-oxoisobenzofuran- 5-yl)-4-methyl-4-hexenoate with other compounds of Formula 5 where Z is a sidechain of Formula ZA, ZB, ZC, ZD, ZB, ZF. ZG, or ZH, in which G is lower alkoxy, other intermediates of Formula 6 where G is lower alkoxy are prepared.

Example 1

Preparation of Compounds of Formula I

Formula IA where Z is ZA, in which $Z^1$ is Methyl, $Z^2$, $Z^3$, and $Z^4$ are Hydrogen, and G is Hydroxy 9.0 g (5.5 mmol) of methyl (B)-6-( 4-carboxy-1,3-dihydro-6-methoxy-7methyl- 3-oxoisobenzofuran-5-yl)-4-methyl -4-hexenoate, a compound of Formula 5, was converted to crude methyl E-6-( 1,3-dihydro-4-isocyanato-6-methoxy-7-methyl-3-oxoisobenzofuran-5-yl)- 4-methyl-4-hexenoate, a compound of Formula 6, as described in Preparation 6 above without purification. The resulting 4-isocyanate was redissolved in 50 ml of 1,4-dioxane and treated with 16 ml of water and 2.0 g (47.7 mmol) of lithium hydroxide monohydrate. The mixture was stirred at room temperature for 2 hours and then partitioned between aqueous 1N sodium hydrogen sulfate and ethyl acetate. The organic phase was washed twice with water, once with brine, and was dried over magnesium sulfate. The solvent was evaporated under reduced pressure and the residue was purified by chromatography on silica gel, using 50:40:1 hexane:ethyl acetate:acetic acid as eluant to give 1.28 g (4.0 mmol) of (E)-6-(4-amino- 1,3-dihydro-6-methoxy-7-methyl-3-oxoisobenzofuran- 5-yl)-4-methyl-4-hexenoic acid as a white solid, mp 130°–131° C.

1B. Preparation of IA, varying $Z^b$

Similarly, following the procedures of Example 1A above, but replacing methyl E-6-(1,3-dihydro-4-isocyanato-6-methoxy-7-methyl-3-oxoisobenzofuran- 5-yl)-4-methyl-4-hexenoate with other compounds of Formula 6, in which $Z^a$ is as defined above, the following compounds of Formula IA in which $Z^b$ is as defined above were prepared:

(E)-6-(4-amino-1,3-dihydro- 6-methoxy-7-methyl -3-oxoisobenzofuran-5-yl)- 2(RS),4-dimethyl-4-hexenoic acid, mp 173°–174° C. (tert butylmethyl ether);

(E)-6-(4-amino-1,3-dihydro-6-methoxy- 7-methyl-3-oxoisobenzofuran-5-yl)- 2(R), 4-dimethyl-4-hexenoic acid, mp 133°–136° C. (tert butylmethyl ether/hexane);

(E)-6-(4-amino-1,3-dihydro-6-methoxy- 7-methyl-3-oxoisobenzofuran-5-yl)- 2(S),4-dimethyl-4-hexenoic acid, mp 133°–136° C. (tert butylmethyl ether);

(E)-6-(4-amino-1,3-dihydro-6-methoxy- 7-methyl -3-oxoisobenzofuran-5yl)- 3(RS),4-dimethyl-4-hexenoic acid;

(E)-2-[2-[2-[4-amino-1,3-dihydro- 6-methoxy-7-methyl-3-oxoisobenzofuran- 5-yl] ethylidene] cyclopent-1(S)-yl] acetic acid, mp 152°–153 ° C. (ethyl acetate/hexane);

(E)-2-[2-[2-[4-amino- 1,3-dihydro-6-methoxy-7-methyl -3-oxoisobenzofuran- 5-yl] ethylidene] cyclohex-1(RS}-yl] acetic acid, mp 163°–177° C. (tart butylmethyl ether/hexane);

(E)-2-[2-[2-[4-amino-1,3-dihydro- 6-methoxy-7-methyl-3-oxoisobenzofuran- 5-yl] ethylidene]cyclohex-1(S)-yl]acetic acid, mp 175°–177° C. (tert butylmethyl ether); and (E)-2-{4-[2-(4-amino-1,3-dihydro- 6-methoxy-7-methyl-3-oxoisobenzofuran- 5-yl) ethylidene]tetrahydropyran- 3(RS)-yl} acetic acid.

1C. Preparation of IA, varying Z in which G is Hydroxy

Similarly, following the procedures of Example 1A above, but replacing methyl E-6-(1,3-dihydro-4-isocyanato-6-methoxy-7-methyl-3-oxoisobenzofuran- 5-yl)-4-methyl-4-hexenoate with other compounds of Formula 6, in which $Z^a$ is a sidechain of Formula Z as defined in the Summary of the Invention in which G is lower alkoxy, the corresponding compounds of Formula IA in which G is hydroxy are prepared:

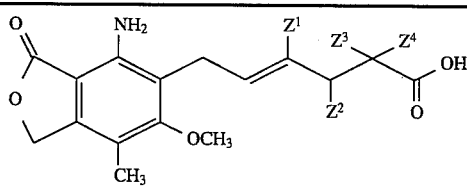

Formula IA where Z is Sidechain ZA

| $Z^1$ | $Z^2$ | $Z^3$ | $Z^4$ |
|---|---|---|---|
| Ethyl | H | H | Methyl |
| n-Propyl | H | H | Methyl |
| CF$_3$ | H | H | Methyl |
| H | H | H | Methyl |
| H | Methyl | H | Methyl |
| Methyl | Methyl | H | Methyl |
| Methyl | H | H | Methyl |
| Methyl | H | H | Ethyl |
| Methyl | H | H | n-Propyl |
| Methyl | Ethyl | H | H |
| Methyl | Ethyl | Methyl | Methyl |

-continued

| | | | |
|---|---|---|---|
| Methyl | H | Phenyl | H |
| Methyl | H | Phenyl | Methyl |
| Methyl | H | Methoxy | H |
| Methyl | H | Ethoxy | Ethyl |
| Methyl | H | Methylthio | H |
| Methyl | H | Ethylthio | Methyl |
| Methyl | H | Cyclopropyl | |
| Methyl | Methyl | H | H |

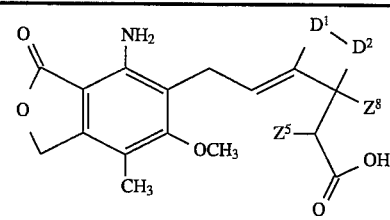

Formula IA where Z is Sidechain ZB

| $D^1$–$D^2$ | $Z^5$ | $Z^8$ |
|---|---|---|
| (CH$_2$)$_2$ | H | H |
| (CH$_2$)$_4$ | H | H |
| (CH$_2$)$_5$ | H | H |
| CH$_2$–O–CH$_2$ | H | H |
| (CH$_2$)$_2$–O–CH$_2$ | H | H |
| CH$_2$–S–CH$_2$ | H | Methyl |
| CH$_2$–NH–CH$_2$ | H | H |
| (CH$_2$)$_2$–O–CH$_2$ | H | Methyl |
| (CH$_2$)$_3$–O–CH$_2$ | H | H |
| (CH$_2$)$_2$ | Methyl | H |
| (CH$_2$)$_3$ | Methyl | H |
| (CH$_2$)$_3$ | Ethyl | H |
| (CH$_2$)$_3$ | n-Propyl | H |
| (CH$_2$)$_4$ | Methyl | H |
| (CH$_2$)$_4$ | Ethyl | Methyl |
| (CH$_2$)$_3$ | n-Hexyl | Methyl |

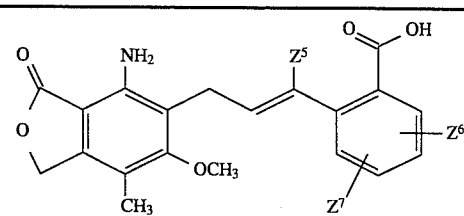

Formula IA where Z is Sidechain ZE

| $Z^5$ | $Z^6$ | $Z^7$ |
|---|---|---|
| H | H | H |
| H | 3-Methyl | H |
| H | 6-Methyl | H |
| H | 5-t-Butyl | H |
| H | 5-Methyl | 6-Methyl |
| H | 5-Methoxy | H |
| H | 4-COOH | H |
| H | 4-Chloro | H |
| H | 5-Chloro | H |
| H | 5-Bromo | 6-Bromo |
| H | 5-Nitro | H |
| H | 6-Nitro | H |
| Methyl | 3-Methyl | H |
| Methyl | 6-Methyl | H |
| Methyl | 5-t-Butyl | H |
| Methyl | 5-Methyl | 6-Methyl |
| Methyl | 5-Methoxy | H |
| Methyl | 4-COOH | H |
| Methyl | 4-Chloro | H |
| Methyl | 5-Chloro | H |
| Methyl | 5-Bromo | 6-Bromo |
| Methyl | 6-Nitro | H |
| n-Propyl | H | H |
| n-Propyl | 3-Methyl | H |
| n-Propyl | 6-Methyl | H |
| n-Propyl | 5-t-Butyl | H |

| n-Propyl | 5-Methyl | 6-Methyl |
| n-Propyl | 5-Methoxy | H |
| n-Propyl | 4-COOH | H |
| n-Propyl | 4-Chloro | H |
| n-Propyl | 5-Chloro | H |
| n-Propyl | 5-Bromo | 6-Bromo |
| n-Propyl | 6-Nitro | H |

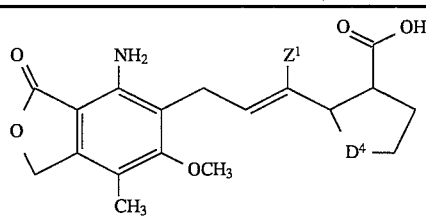

Formula IA where Z is Sidechain ZH

| D⁴ | Z¹ |
| --- | --- |
| $CH_2$ | Methyl |
| $O-CH_2$ | Methyl |
| $CH_2$ | Ethyl |
| $CH_2$ | n-Propyl |
| $(CH_2)_2$ | H |
| $(CH_2)_2$ | Methyl |
| $(CH_2)_2$ | Ethyl |
| $(CH_2)_3$ | H |
| $(CH_2)_3$ | Methyl |
| $CH_2$ | $CF_3$ |

Example 2

Preparation of Compounds of Formula I Formula IA where Z is ZA, in which $Z^1$ is Methyl, $Z^2$, $Z^3$, and $Z^4$ are Hydrogen, and G is Methoxy To a solution of 2.5 g (7.8 mmol) of (E)-6-( 4-amino-1, 3-dihydro-6-methoxy- 7-methyl-3-oxoisobenzofuran-5-yl)-4-methyl-4-hexenoic acid in 50 ml (1.234 mmol) of methanol was added 0.125 g (0.66 mmol) of p-toluenesulfonic acid monohydrate. The solution was stirred at room temperature for 2 days and then concentrated to a small volume. The residue was partitioned between water and ethyl acetate. The organic layer was dried over magnesium sulfate and concentrated to a solid. Recrystallization of this solid from hexane-ethyl acetate gave 2.48 g of methyl (E)-6-(4-amino-1,3-dihydro- 6-methoxy-7-methyl -3-oxoisobenzofuran-5-yl)-4-methyl-4-hexenoate, mp 91°–93° C.

2B. Preparation of IA, varying Z in which G is Lower Alkoxy

Similarly, following the procedures of Example 2A above, but optionally replacing (E)-6-(4-amino- 1,3-dihydro-6-methoxy-7-methyl -3-oxoisobenzofuran- 5-yl)-4-methyl-4-hexenoic acid with other compounds of Formula IA where Z is a sidechain of Formula ZA, ZB, ZC, ZD, ZE, ZF. ZG, or ZH, in which G is hydroxy, and optionally replacing methanol with other alkanols of formula GH, where G is lower alkoxy, the corresponding compounds of Formula IA where G is lower alkoxy are prepared.

Example 3

Preparation of Compounds of Formula I

3A. Formula IA where Z is ZA, in which $Z^1$ is Methyl, $Z^2$, $Z^3$, and $Z^4$ are Hydrogen, and G is Morpholinoethoxy 7g (0.02 moles) of (E)-6-(4-amino- 1,3-dihydro-6-methoxy-7-methyl-3-oxoisobenzofuran- 5-yl)-4-methyl-4-hexenoic acid and toluene (25ml) are warmed gently to form a solution. A slight excess (1.05 molar equivalents) of 2-morpholinoethanol (3 g, 0.021 moles) and toluene (25 ml) are added. The reaction mixture is stirred for half an hour and then heated to reflux at an initial pot temperature of 117° C. (which increases a few degrees during reflux) under a Dean-Stark trap for 80 hours. The reaction mixture is cooled, washed with water (2×15 ml), 10% aqueous sodium bicarbonate (2×15 ml) and finally with water (15 ml). The toluene layer is stripped to a volume of about 20 ml in vacuo, n-hexane (30 ml) is added and the resulting slurry is aged at room temperature for 2 hours. The product is filtered, washed with n-hexane (ca. 10 ml) and dried in. vacuo at 60° C. to yield 2-(morpholin-4-yl) ethyl (E)-6-(4-amino- 1,3-dihydro-6-methoxy-7-methyl-3-oxoisobenzofuran- 5-yl)-4-methyl-4-hexenoate.

3B. Preparation of IA, varying Z in which G is Morpholinoethoxy

Similarly, following the procedures of Example 3A above, but replacing (E)-6-(4-amino-1,3-dihydro-6-methoxy-7-methyl -3-oxoisobenzofuran- 5-yl)-4-methyl-4-hexenoic acid with other compounds of Formula IA where Z is a sidechain of Formula ZA, ZB, ZC, ZD, ZE, ZF. ZG, or ZH, in which G is hydroxy, the corresponding compounds of Formula IA where G is morpholinoethoxy are prepared.

Example 4

Preparation of Compounds of Formula I

4A. Formula IB where $R^4$ and $R^5$ are Methyl, and Z is ZA, in which $Z^1$ is Methyl, $Z^2$, $Z^3$, and $Z^4$ are Hydrogen, and G is Methoxy A solution of 0.65 g (1.8 mmol) of methyl (E)-6-( 1,3-dihydro-4-isocyanato-6-methoxy-7-methyl -3-oxoisobenzofuran- 5-yl)-4-methyl-4-hexenoate in 10 ml of tetrahydrofuran was treated with 5 ml of a solution of 40% dimethylamine in water. After 1 hour the reaction was partitioned between water and ethyl acetate. The organic phase was washed with water three times, dried over magnesium sulfate, and concentrated under reduced pressure to give 0.4 g of methyl (E)-6-[1,3-dihydro- 4-(3,3-dimethylureido)-6-methoxy-7-methyl- 3-oxoisobenzofuran-5-yl]-4-methyl-4-hexenoate, mp 116°–118° C.

4B. Preparation of IB, varying Z

Similarly, following the procedures of Example 4A above, but replacing methyl (E)-6-(1,3-dihydro-4-isocyanato-6-methoxy-7-methyl-3-oxoisobenzofuran- 5-yl)-4-methyl-4-hexenoate with other compounds of Formula 6 where Z is a sidechain of Formula ZA, ZB, ZC, ZD, ZE, ZF, ZG, or ZH, in which G is lower alkoxy, the corresponding compounds of Formula IB where G is lower alkoxy are prepared.

Example 5

Preparation of compounds of Formula I

5A. Formula IB where $R^4$ and $R^5$ are Methyl, and Z is ZA, in which $Z^1$ is Methyl, $Z^2$, $Z^3$, and $Z^4$ are Hydrogen, and G is Hydroxy To a solution of 0.3 g (0.74 mmol) of methyl (E)-6-[1,3-dihydro-4-(3,3-dimethylureido)-6-methoxy- 7-methyl-3-oxoisobenzofuran-5-yl]-4-methyl- 4-hexenoate in 7.4 ml of 4:1 methanol:water was added 0.13 g (2.96 mmol) of lithium hydroxide monohydrate. The solution was heated at 50°–60° C. for 4 hours. Upon cooling, the reaction was partitioned between aqueous sodium hydrogen sulfate and ethyl acetate. The organic layer was washed with brine, dried over magnesium sulfate, and concentrated to (E)- 6-[1,3-dihydro- 4-(3,3-dimethylureido)-6-methoxy-7-methyl- 3-oxoisobenzofuran-5-yl]- 4-methyl-4-hexenoic acid. Recrystallization from hexane-ethyl acetate gave 0.27 g (0.7 mmol) of (E)-6-[1,3-dihydro-4-( 3,3-dimethylureido)-6-methoxy-7-methyl- 3-oxoisobenzofuran-5-yl]-4-methyl- 4-hexenoic acid, mp 170°–190° C.

5B. Preparation of IB, varying $R^4$, $R^5$, and Z in which G is Hydroxy

Similarly, following the procedures of Example 5A above, but replacing methyl (B)-6-[1,3-dihydro-4-( 3,3-dimethylureido)-6-methoxy-7-methyl- 3-oxoisobenzofuran-5-yl]-4-methyl-4-hexenoate with other compounds of Formula IB where Z is a sidechain of Formula ZA, ZB, ZC, ZD, ZE, ZF, ZG, or ZH, in which G is lower alkoxy, the following compounds of Formula IB where G is hydroxy are prepared:

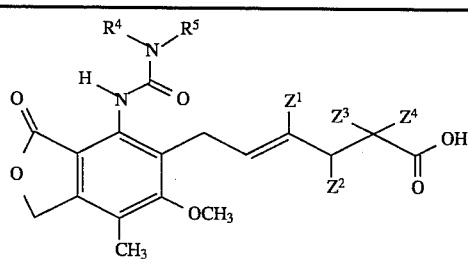

Formula IB where Z is Sidechain ZA

| $R^4$ | $R^5$ | $Z^1$ | $Z^2$ | $Z^3$ | $Z^4$ |
|---|---|---|---|---|---|
| H | H | Ethyl | H | H | Methyl |
| H | H | n-Propyl | H | H | Methyl |
| H | H | $CF_3$ | H | H | Methyl |
| H | Methyl | H | H | H | Methyl |
| H | Methyl | H | Methyl | H | Methyl |
| H | Methyl | Methyl | Methyl | H | Methyl |
| H | Methyl | Methyl | Ethyl | H | H |
| H | Methyl | Methyl | H | H | Ethyl |
| Methyl | Methyl | Methyl | H | H | n-Propyl |
| H | Methyl | Methyl | H | Cl | H |
| H | Methyl | Methyl | H | Cl | Methyl |
| H | H | Methyl | H | Phenyl | H |
| H | H | Methyl | H | Phenyl | Methyl |
| H | Methyl | Methyl | H | Methoxy | H |
| H | Methyl | Methyl | H | Ethoxy | Ethyl |
| H | Methyl | Methyl | H | $CH_3S$ | H |
| H | Methyl | Methyl | H | $C_2H_5S$ | Methyl |
| H | H | Methyl | H | Cyclopropyl | |
| H | H | Methyl | Methyl | H | H |

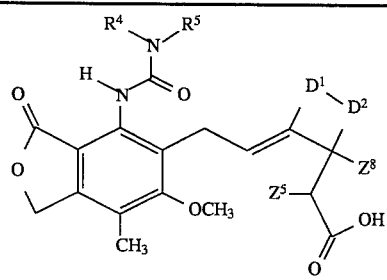

Formula IB where Z is Sidechain ZB

| $D^1-D^2$ | $R^4$ | $R^5$ | $Z^5$ | $Z^8$ |
|---|---|---|---|---|
| $(CH_2)_2$ | H | H | H | H |
| $(CH_2)_4$ | H | H | H | H |
| $(CH_2)_5$ | H | H | H | H |
| $CH_2-O-CH_2$ | H | H | H | H |
| $(CH_2)_2-O-CH_2$ | H | H | H | H |
| $CH_2-S-CH_2$ | H | Methyl | H | Methyl |
| $CH_2-NH-CH_2$ | H | Methyl | H | H |
| $(CH_2)_2-O-CH_2$ | Methyl | Methyl | H | Methyl |
| $(CH_2)_3-O-CH_2$ | Methyl | Methyl | H | H |
| $(CH_2)_2$ | H | Methyl | Methyl | H |
| $(CH_2)_3$ | H | Methyl | Methyl | H |
| $(CH_2)_3$ | H | Methyl | Ethyl | H |
| $(CH_2)_3$ | H | H | n-Propyl | H |
| $(CH_2)_4$ | H | H | Methyl | H |
| $(CH_2)_4$ | H | H | Ethyl | Methyl |
| $(CH_2)_3$ | H | H | n-Hexyl | Methyl |

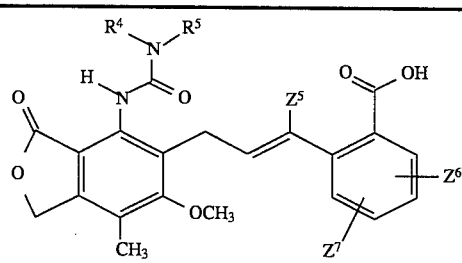

Formula IB where Z is Sidechain ZE

| $R^4$ | $R^5$ | $Z^5$ | $Z^6$ | $Z^7$ |
|---|---|---|---|---|
| H | H | H | H | H |
| H | H | H | 3-Methyl | H |
| H | H | H | 6-Methyl | H |
| H | H | H | 5-t-Butyl | H |
| H | Methyl | H | 5-Methyl | 6-Methyl |
| H | Methyl | H | 5-Methoxy | H |
| H | H | H | 4-COOH | H |
| H | H | H | 4-Chloro | H |
| H | Methyl | H | 5-Chloro | H |
| H | Methyl | H | 5-Bromo | 6-Bromo |
| H | Methyl | H | 5-Nitro | H |
| H | H | H | 6-Nitro | H |
| H | H | Methyl | 3-Methyl | H |
| H | Methyl | Methyl | 6-Methyl | H |
| H | H | Methyl | 5-t-Butyl | H |
| H | H | Methyl | 5-Methyl | 6-Methyl |
| H | Methyl | Methyl | 5-Methoxy | H |
| H | H | Methyl | 4-COOH | H |
| H | Methyl | Methyl | 4-Chloro | H |
| H | Methyl | Methyl | 5-Chloro | H |
| H | H | Methyl | 5-Bromo | 6-Bromo |
| H | Methyl | Methyl | 6-Nitro | H |
| H | H | n-Propyl | H | H |
| H | Methyl | n-Propyl | 3-Methyl | H |
| H | H | n-Propyl | 6-Methyl | H |
| H | H | n-Propyl | 5-t-Butyl | H |
| H | H | n-Propyl | 5-Methyl | 6-Methyl |
| H | H | n-Propyl | 5-Methoxy | H |
| H | H | n-Propyl | 4-COOH | H |
| H | H | n-Propyl | 4-Chloro | H |
| H | H | n-Propyl | 5-Chloro | H |
| H | H | n-Propyl | 5-Bromo | 6-Bromo |
| H | H | n-Propyl | 6-Nitro | H |

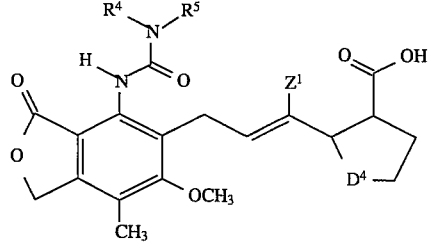

Formula IB where Z is Sidechain ZH

| $R^4$ | $R^5$ | $D^4$ | $Z^1$ |
|---|---|---|---|
| H | H | $CH_2$ | Methyl |
| H | H | $O-CH_2$ | Methyl |
| H | Methyl | $CH_2$ | Ethyl |
| H | Methyl | $CH_2$ | n-Propyl |
| H | H | $(CH_2)_2$ | H |

-continued

| | | | |
|---|---|---|---|
| H | Methyl | (CH$_2$)$_2$ | Methyl |
| H | H | (CH$_2$)$_2$ | Ethyl |
| H | Methyl | (CH$_2$)$_3$ | H |
| H | Methyl | (CH$_2$)$_3$ | Methyl |
| Methyl | Methyl | CH$_2$ | CF$_3$ |

Example 6

Preparation of Compounds of Formula I

6A. Formula IC where R$^3$ is —CH, or —CF$_3$, and Z is ZA, in which Z$^1$ is Methyl, Z$^2$, Z$^3$, and Z$^4$ are Hydrogen, and G is Methoxy To a solution of 0.5 g (1.5 mmol) of methyl (E)-6-(4-amino-1,3-dihydro- 6-methoxy-7-methyl-3-oxoisobenzofuran-5-yl)-4-methyl- 4-hexenoate in 5 ml of dichloromethane was added 0.5 ml (3.5 mmol) of trifluoroacetic anhydride. After 1 hour the reaction was partitioned between water and dichloromethane. The organic layer was washed twice with water, dried over magnesium sulfate, and concentrated to a solid. Recrystallization of this solid from hexane-ethyl acetate gave 0.520 g of methyl (E)-6-[1,3-dihydro 6-methoxy-7-methyl-4-trifluoroacetylamino- 3-oxoisobenzofuran-5-yl]-4-methyl- 4-hexenoate as a white solid, mp 107°–109° C.

6B. Formula IC where R$^1$ is —CF$_3$, and Z is ZA, in which Z Z$^3$, and Z$^4$ are Hydrogen, and G is Morpholinoethoxy By following the procedure of Example 3A above, but replacing E-6-(4-amino- 1,3-dihydro-6-methoxy-7-methyl -3-oxoisobenzofuran- 5-yl)-4-methyl-4-hexenoate, acid by (E)-6-[1,3-dihydro-6-methoxy-7-methyl- 4-trifluoroacetylamino- 3-oxoisobenzofuran-5-yl]-4-methyl-4-hexenoic acid, the following compound is obtained:

2-(morpholin-4-yl)ethyl (E)-6-[1,3-dihydro- 6-methoxy-7-methyl -4-trifluoroacetylamino- 3-oxoisobenzofuran-5-yl] -4-methyl-4-hexenoate.

6C. Formula IC where R$^3$ is —CF$_3$, and Z is ZA, in which Z$^2$ is Methyl, Z$^1$, Z$^3$, and Z$^4$ are Hydrogen, and G is Hydroxy By following the procedure of Example 6A above, but replacing methyl (E)-6-(4-amino-1,3-dihydro-6-methoxy-7-methyl-3-oxoisobenzofuran-5-yl)-b 4-methyl- 4-hexenoate by methyl (E)-6-[1,3-dihydro-amino- 6-methoxy-7-methyl-4-trifluoroacetylamino- 3-oxoisobenzofuran-5-yl]-4-methyl-4-hexenoate and methyl (E)-6-[4-acetamido-1,3-dihydro-6-methoxy- 7-methyl -3-oxoisobenzofuran- 5-yl]-4-methyl-4-hexenoate, the following compounds were obtained:

(E)-6-[1,3-dihydro-6-methoxy-7-methyl- 4-trifluoroacetylamino-3-oxoisobenzofuran- 5-yl]-4-methyl-4-hexenoic acid, mp 140°–141° C.; and (E)-6-[4-acetamido-1,3-dihydro-6-methoxy- 7-methyl -3-oxoisobenzofuran- 5-yl]-4-methyl-4-hexenoic acid, mp 206°–210° C.

6D. Preparation of IC, varying R$^3$ and Z

Similarly, following the procedures of Example 6A, 6B, and/or 6C above, but optionally replacing methyl (E)-6-(4-amino-1,3-dihydro- 6-methoxy-7-methyl- 3-oxoisobenzofuran-5-yl)-4-methyl-4-hexenoate with other compounds of Formula IA where Z is a sidechain of Formula ZA, ZB, ZC, ZD, ZE, ZF, ZG, or ZH, in which G is lower alkoxy, and replacing trifluoroacetic anhydride with other compounds of the formula (R$^3$C(O))$_2$O or of the formula R$^3$C(O)Cl, where R$^3$ is as defined in the Summary of the Invention, the following compounds of Formula IC where G is hydroxy are prepared:

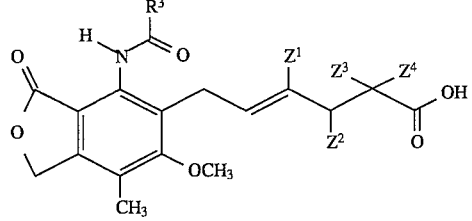

Formula IC where Z is Sidechain ZA

| R$^3$ | Z$^1$ | Z$^2$ | Z$^3$ | Z$^4$ |
|---|---|---|---|---|
| CF$_3$ | Ethyl | H | H | Methyl |
| CHF$_2$ | n-Propyl | H | H | Methyl |
| CH$_2$F | CF$_3$ | H | H | Methyl |
| CH$_3$ | H | H | H | Methyl |
| CF$_3$ | H | Methyl | H | Methyl |
| Phenyl | Methyl | Methyl | H | Methyl |
| CF$_3$ | Methyl | Ethyl | H | H |
| C$_2$H$_5$ | Methyl | H | H | Ethyl |
| CF$_3$ | Methyl | H | H | n-Propyl |
| CH$_3$ | Methyl | H | Phenyl | H |
| CHF$_2$ | Methyl | H | Phenyl | Methyl |
| CF$_3$ | Methyl | H | Methoxy | H |
| i-C$_3$H$_7$ | Methyl | H | Ethoxy | Ethyl |
| CF$_3$ | Methyl | H | CH$_3$S | H |
| CF$_3$ | Methyl | H | C$_2$H$_5$S | Methyl |
| CF$_3$ | Methyl | H | Cyclopropyl | |
| H | Methyl | Methyl | H | H |

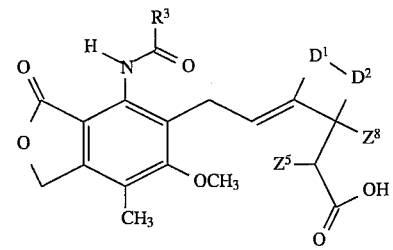

Formula IC where Z is Sidechain ZB

| D$^1$—D$^2$ | R$^3$ | Z$^5$ | Z$^8$ |
|---|---|---|---|
| (CH$_2$)$_2$ | CF$_3$ | H | H |
| (CH$_2$)$_4$ | CF$_3$ | H | H |
| (CH$_2$)$_5$ | CF$_3$ | H | H |
| CH$_2$—O—CH$_2$ | CF$_3$ | H | H |
| (CH$_2$)$_2$—O—CH$_2$ | CF$_3$ | H | H |
| CH$_2$—S—CH$_2$ | Methyl | H | Methyl |
| CH$_2$—NH—CH$_2$ | CH$_2$F | H | H |
| (CH$_2$)$_2$—O—CH$_2$ | CHF$_2$ | H | Methyl |
| (CH$_2$)$_3$—O—CH$_2$ | Phenyl | H | H |
| (CH$_2$)$_2$ | CF$_3$ | Methyl | H |
| (CH$_2$)$_3$ | CF$_3$ | Methyl | H |
| (CH$_2$)$_3$ | Ethyl | Ethyl | H |
| (CH$_2$)$_3$ | n-Propyl | n-Propyl | H |
| (CH$_2$)$_4$ | CF$_3$ | Methyl | H |
| (CH$_2$)$_4$ | i-Propyl | Ethyl | Methyl |
| (CH$_2$)$_3$ | n-Hexyl | n-Hexyl | Methyl |

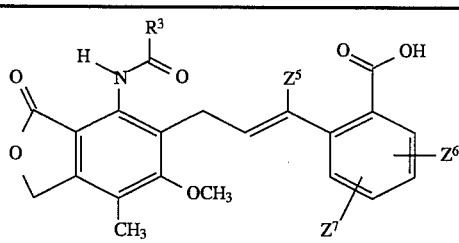

Formula IC where Z is Sidechain ZE

| R³ | Z⁵ | Z⁶ | Z⁷ |
|---|---|---|---|
| CF₃ | H | H | H |
| CF₃ | H | 3-Methyl | H |
| CF₃ | H | 6-Methyl | H |
| CF₃ | H | 5-t-Butyl | H |
| CHF₂ | H | 5-Methyl | 6-Methyl |
| CH₂F | H | 5-Methoxy | H |
| Methyl | H | 4-COOH | H |
| Ethyl | H | 4-Chloro | H |
| CF₃ | H | 5-Chloro | H |
| Phenyl | H | 5-Bromo | 6-Bromo |
| n-Propyl | H | 5-Nitro | H |
| CF₃ | H | 6-Nitro | H |
| CF₃ | Methyl | 3-Methyl | H |
| H | Methyl | 6-Methyl | H |
| CH₃ | Methyl | 5-t-Butyl | H |
| n-Hexyl | Methyl | 5-Methyl | 6-Methyl |
| CF₃ | Methyl | 5-Methoxy | H |
| CHF₂ | Methyl | 4-COOH | H |
| CH₂F | Methyl | 4-Chloro | H |
| CF₃ | Methyl | 5-Chloro | H |
| CF₃ | Methyl | 5-Bromo | 6-Bromo |
| CF₃ | Methyl | 6-Nitro | H |
| CF₃ | n-Propyl | H | H |
| CF₃ | n-Propyl | 3-Methyl | H |
| CF₃ | n-Propyl | 6-Methyl | H |
| CF₃ | n-Propyl | 5-t-Butyl | H |
| CF₃ | n-Propyl | 5-Methyl | 6-Methyl |
| CF₃ | n-Propyl | 5-Methoxy | H |
| CF₃ | n-Propyl | 4-COOH | H |
| CF₃ | n-Propyl | 4-Chloro | H |
| CF₃ | n-Propyl | 5-Chloro | H |
| CF₃ | n-Propyl | 5-Bromo | 6-Bromo |
| n-Hexyl | n-Propyl | 6-Nitro | H |

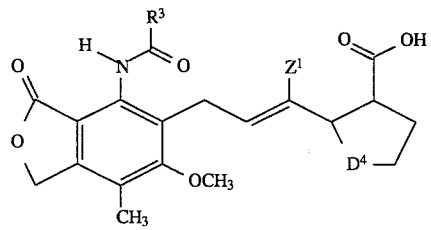

Formula IC where Z is Sidechain ZH

| R³ | D⁴ | Z¹ |
|---|---|---|
| CF₃ | CH₂ | Methyl |
| CF₃ | O—CH₂ | Methyl |
| CF₃ | CH₂ | Ethyl |
| CHF₂ | CH₂ | n-Propyl |
| Methyl | (CH₂)₂ | H |
| CF₃ | (CH₂)₂ | Methyl |
| CF₃ | (CH₂)₂ | Ethyl |
| CF₃ | (CH₂)₃ | H |
| CF₃ | (CH₂)₃ | Methyl |
| CF₃ | CH₂ | CF₃ |

Example 7

Preparation of Compounds of Formula I

7A. Formula ID where R¹ is Methyl, R³ is —CF₃, and Z is ZA, in which Z¹ is Methyl, Z², Z³, and Z⁴ are Hydrogen, and G is Methoxy To a solution of 0.35 g (0.82 mmol) of methyl (E)-6-[1, 3-dihydro-6-methoxy- 7-methyl-4-(trifluoroacetylamino)- 3-oxoisobenzofuran-5-yl]-4-methyl- 4-hexenoate in 4 ml of dimethylformamide was added 0.47 g (3.40 mmol) of potassium carbonate and 0.23 ml (3.69 mmol) of iodomethane. The mixture was stirred for 24 hours and then partitioned between ethyl acetate and water. The organic layer was washed with water, dried over magnesium sulfate, and concentrated under reduced pressure to give methyl (E)-6-[1,3-dihydro-6-methoxy-7-methyl- 4-(N-trifluoroacetyl-N-methylamino)- 3-oxoisobenzofuran-5-yl]-4-methyl- 4-hexenoate, an oil. NMR: δ 5.22–5.17 (multiplet ("m"), 2H); 5.10–5.04 (broad triplet, 1H); 3.81 (singlet ("s"), 3H); 3.62 (s, 3H); 3.42–3.27 (m, 5H); 2.45–2.25 (m, 5H); 1.75 (s, 3H).

7B. Preparation of ID, varying R¹, R², and Z

Similarly, following the procedures of Example 7A above, but optionally replacing methyl (E)-6-[1,3-dihydro-6-methoxy- 7-methyl-4-(trifluoroacetylamino)- 3-oxoisobenzofuran-5-yl]-4-methyl-4-hexenoate with other compounds of Formula IC where Z is a sidechain of Formula ZA, ZB, ZC, ZD, ZE, ZF, ZG, or ZH, in which G is lower alkoxy, and optionally replacing iodomethane by other lower alkyl halides of the formula R¹Br or R¹I, the following compounds of Formula ID are prepared:

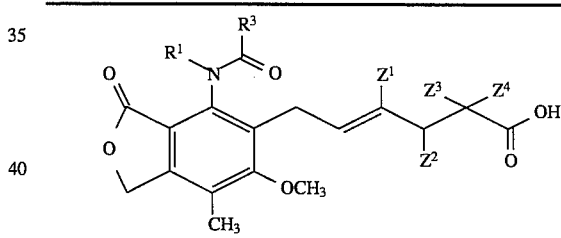

Formula ID where Z is Sidechain ZA

| R¹ | R³ | Z¹ | Z² | Z³ | Z⁴ |
|---|---|---|---|---|---|
| Methyl | CF₃ | Ethyl | H | H | Methyl |
| Methyl | CF₃ | n-Propyl | H | H | Methyl |
| Methyl | CF₃ | CF₃ | H | H | Methyl |
| Methyl | CF₃ | H | H | H | Methyl |
| Methyl | CF₃ | H | Methyl | H | Methyl |
| Methyl | CF₃ | Methyl | Methyl | H | Methyl |
| Methyl | CF₃ | Methyl | H | H | Methyl |
| Methyl | CF₃ | Methyl | H | H | Ethyl |
| Methyl | Methyl | Methyl | H | H | n-Propyl |
| Methyl | Ethyl | Methyl | Ethyl | H | H |
| Ethyl | n-Propyl | Methyl | Ethyl | H | Methyl |
| n-Propyl | Phenyl | Methyl | H | Phenyl | H |
| n-Butyl | CF₃ | Methyl | H | Phenyl | Methyl |
| t-Butyl | CF₃ | Methyl | H | Methoxy | H |
| n-Hexyl | CF₃ | Methyl | H | Ethoxy | Ethyl |
| Methyl | CF₃ | Methyl | H | CH₃S | H |
| Methyl | CF₃ | Methyl | H | C₂H₅S | Methyl |
| Methyl | CF₃ | Methyl | H | Cyclopropyl | |
| Methyl | H | Methyl | Methyl | H | H |

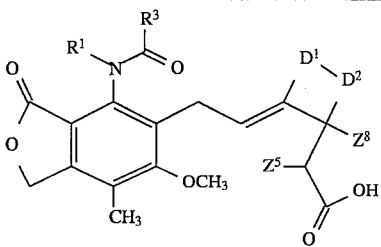

Formula ID where Z is Sidechain ZB

| $D^1-D^2$ | $R^1$ | $R^3$ | $Z^5$ | $Z^8$ |
|---|---|---|---|---|
| $(CH_2)_2$ | Methyl | $CF_3$ | H | H |
| $(CH_2)_4$ | Methyl | $CF_3$ | H | H |
| $(CH_2)_5$ | Methyl | $CF_3$ | H | H |
| $CH_2-O-CH_2$ | Methyl | $CF_3$ | H | |
| $(CH_2)_2-O-CH_2$ | Methyl | $CF_3$ | H | H |
| $CH_2-S-CH_2$ | Methyl | $CF_3$ | H | Methyl |
| $CH_2-NH-CH_2$ | Methyl | Methyl | H | H |
| $(CH_2)_2-O-CH_2$ | Methyl | Ethyl | H | Methyl |
| $(CH_2)_3-O-CH_2$ | Methyl | Ethyl | H | Methyl |
| $(CH_2)_2$ | Ethyl | Propyl | Methyl | H |
| $(CH_2)_3$ | n-Propyl | Hexyl | Methyl | H |
| $(CH_2)_3$ | n-Butyl | $CF_3$ | Ethyl | H |
| $(CH_2)_3$ | t-Butyl | $CF_3$ | n-Propyl | H |
| $(CH_2)_4$ | Hexyl | Phenyl | Methyl | H |
| $(CH_2)_4$ | Methyl | $CF_3$ | Ethyl | Methyl |
| $(CH_2)_3$ | Methyl | H | n-Hexyl | Methyl |

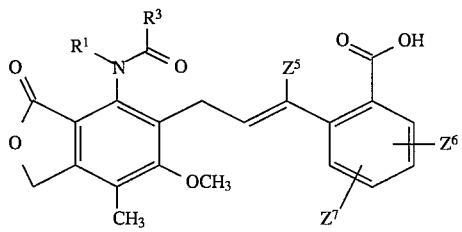

Formula ID where Z is Sidechain ZE

| $R^1$ | $R^3$ | $Z^5$ | $Z^6$ | $Z^7$ |
|---|---|---|---|---|
| Methyl | $CF_3$ | H | H | H |
| Methyl | $CHF_2$ | H | 3-Methyl | H |
| Methyl | $CH_2F$ | H | 6-Methyl | H |
| Methyl | Methyl | H | 5-t-Butyl | H |
| Methyl | Ethyl | H | 5-Methyl | 6-Methyl |
| Methyl | n-Propyl | H | 5-Methoxy | H |
| Methyl | Phenyl | H | 4-COOH | H |
| Methyl | $CF_3$ | H | 4-Chloro | H |
| Methyl | $CHF_2$ | H | 5-Chloro | H |
| Ethyl | $CH_2F$ | H | 5-Bromo | 6-Bromo |
| n-Propyl | $CF_3$ | H | 5-Nitro | H |
| n-Butyl | Methyl | H | 6-Nitro | H |
| Methyl | H | Methyl | 3-Methyl | H |
| Methyl | $CH_3$ | Methyl | 6-Methyl | H |
| Methyl | $CF_3$ | Methyl | 5-t-Butyl | H |
| Methyl | $CF_3$ | Methyl | 5-Methyl | 6-Methyl |
| Methyl | $CF_3$ | Methyl | 5-Methoxy | H |
| Methyl | $CF_3$ | Methyl | 4-COOH | H |
| Methyl | $CF_3$ | Methyl | 4-Chloro | H |
| Methyl | $CF_3$ | Methyl | 5-Chloro | H |
| Methyl | $CF_3$ | Methyl | 5-Bromo | 6-Bromo |
| Methyl | $CF_3$ | Methyl | 6-Nitro | H |
| Methyl | $CF_3$ | n-Propyl | H | H |
| Methyl | $CF_3$ | n-Propyl | 3-Methyl | H |
| Methyl | $CF_3$ | n-Propyl | 6-Methyl | H |
| Methyl | $CF_3$ | n-Propyl | 5-t-Butyl | H |
| Methyl | $CF_3$ | n-Propyl | 5-Methyl | 6-Methyl |
| Methyl | $CF_3$ | n-Propyl | 5-Methoxy | H |
| Methyl | $CF_3$ | n-Propyl | 4-COOH | H |
| Methyl | $CF_3$ | n-Propyl | 4-Chloro | H |
| Methyl | $CF_3$ | n-Propyl | 5-Chloro | H |
| Methyl | $CF_3$ | n-Propyl | 5-Bromo | 6-Bromo |
| Methyl | $CF_3$ | n-Propyl | 6-Nitro | H |

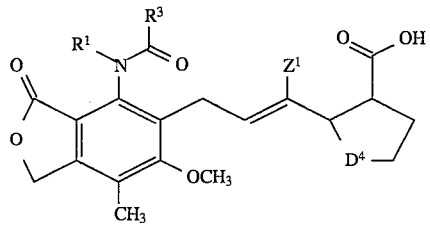

Formula ID where Z is Sidechain ZH

| $R^1$ | $R^3$ | $D^4$ | $Z^1$ |
|---|---|---|---|
| Methyl | $CF_3$ | $CH_2$ | Methyl |
| Methyl | $CF_3$ | $O-CH_2$ | Methyl |
| Methyl | $CF_3$ | $CH_2$ | Ethyl |
| Methyl | $CF_3$ | $CH_2$ | n-Propyl |
| Ethyl | $CF_3$ | $(CH_2)_2$ | H |
| n-Propyl | $CF_3$ | $(CH_2)_2$ | Methyl |
| N-Butyl | $CF_3$ | $(CH_2)_2$ | Ethyl |
| Methyl | $CF_3$ | $(CH_2)_3$ | H |
| Methyl | $CF_3$ | $(CH_2)_3$ | Methyl |
| Methyl | $CF_3$ | $CH_2$ | $CF_3$ |

7C. Preparation of ID, varying $R^1$, $R^3$, and Z

Hydrolysis of the compounds of Formula ID where G is lower alkoxy to compounds of Formula ID where G is hydroxy is accomplished as shown in Example 5A above.

Conversion of the compounds of Formula ID where G is hydroxy to compounds of Formula ID where G is lower alkoxy or morpholinoethoxy is accomplished as shown in Example 2A or 6B above.

Example 8

Preparation of Compounds of Formula I

8A. Formula IE where $R^1$ is Methyl and Z is ZA, in which $Z^1$ is Methyl, $Z^2$, $Z^3$, and $Z^4$ are Hydrogen, and G is Hydroxy Hydrolysis of (E)-6-[1,3-dihydro- 6-methoxy-7-methyl-4-(N-trifluoroacetyl-N-methylamino)- 3-oxoisobenzofuran-5-yl]-4-methyl-4-hexenoic acid was carried on the same manner as shown in Example 5A, to give (E)-6-(1,3-dihydro-6-methoxy- 7-methyl-4-methylamino-3-oxoisobenzofuran- 5-yl)-4-methyl-4-hexenoic acid, mp 121°–124° C.

8B. Preparation of IE, varying $R^1$ and Z

Similarly, following the procedures of Example 8A above, but replacing (E)-6-[1,3-dihydro-6-methoxy- 7-methyl-4-(N-trifluoroacetyl-N-methylamino)- 3-oxoisobenzofuran-5-yl]-4-methyl- 4-hexenoic acid with other compounds of Formula ID where Z is a sidechain of Formula ZA, ZB, ZC, ZD, ZE, ZF, ZG, or ZH, in which G is lower alkoxy or hydroxy, the following compounds of Formula IE are prepared:

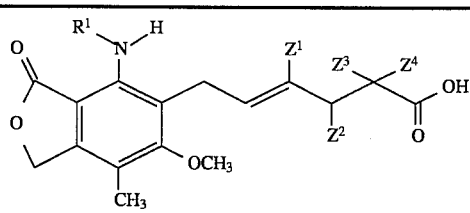

Formula IE where Z is Sidechain ZA

| R¹ | Z¹ | Z² | Z³ | Z⁴ |
|---|---|---|---|---|
| Methyl | Ethyl | H | H | Methyl |
| Methyl | n-Propyl | H | H | Methyl |
| Methyl | CF₃ | H | H | Methyl |
| Methyl | H | H | H | Methyl |
| Methyl | H | Methyl | H | Methyl |
| Methyl | Methyl | Methyl | H | Methyl |
| Methyl | Methyl | H | H | Methyl |
| Methyl | Methyl | H | H | Ethyl |
| Methyl | Methyl | H | H | n-Propyl |
| Methyl | Methyl | Ethyl | H | H |
| Ethyl | Methyl | Ethyl | H | Methyl |
| n-Propyl | Methyl | H | Phenyl | H |
| N-Butyl | Methyl | H | Phenyl | Methyl |
| Methyl | Methyl | H | Methoxy | H |
| Methyl | Methyl | H | Ethoxy | Ethyl |
| Methyl | Methyl | H | CH₃S | H |
| Methyl | Methyl | H | C₂H₅S | Methyl |
| Methyl | Methyl | H | Cyclopropyl | |
| Methyl | Methyl | Methyl | H | H |

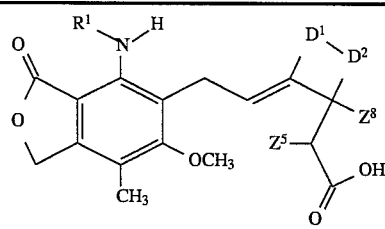

Formula IE where Z is Sidechain ZB

| D¹–D² | R³ | Z⁵ | Z⁸ |
|---|---|---|---|
| (CH₂)₂ | CF₃ | H | H |
| (CH₂)₄ | CF₃ | H | H |
| (CH₂)₅ | CF₃ | H | H |
| CH₂–O–CH₂ | CF₃ | H | H |
| (CH₂)₂–O–CH₂ | CF₃ | H | H |
| CH₂–S–CH₂ | CF₃ | H | Methyl |
| CH₂–NH–CH₂ | Methyl | H | H |
| (CH₂)₂–O–CH₂ | Ethyl | H | Methyl |
| (CH₂)₃–O–CH₂ | n-Propyl | H | H |
| (CH₂)₂ | n-Hexyl | Methyl | H |
| (CH₂)₃ | CHF₂ | Methyl | H |
| (CH₂)₃ | CH₂F | Ethyl | H |
| (CH₂)₃ | CF₃ | n-Propyl | H |
| (CH₂)₄ | CF₃ | Methyl | H |
| (CH₂)₄ | CF₃ | Ethyl | Methyl |
| (CH₂)₃ | CF₃ | n-Hexyl | Methyl |

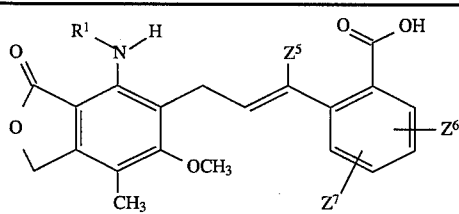

Formula IE where Z is Sidechain ZE

| R¹ | Z⁵ | Z⁶ | Z⁷ |
|---|---|---|---|
| Methyl | H | H | H |
| Methyl | H | 3-Methyl | H |
| Methyl | H | 6-Methyl | H |
| Methyl | H | 5-t-Butyl | H |
| Methyl | H | 5-Methyl | 6-Methyl |
| Methyl | H | 5-Methoxy | H |
| Methyl | H | 4-COOH | H |
| Methyl | H | 4-Chloro | H |
| Methyl | H | 5-Chloro | H |
| Ethyl | H | 5-Bromo | 6-Bromo |
| n-Propyl | H | 5-Nitro | H |
| n-Butyl | H | 6-Nitro | H |
| Methyl | Methyl | 3-Methyl | H |
| Methyl | Methyl | 6-Methyl | H |
| Methyl | Methyl | 5-t-Butyl | H |
| Methyl | Methyl | 5-Methyl | 6-Methyl |
| Methyl | Methyl | 5-Methoxy | H |
| Methyl | Methyl | 4-COOH | H |
| Methyl | Methyl | 4-Chloro | H |
| Methyl | Methyl | 5-Chloro | H |
| Methyl | Methyl | 5-Bromo | 6-Bromo |
| Methyl | Methyl | 6-Nitro | H |
| Methyl | n-Propyl | H | H |
| Methyl | n-Propyl | 3-Methyl | H |
| Methyl | n-Propyl | 6-Methyl | H |
| Methyl | n-Propyl | 5-t-Butyl | H |
| Methyl | n-Propyl | 5-Methyl | 6-Methyl |
| Methyl | n-Propyl | 5-Methoxy | H |
| Methyl | n-Propyl | 4-COOH | H |
| Methyl | n-Propyl | 4-Chloro | H |
| Methyl | n-Propyl | 5-Chloro | H |
| Methyl | n-Propyl | 5-Bromo | 6-Bromo |
| Methyl | n-Propyl | 6-Nitro | H |

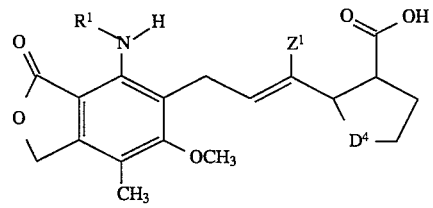

Formula IE where Z is Sidechain ZH

| R¹ | D⁴ | Z¹ |
|---|---|---|
| Methyl | CH₂ | Methyl |
| Methyl | O–CH₂ | Methyl |
| Methyl | CH₂ | Ethyl |
| Methyl | CH₂ | n-Propyl |
| Ethyl | (CH₂)₂ | H |
| n-Propyl | (CH₂)₂ | Methyl |
| N-Butyl | (CH₂)₂ | Ethyl |
| Methyl | (CK₂)₃ | H |
| Methyl | (CH₂)₃ | Methyl |
| Methyl | CH₂ | CF₃ |

Conversion of the compounds of Formula IB where G is hydroxy to compounds of Formula IR where G is lower alkoxy or morpholinoethoxy is accomplished as shown in Examples 2A or 6B above.

Example 9

This example illustrates the preparation of a representative pharmaceutical formulation for oral administration containing an active compound of Formula I, e.g., (R)-6-(1,3-dihydro-4-amino- 6-methoxy-7-methyl-3-oxoisobenzofuran-B-yl)-2,4-dimethyl-4-hexenoic acid.

| Ingredients | Quantity per tablet, mgs. |
|---|---|
| Active Compound | 200 |
| Lactose, spray-dried | 148 |
| Magnesium stearate | 2 |

The above ingredients are mixed and introduced into a hard-shell gelatin capsule.

Other compounds of Formula I, such as those prepared in accordance with Examples 1–8, can be used as the active compound in the preparation of the orally administrable formulations of this example.

This example illustrates the preparation of another representative pharmaceutical formulation for oral administration containing an active compound of Formula I, e.g., (E)-6-(1, 3-dihydro-4-amino- 6-methoxy-7-methyl- 3-oxoisobenzofuran-5-yl)-2,4-dimethyl-4-hexenoic acid.

| Ingredients | Quantity per tablet, mgs. |
|---|---|
| Active Compound | 400 |
| Cornstarch | 50 |
| Croscarmellose sodium | 25 |
| Lactose | 120 |
| Magnesium stearate | 5 |

The above ingredients are mixed intimately and pressed into single scored tablets.

Other compounds of Formula I, such as those prepared in accordance with Examples 1–8, can be used as the active compound in the preparation of the orally administrable formulations of this example.

Example 11

This example illustrates the preparation of a representative pharmaceutical formulation containing an active compound of Formula I, e.g., (E)-6-(1,3-dihydro-4-amino-6-methoxy- 7-methyl-3-oxoisobenzofuran-5-yl)- 2,4-dimethyl-4-hexenoic acid.

An oral suspension is prepared having the following composition.

| Ingredients | |
|---|---|
| Active Compound | 1.0 g |
| Fumaric acid | 0.5 g |
| Sodium chloride | 2.0 g |
| Methyl paraben | 0.15 g |
| Propyl paraben | 0.05 g |
| Granulated sugar | 25.5 g |
| Sorbitol (70% solution) | 12.85 g |
| Veegum K (Vanderbilt Co.) | 1.0 g |
| Flavoring | 0.035 ml |
| Colorings | 0.5 mg |
| Distilled water q.s. to | 100 ml |

Other compounds of Formula I, such as those prepared in accordance with Examples 1–8, can be used as the active compound in the preparation of the orally administrable formulations of this example.

Example 12

This example illustrates the preparation of a representative pharmaceutical formulation for oral administration containing an active compound of Formula I, e.g., (E)-6-(1,3-dihydro-4-amino- 6-methoxy-7-methyl-3-oxoisobenzofuran-5-yl)-2,4-dimethyl-4-hexenoic acid.

An injectable preparation buffered to a suitable pH is prepared having the following composition:

| Ingredients | |
|---|---|
| Active Compound | 0.2 g |
| Sodium Acetate Buffer Solution (0.4 M) | 2.0 ml |
| HCL (1N) or NaOH (1N) q.s. to | pH 4 |
| Water (distilled, sterile) q.s. to | 20 ml |

Other compounds of Formula I, such as those prepared in accordance with Examples 1–8, can be used as the active compound in the preparation of the injectable formulations of this example.

Example 13

This example illustrates the preparation of a representative pharmaceutical formulation for topical application containing an active compound of Formula I, e.g., (g)-6-(1,3-dihydro- 4-amino-6-methoxy-7-methyl 3-oxoisobenzofuran-5-yl)-2,4-dimethyl -4-hexenoic acid.

| Ingredients | grams |
|---|---|
| Active compound | 0.2–10 |
| Span 60 | 2 |
| Tween 60 | 2 |
| Mineral oil | 5 |
| Petrolatum | 10 |
| Methyl paraben | 0.15 |
| Propyl paraben | 0.05 |
| BHA (butylated hydroxy anisole) | 0.01 |
| Water q.s. to | 100 |

All of the above ingredients, except water, are combined and heated to 60° C. with stirring. A sufficient quantity of water at 60° C. is then added with vigorous stirring to emulsify the ingredients, and water then added q.s. 100 g.

Other compounds of Formula I, such as those prepared in accordance with Examples 1–8, can be used as the active compound in the preparation of the topical formulations of this example.

Example 14

This example illustrates the preparation of a representative pharmaceutical formulation containing an active compound of Formula I, e.g., (E)-6-(1,3-dihydro-4-amino-6-methoxy- 7-methyl-3-oxoisobenzofuran-5-yl)- 2,4-dimethyl-4-hexenoic acid.

A suppository totalling 2.5 grams is prepared having the following composition:

| Ingredients | |
|---|---|
| Active Compound | 500 mg |
| Witepesol H-15* | balance |

(*triglycerides of saturated vegetable fatty acid; a product of Riches-Nelson, Inc., New York, N.Y.)

Other compounds of Formula I, such as those prepared in accordance with Examples 8–22, can be used as the active compound in the preparation of the suppository formulations of this example.

Example 15

In Vitro Determination of Therapeutic Activity (As an Anti-Inflammatory, Anti-Viral, Anti-Tumor, Anti-Psoriatic and/or Immunosuppressive Agent) Utilizing the Inhibition of IMP Dehydrogenase Assay This assay is a modification of the method of Anderson, J. H. and Sartorelli, A. C., *Jour. Biol. Chem*, 243:4762–4768 (1968). It measures the formation of NADH ($\lambda_{max}$=340 nm, $\epsilon 340$=6,220 $M^1 cm^{-1}$) as Inosine 5'-monophosphate ("IMP") is converted to Xanthosine 5'-monophosphate ("XMP") by the human Type II IMP dehydrogenase ("IMPDH").

Compounds are dissolved and diluted in DMSO, and reaction solutions containing compounds at 0, 0.01, 0.10, 1.0, 10, and 100 µM are prepared in disposable methacrylic plastic microcuvets ('UV-transparent' plastic, 1 cm pathlength, 1.5 ml capacity). The solutions (0.5–1 ml) contain the following: 0.1 M TrisHCL, pH 8.0; 0.1 M KCL; 3.0 mM EDTA; 100 µg/ml BSA; 0.05 mM IMP; 0.10 mM NAD; 10% DMSO; 5–15 nM IMPDH (0.003–0.010 units/ml; one unit of enzyme catalyzes the formation of one µmol NADH per minute at 40° C. at saturating substrate concentrations—200 µM IMP and 400 µM NAD). Reactions are performed at 40° C. and initiated by the addition of enzyme. Mycophenolic acid ($IC_{50}$≈0.02 µM) serves as the positive control. The reactions are monitored at 340 nm for 10 minutes in a UV/VIS spectrophotometer, and rate data are collected.

The 50% inhibitory value ("$IC_{50}$") is determined by fitting the fractional activities relative to control to the following equation on a Macintosh computer by the program Systat:

Fractional activity= $MAX/((X/IC_{50})^n+1)$

X is the concentration of the compound, and the term n accounts for deviations of the data from a simple competitive inhibition model.

The compounds of the present invention inhibit IMPDH when tested by this method, indicating their activity as anti-inflammatory, anti-viral, anti-tumor, anti-psoriatic and/or immunosuppressive agents.

Example 16

In Vitro Determination of Immunosuppressive Activity Utilizing Responses of Human Peripheral Blood Lymphocytes to T-and B-cell Mitogens This procedure is a modification of a procedure initially described by Greaves, et al. ["Activation of human T and B lymphocytes by polyclonal mitogens," Nature, 248:698–701 (1974)].

Human mononuclear cells ("PBL") are separated from heparinized whole blood by density gradient centrifugation in Ficoll-Plaque (Pharmacia). After washing, 2×10⁵ cells/well are cultured in microtiter plates with RPMI 1640 supplemented with 5% fetal calf serum, penicillin and streptomycin. PHA (Sigma) at 10 µg/ml is then added. Test materials are tested at concentrations between $10^4$ and $10^8 M$, by addition to the culture at time 0. Cultures are set up in quadruplicate and incubated at 37° C. in a humidified atmosphere with 7% $CO_2$ for 72 hours. A pulse of 0.5 µCi/well of ³H-thymidine is added for the last 6 hours. Cells are collected on glass fiber filters with an automatic harvester and radioactivity is measured by standard scintillation procedures. The 50% inhibitory concentration ("$IC_{50}$") for mitogenic stimulation is determined graphically.

To evaluate differential effects on T-and B-lymphocytes, different mitogens are used: PWM (Sigma) at 20 µg/ml and Staphylococcus Protein A bound to Sepharose (SPA) (Sigma) 2 mg/ml or 14 µg/ml of Protein A.

The compounds of the present invention show immunosuppressive activity when tested by this method.

Example 17

Determination of Immunosuppressive Activity Utilizing the Hemolytic Plaque Forming Cell Assay This procedure is a modification of "The agar plaque technique for recognizing antibody producing cells," a procedure initially described by Jerne et al., [*Cellbound Antibodies*, Amos and Kaprowski editors (Wistar Institute Press, Philadelphia, 1963), p. 109].

Groups of 5–6 adult C578B1/6 male mice were sensitized with 1×10⁸ sheep red blood cells ("SRBC") and simultaneously treated with an oral dosage form of the test material in an aqueous vehicle. Animals in a control group receive the same volume of vehicle. Four days after SRBC inoculation, spleens are dispersed in loose Ten Broeck homogenizers. The number of nucleated cells ("WBC") is determined and the spleen cell suspension is mixed with SRBC, guinea pig complement and agar solution at 0.5% concentration. Aliquots of the above mixture (0.1 ml) are dropped on four separate quadrants of a Petri dish and are covered with cover slips. After two hours incubation at 37° C., areas of hemolysis around plaque-forming cells ("PFC") are counted with a dissecting microscope. Total WBC/spleen, PFC/spleen and PFC/10⁶ WBC ("PPM") are calculated for each mouse spleen. Geometric means of each treatment group are then compared with the vehicle-treated control group.

The compounds of the present invention show immunosuppressive activity when tested by this method.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed:

1. A compound represented by the formula:

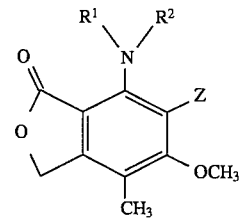

wherein:

$R^1$ is hydrogen or lower alkyl;

$R^2$ is hydrogen, lower alkyl, —C(O)$R^3$, —C(O)NR⁴R⁵, —CO₂R⁴, or —SO₂R³ where:

$R^3$ is hydrogen, lower alkyl, halo lower alkyl or optionally substituted phenyl;

$R^4$ is hydrogen, lower alkyl or optionally substituted phenyl;

$R^5$ is hydrogen, lower alkyl or optionally substituted phenyl;

$R^6$ is lower alkyl or optionally substituted phenyl; and

Z is a side chain selected from Formulae ZA, ZB, ZC, ZD, ZE, ZF, ZG, and ZH:

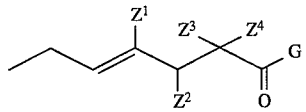

Formula ZA wherein:

$Z^1$ is H, lower alkyl, halo or $CF_3$;

$Z^2$ is H, lower alkyl, lower alkoxy, aryl, or $-CH_2Z^{13}$, where $Z^{13}$ is aryl or heteroaryl;

$Z^3$ is H, lower alkyl, lower alkenyl, lower alkoxy, phenyl, $P(O)(OCH_3)_2$, $-P(O)(OH)(OCH_3)$, or $-S(O)_mZ^{12}$, where
  $Z^{12}$ is lower alkyl, and
  m is 0, 1 or 2;

$Z^4$ is H, lower alkyl, or phenyl, or $Z^3$ and $Z^4$ taken together with the carbon to which they are attached form cycloalkyl of three to five carbon atoms; and G is OH, lower alkoxy, lower thioalkyl, $-NG^1G^2$, $-O(CH_2)_mNG^1G^2$, or $-O(CH_2)_mN=G^3$, where
  n is an integer from 1 to 6,
  $G^1$ is H or lower alkyl,
  $G^2$ is H or lower alkyl, and
  $=G^3$ is lower alkylene of four to six carbon atoms, or lower alkylene of three to five carbon atoms plus one member that is $-O-$, $-S-$, or $-N(G^4)-$ where $G^4$ is H or lower alkyl;

provided that when $Z^1$ is methyl, $Z^2$, $Z^3$ and $Z^4$ are not all H; or

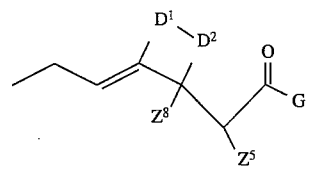

Formula ZB wherein:

$Z^5$ is H or lower alkyl;

$Z^6$ is H or lower alkyl;

$D^1$ and $D^2$ together with their adjacent carbon atoms form an optionally substituted, saturated or unsaturated carbocyclic or heterocyclic ring of 3 to 7 atoms; and G is as defined above; or

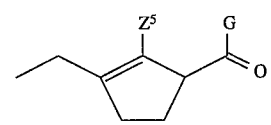

Formula ZC wherein:

$Z^5$, $Z^8$, and G are as defined above; or

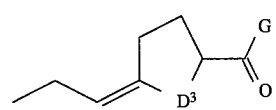

Formula ZD wherein:

$D^3$ is $-CH_2-$ or $-CH_2CH_2-$; and

G is as defined above; or

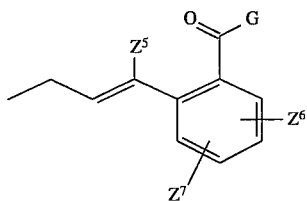

Formula ZE wherein:

$Z^6$ is H, lower alkyl, lower alkoxy, $-COOH$, $-NH_2$ or halo;

$Z^7$ is H, lower alkyl, lower alkoxy or halo; and $Z^5$ and G are as defined above; or

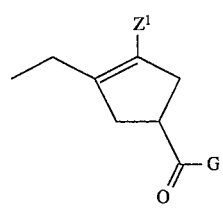

Formula ZF wherein:

$Z^1$ and G are as defined above; or

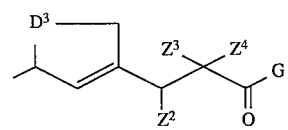

Formula ZG wherein:

$D^3$, $Z^2$, $Z^3$, $Z^4$ and G are as defined above; or

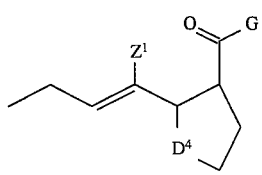

Formula ZH wherein:

$D^4$ is $-CH_2-$, $-CH_2CH_2-$, $-CH_2CH_2CH_2-$, $-O-$, or $-OCH_2-$; and $Z^1$ and G are as defined above; or a pharmaceutically acceptable salt thereof.

2. The compound or salt of claim 1, wherein Z is sidechain ZA.

3. The compound or salt of claim 2, wherein $Z^1$ is methyl.

4. The compound or salt of claim 3, wherein $R^1$ is hydrogen and $R^2$ is hydrogen or $-C(O)R^3$.

5. The compound or salt of claim 4, wherein $R^2$, $Z^2$ and $Z^3$ are all hydrogen, and $Z^4$ is methyl.

6. The compound or salt of claim 4, wherein $R^2$, $Z^3$ and $Z^4$ are all hydrogen, and $Z^3$ is methyl.

7. The compound or salt of claim 1, wherein Z is sidechain ZB.

8. The compound or salt of claim 7, wherein $R^1$ is hydrogen and $R^2$ is hydrogen or $-C(O)R^3$.

9. The compound or salt of claim 8, wherein $D^1$ and $D^2$ together with their adjacent carbon atoms form a saturated carbocyclic ring of 5 or 6 carbon atoms.

10. The compound or salt of claim 9, wherein $D^1$ and $D^2$ together represent $-CH_2CH_2CH_2-$, and $Z^5$ and $Z^8$ are both hydrogen.

11. The compound or salt of claim 10, wherein $R^1$ and $R^3$ are both hydrogen.

12. The compound or salt of claim 9, wherein $D^1$ and $D^2$ together represent —$CH_2CH_2CH_2CH_2$—, and $Z^5$ and $Z^8$ are both hydrogen.

13. The compound or salt of claim 12, wherein $R^1$ and $R^2$ are both hydrogen.

14. The compound or salt of claim 8, wherein $D^1$ and $D^2$ together with their adjacent carbon atoms form a saturated heterocyclic ring of 5 or 6 atoms.

15. The compound or salt of claim 14, wherein $D^1$ and $D^2$ together represent —$CH_2CH_2OCH_2$—, and $Z^5$ and $Z^8$ are both hydrogen.

16. The compound or salt of claim 15, wherein $R^1$ and $R^2$ are both hydrogen.

17. A pharmaceutical composition comprising a pharmaceutically acceptable non-toxic excipient and a therapeutically effective amount of a compound of claim 1, or a pharmaceutically acceptable salt thereof.

* * * * *

UNITED STATES PATENT AND TRADEMARK OFFICE
CERTIFICATE OF CORRECTION

PATENT NO. : 5,538,969
DATED : July 23, 1996
INVENTOR(S) : Morgans, Jr. et al.

It is certified that error appears in the above-identified patent and that said Letters Patent is hereby corrected as shown below:

Claim 1, at column 94, line 62 "$-CO_2R^4$" should read -- $-CO_2R^6$ --.

Claim 1, at column 95, line 17 "$P(O)(OCH_3)_2$" should read -- $-P(O)(OCH_3)_2$ --.

Claim 1, at column 95, line 27 "$-O(CH_2)_mNG^1G^2$, or $-O(CH_2)_mN=G^3$" should read -- $-O(CH_2)_nNG^1G^2$, or $-O(CH_2)_nN=G^3$ --.

Claim 6, at column 96, line 55 "$Z^3$ and" should read --$Z^2$ and--.

Claim 11, at column 97, line 1 "$R^3$" should read --$R^2$--.

Signed and Sealed this

Eighth Day of October, 1996

Attest:

BRUCE LEHMAN

*Attesting Officer*     *Commissioner of Patents and Trademarks*